United States Patent [19]

Theodoridis

[11] Patent Number: 5,136,868
[45] Date of Patent: Aug. 11, 1992

[54] HERBICIDAL 1-ARYL-4-SUBSTITUTED-1,4-DIHYDRO-5H-TETRAZOL-5-ONES AND SULFUR ANALOGS THEREOF

[75] Inventor: George Theodoridis, Princeton, N.J.
[73] Assignee: FMC Corporation, Philadelphia, Pa.
[21] Appl. No.: 455,773
[22] Filed: Dec. 28, 1989

Related U.S. Application Data

[63] Continuation-in-part of Ser. No. 814,575, Dec. 26, 1985, abandoned, which is a continuation-in-part of Ser. No. 671,532, Nov. 14, 1984, abandoned, which is a continuation-in-part of Ser. No. 549,334, Nov. 14, 1983, abandoned.

[51] Int. Cl.$^5$ ............... C07D 257/04; C07D 403/02; C07D 403/12; A01N 43/713
[52] U.S. Cl. ............................ 71/92; 548/251; 546/210; 546/271; 544/111
[58] Field of Search ................ 548/251; 71/92; 546/210, 271; 544/111

[56] References Cited

U.S. PATENT DOCUMENTS

| | | | |
|---|---|---|---|
| 3,437,665 | 6/1969 | Maggiulli et al. | 260/308 |
| 3,629,332 | 12/1971 | Harrington | |
| 3,755,605 | 8/1973 | Moore | |
| 3,865,570 | 2/1975 | George | 71/76 |
| 3,975,418 | 8/1986 | Duerr | |
| 4,213,773 | 7/1980 | Wolf | 71/92 |
| 4,315,767 | 2/1982 | Wolf | 71/91 |
| 4,318,731 | 3/1982 | Kajioka et al. | 71/92 |
| 4,349,378 | 9/1982 | Cliff | |
| 4,398,943 | 8/1983 | Kajioka et al. | 71/92 |
| 4,399,285 | 8/1983 | Föster et al. | 548/251 |
| 4,404,019 | 9/1983 | Uematsu et al. | 71/92 |
| 4,427,438 | 1/1984 | Nagano et al. | 71/92 |
| 4,431,822 | 2/1984 | Nagano et al. | 548/513 |
| 4,439,229 | 9/1984 | Swithenbank | 71/96 |
| 4,452,981 | 6/1984 | Nagano et al. | 544/236 |
| 4,552,585 | 11/1985 | Chang | |
| 4,618,365 | 10/1986 | Covey et al. | 71/92 |

FOREIGN PATENT DOCUMENTS

| | | |
|---|---|---|
| 3619 | 8/1979 | European Pat. Off. |
| 0011693 | 6/1980 | European Pat. Off. |
| 68822 | 1/1983 | European Pat. Off. |
| 0077938 | 6/1983 | European Pat. Off. |
| 0146279 | 6/1985 | European Pat. Off. |
| 1451028 | 7/1966 | France |
| 160447 | 8/1983 | German Democratic Rep. |
| 56-53662 | 5/1981 | Japan |
| 56-53663 | 5/1981 | Japan |
| 58-189178 | 11/1983 | Japan |
| 58-225070 | 12/1983 | Japan |
| 59-53466 | 3/1984 | Japan |
| 59-650744 | 4/1984 | Japan |
| 59-80661 | 5/1984 | Japan |
| 59-82360 | 5/1984 | Japan |
| WO85/01939 | 5/1985 | PCT Int'l Appl. |

OTHER PUBLICATIONS

H. Quast et al., "Synthese and Photolyse von 1,4–Dialkyl-1,4-dihydro-5H-tetrazol-5-onen und-thionen: Neue Wege zu Diaziridinonen und Carbodiimiden", *Chem. Ber.*, 114, 3253-3257 (1981).

O. Tsuge et al., "Reactions of Trimethylsilyl Azide with Heterocumulenes", *J. Org. Chem.*, 45, 5130-5136 (1980).

A. Vollmar et al., "Rearrangement of Tetrazole Ethers With Iodidide Ions (I)", *J. Heterocycl. Chem.*, 11, 491-496 (1974).

J-M Vandensavel et al., "Reactions of Azides with Isocyanates. Cycloadditions and Cycloreversions", *J. Org. Chem.*, 38, 675-678 (1973).

J. K. Elwood, et al., "Some Claisen Rearrangements in Heterocyclic Systems", *J. Org. Chem.*, 32, 2956-2959 (1967).

J. P. Horwitz et al., "The Synthesis of 1-Substituted 5(4H) Tetrazolinones", *J. Am. Chem. Soc.*, 81, 3076-3079 (1959).

M. Freund, "Martin Freund und Hans Hempel: Ueber Abkommlinge des Tetrazols", 74-81 (1895).

Agarwala et al., "Transition metal complexes of 1-substituted tetrazoline-5-thiones", *Can. J. Chem.*, 45, 1057 (1967).

Denecker et al., "Synthesis and Spectral Characteristics of Vinyltetrazolinones", *Tetrahedron*, 31, 765 (1975).

*Primary Examiner*—David B. Springer
*Attorney, Agent, or Firm*—Stanford M. Back; Robert M. Kennedy; H. Robinson Ertelt

[57] ABSTRACT

Herbicidal aryltetrazolinones and thiones of the formula

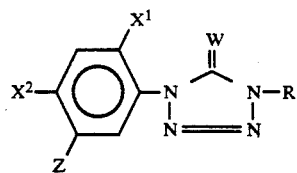

in which W is oxygen or sulfur; R is alkyl, fluoroalkyl, alkenyl, haloalkenyl, cyanoalkyl, alkylthioalkyl, haloalkoxyalkyl, trifluoromethylthio or alkoxyalkyl; one of $X^1$ and $X^2$ is fluorine, chlorine, or bromine and the other is fluorine, chlorine, bromine, alkyl, nitro or haloalkyl; and Z is a group selected from a variety of substituents including 2-propynyloxy as disclosed and exemplified.

41 Claims, No Drawings

HERBICIDAL 1-ARYL-4-SUBSTITUTED-1,4-DIHYDRO-5H-TETRAZOL-5-ONES AND SULFUR ANALOGS THEREOF

This application is a continuation-in-part of application Ser. No. 814,575, filed Dec. 26, 1985; which in turn is a continuation-in-part of application Ser. No. 671,532, filed Nov. 14, 1984; which in turn is a continuation in part of application Ser. No. 549,334, filed Nov. 14, 1983, all of which are abandoned.

The invention described in this application pertains to weed control in agriculture, horticulture, and other fields where there is a desire to control unwanted plant growth. More specifically, the present application describes a series of novel herbicidal 1-aryl-5-tetrazolinones and thiones, herbicidal compositions of them, methods of preparing them, and methods for preventing or destroying undesired plant growth by preemergence or postemergence application of the herbicidal compositions to the locus where control is desired. Also disclosed are intermediates useful in the preparation of the herbicidal compounds. The present herbicidal compounds may be used to effectively control a variety of both grassy and broadleaf plant species. The present invention is particularly useful in agriculture, as a number of the novel aryltetrazolinones described herein show a selectivity favorable to soybean, cotton, wheat, lima bean, corn, sorghum, or other crops at application levels which inhibit the growth of or destroy a variety of weeds.

1-Phenyl-5(4H)-tetrazolinone, formula A below wherein Y and R are hydrogen, is believed to be the first 1-aryl-5-tetrazolinone reported in the literature. The compound was made by M. Freund et al. and described in Ber., 28, 78 (1895).

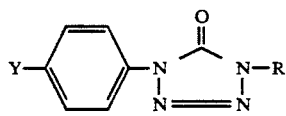

A

In the almost ninety years since disclosure of the parent compound, only a handful of substituted derivatives of it have been described in the literature.

1-(Monosubstituted-phenyl)-5-tetrazolinones of formula A are disclosed in a paper by J. P. Horwitz et al. in *J.Am. Chem. Soc.*, 81, 3076 (1959). In the disclosed compounds, Y is methyl, methoxy, chloro, bromo, nitro, or amino and R is hydrogen.

O. Tsuge et al., *J. Org. Chem.*, 45, 5130 (1980), disclose a number of the compounds disclosed by Horwitz et al., above, and additional compounds of formula A wherein the phenyl group is unsubstituted (Y is hydrogen) and R is phenylaminocarbonyl, acetyl, or 2-methylpropanoyl.

J-M. Vandensavel et al., *J. Org. Chem.*, 38, 675 (1973), report the preparation of compounds of formula A above wherein Y is hydrogen and R is n-butyl or 4-chlorophenylsulfonyl, Y is nitro and R is n-butyl or cyclohexyl, and Y is chloro or methoxy and R is 4-chlorophenylsulfonyl.

J. K. Elwood et al., *J. Org. Chem.*, 32, 2956 (1967), describe compounds of formula A wherein Y is hydrogen and R is 2-propenyl, 1-methyl-2-propenyl, or 2-butenyl.

Additional compounds of formula A wherein R is methyl and Y is hydrogen, chloro, or nitro, or R is benzyl and Y is chloro are disclosed by A. Vollmar et al., *J. Heterocycl. Chem.*, 11, 491 (1974).

None of the disclosed compounds above have been described in the references as having herbicidal properties.

The present invention provides a series of herbicidal compounds of the formula

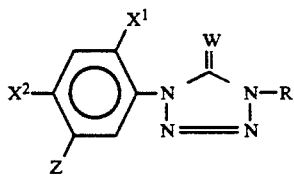

I wherein W is oxygen or sulfur;

R is alkyl (preferably of 1 to 6 carbon atoms), haloalkyl (preferably of 1 to 5 carbon atoms), alkoxyalkyl (preferably of 2 to 6 carbon atoms), alkylthioalkyl (preferably of 2 to 6 carbon atoms), cyanoalkyl (preferably of 1 to 5 alkyl carbon atoms), haloalkoxyalkyl (preferably of 2 to 6 carbon atoms), trifluoromethylthio, alkenyl (preferably of 2 to 5 carbon atoms), or haloalkenyl (preferably of 2 to 5 carbon atoms); and One of $X^1$ and $X^2$ is fluorine, chlorine, or bromine and the other is fluorine, chlorine, bromine, alkyl (preferably of 1 to 6 carbon atoms) such as methyl, or haloalkyl (preferably of 1 to 5 carbon atoms) such as bromomethyl, fluoromethyl, or trifluoromethyl. When $X^1$ is fluorine, chlorine, or bromine, $X^2$ may be selected from the substituents above and nitro.

Z is defined below.

Separate aspects of the invention pertain to sub-genera for the individual substituent groups above.

In one such aspect W will be oxygen.

In a sub-genus for R, that group may be alkyl of 1 to 6 (preferably 1 to 4) carbon atoms such as n-$C_3H_7$, a fluoroalkyl radical of 1 to 5 (preferably 1 to 4) carbon atoms and one or more (preferably 1 to 3) fluorine atoms, especially a fluoropropyl radical such as 3-fluoropropyl, alkoxyalkyl or alkylthioalkyl of 2 to 4 carbon atoms such as methoxymethyl or its thio analog, cyanoalkyl of 1 to 3 alkyl carbon atoms such as cyanomethyl, fluoroalkoxyalkyl of 2 to 4 carbon atoms and 1 to 3 fluorine atoms, for example, 2-(difluoromethoxy)ethyl, trifluoromethylthio, alkenyl of 3 to 5 carbon atoms such as 2-propenyl, or haloalkenyl of 3 to 5 carbon atoms, for example, a fluoroalkenyl of 1 or 2 fluorine atoms such as 3-fluoro-2-propenyl. In a preferred embodiment R is n-$C_3H_7$ or a fluoropropyl radical such as 3-fluoropropyl. Typical R groups include —$CH_3$, —$CH_2CH_3$, —$(CH_2)_2CH_3$, —$CH(CH_3)_2$, —$(CH_2)_3CH_3$, —$CH_2CH(CH_3)_2$, —$CH(CH_3)CH_2CH_3$, —$CHF_2$, —$CH_2CH_2F$, —$(CH_2F$, —$(CH_2)_2CH_2Br$, —$(CH_2)_2CHF_2$, —$CH_2CHFCH_3$, —$CH_2CF_2CH_3$, —$CH_2OCH_3$, —$H_2OCH_2CH_3$, —$CH_2SCH_3$, —$CH_2CN$, —$CH_2CH_2OCHF_2$, —$SCF_3$, —$CH=CH_2$, —$CH_2CH=CH_2$, and —$CH_2CH=CHF$.

With respect to sub-genera for $X^1$ and $X^2$, $X^1$ may be fluorine, chlorine, bromine, methyl, or trifluoromethyl, and $X^2$ may be fluorine, chlorine, bromine, methyl, ethyl, bromomethyl, fluoromethyl, trifluoromethyl, or nitro, one of $X^1$ and $X^2$ being fluorine, chlorine, or bromine. In a preferred embodiment, $X^1$ and $X^2$ independently will be selected from fluorine, chlorine, and bromine. In a particularly preferred embodiment $X^1$ will be chlorine or, especially, fluorine and $X^2$ will be chlorine or bromine.

It will be understood that any alkyl, alkenyl or alkynyl groups of the compound may be straight chain or branched chain radicals. Thus, 1-methylethyl, 2-methyl-2-propenyl, and 1-methyl-2-propynyl are branched chain examples of alkyl, alkenyl, and alkynyl radicals respectively. The halogen may be fluorine, chlorine, bromine or iodine. The haloalkyl radical may have one or more same or different halogen atoms.

In one aspect of the invention, Z is hydrogen and W, R, $X^1$, and $X^2$ are as defined above. Preferably W is oxygen and R is n-propyl or a fluoropropyl radical such as 3-fluoropropyl. $X^1$ and $X^2$ are preferably independently selected from fluorine, chlorine, and bromine. More preferably, $X^1$ is chlorine or, especially, fluorine and $X^2$ is chlorine or bromine. The compounds in which Z is hydrogen are generally less active herbicidally than the corresponding compounds in which Z is one of the substituent groups described below.

Z may also be selected from fluorine, chlorine, bromine, cyano, nitro, alkyl (preferably of 1 to 6 carbon atoms) such as methyl, alkyl (preferably of 1 to 5 carbon atoms) substituted with one or more fluorine, chlorine, or bromine atoms or alkoxy groups of 1 to 4 carbons, and alkynyl (preferably of 3 to 5 carbon atoms) such as 2-propynyl. Examples of substituted alkyl include —$CF_3$ and acetal and ketal groups such as —CH($OC_2H_5$)$_2$ and —C($CH_3$)($OC_2H_5$)$_2$. W, $X^1$, $X^2$, and R are as defined above, both generically and otherwise.

Z may also be a radical selected from the group consisting of

—$QR^1$,
—OSO $R^2$,
—Q—$R^7$—CO—$Q^1R^8$,
—Q—$R^7$—$CO_2$—N=C($R^9$)($R^{10}$),
—Q—$R^7$—C($CH_3$)=$R^{11}$,
—Q—$R^7$—CO—N($R^{12}$)($R^{13}$),
—N($R^{14}$)($R^{15}$),
—$SO_2R^{16}$, and
—CO—$R^{17}$, the substituents W, $X^1$, $X^2$, and R being as defined above both generically and otherwise.

Z is —$QR^1$

Q is sulfur or, preferably, oxygen and $R^1$ is alkyl (preferably of 1 to 6, more preferably of 1 to 4, carbon atoms), haloalkyl (preferably of 1 to 5 carbon atoms), particularly a fluoroalkyl, hydroxyalkyl (preferably of 2 to 5, more preferably of 2 or 3, carbon atoms), cyanoalkyl (preferably of 1 to 5 alkyl carbon atoms), alkoxyalkyl (preferably of 2 to 6 carbon atoms), alkylthioalkyl, alkylsulfinylalkyl, or alkylsulfonylalkyl (each preferably of 2 to 6 carbon atoms), alkanoyl (preferably of 2 to 5 carbon atoms), alkenyl (preferably of 2 to 5, more preferably of 3 to 5, carbon atoms), haloalkenyl (preferably of 2 to 5, more preferably of 3 to 5, carbon atoms) such as a halo-2-propenyl, alkenyloxyalkyl (preferably of 3 to 6 carbon atoms), alkynyl (preferably of 2 to 5, more preferably 3 to 5, carbon atoms), haloalkynyl (preferably of 2 to 5, more preferably 3 to 5, carbon atoms), alkoxycarbonyl (preferably of 1 to 4 alkyl carbon atoms), or a three- to eight-membered ring heterocyclic group of one or two, same or different (preferably the same), ring heteroatoms selected from oxygen and sulfur or an alkyl radical (preferably of 1 to 4, more preferably 1, carbon atoms) substituted with said heterocyclic group. $R^1$ is preferably 2-propynyl or 3-halo-2-propynyl such as 3-iodo-2-propynyl or 3-bromo-2-propynyl.

When $R^1$ is a heterocyclic group or an alkyl radical substituted therewith, the heterocyclic group may be saturated, unsaturated, or aromatic, it may be substituted with halogen (generally fluorine, chlorine, or bromine), alkyl, (preferably of 1 to 4 carbon atoms), or haloalkyl (preferably of 1 to 4 carbon atoms), and it may be adjoined to a benzene ring at two adjacent ring carbon atoms to form a benzo-heterocycle bicyclic group, for example a 1,4-benzodioxanyl group. In sulfur-containing heterocycles, the sulfur may be present in divalent form or as the S-oxide or S-dioxide. In a sub-genus of particular interest, the heterocyclic group is saturated, unsubstituted, of 5 or 6 ring atoms including 1 or 2 same ring heteroatoms (sulfur or oxygen), and is connected directly to the Q (preferably oxygen) moiety of the Z group or indirectly via methylene group. In this sub-genus Z is advantageously 3-tetrahydrofuranyloxy or tetrahydrofurfuryloxy.

Examples of Z groups when Z is —$QR^1$ and $R^1$ is other than (and does not contain) a heterocyclic group include such radicals as —$OCH_3$, —$OC_2H_5$, —O—n—$C_3H_7$, —OCH($CH_3$)$_2$, —O—n—$C_4H_9$, —$OCH_2CH(CH_3)_2$, —$SCH_3$, —CH($CH_3$)$_2$, —$OCHF_2$, —$SCHF_2$, —$OCH_2CH_2F$, , —$OCH_2CF_3$, —$SCH_2CF_3$, —O($CH_2$)$_2CH_2F$, —$OCH_2CH_2Cl$, —$OCH_2CH_2Br$, —$OCH_2CH_2OH$, —$SCH_2CH_2OH$, —$OCH_2CN$, —$SCH_2CN$, —OCH($CH_3$)CN, —OCH(CN)CH($CH_3$)$_2$, —$OCH_2OCH_3$, —$OCH_2OC_2H_5$, —$SCH_2OCH_3$, —($CH_2$)$_2OCH_3$, —OCH($CH_3$)$OCH_3$, —O($CH_2$)$_2OC_2H_5$, $OCO_2C_2H_5$, —S($CH_2$)$_2OCH_3$, —OCH($CH_3$)$CH_2OCH_3$, —$OCH_2SCH_3$, —$SCH_2SCH_3$, —$OCH_2S(O)CH_3$, —OCH($CH_3$)$SCH_3$, —OCH($CH_3$)S(O)$CH_3$, —OCH($CH_3$)S(O)$_2CH_3$, —O($CH_2$)$_2OCH=CH_2$, —S($CH_2$)$_2OCH=CH_2$, —O($CH_2$)$_2OCH_2CH=CH_2$, —$OCOCH_3$, —$SCOCH_3$, —OCOCH($CH_3$)$_2$, —$OCH_2CH=CH_2$, OCH($CH_3$)C=$CH_2$, —$SCH_2CH=CH_2$—$OCH_2C(Cl)=CH_2$, —$SCH_2C(Cl)=CH_2$, —$OCH_2CBr=CHBr$, —$OCH_2C≡CH$, —$SCH_2C≡CH$, —$OCH_2C≡CCH_3$, —OC($CH_3$)$_2C≡CH$, —OCH($CH_3$)C≡CH, —$OCH_2C≡CI$, and —$OCH_2C≡CBr$.

Examples of Z when $R^1$ is or contains a heterocyclic groups include

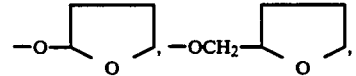,

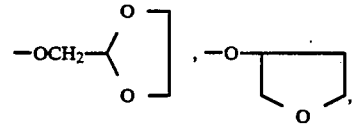,

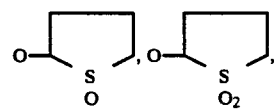,

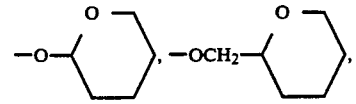

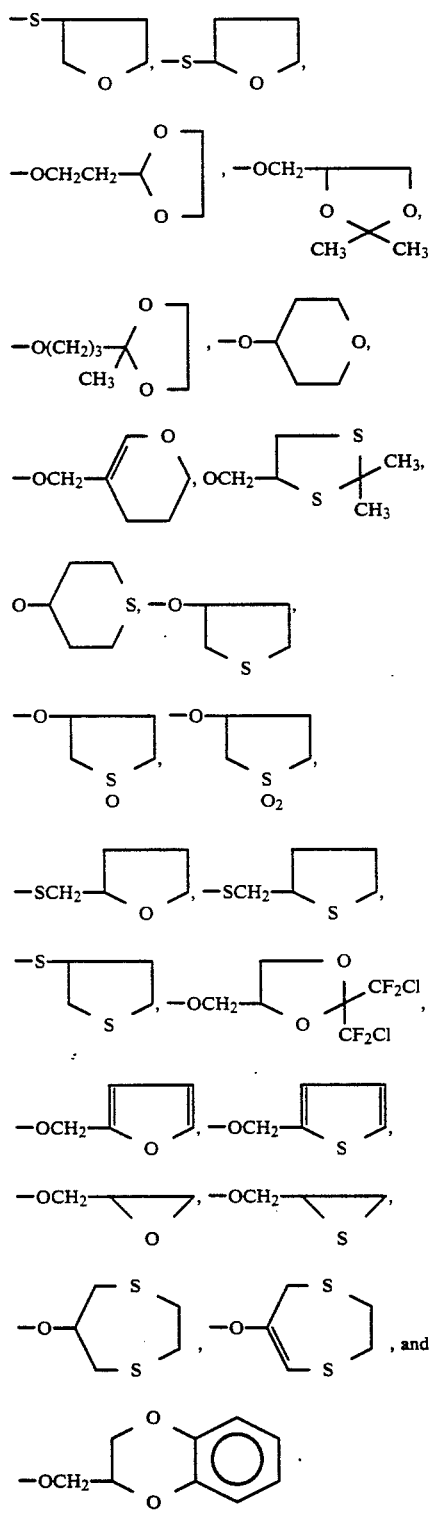

Z is —OSO$_2$R$^2$

R$^2$ is alkyl (preferably of 1 to 8 carbon atoms), haloalkyl, cyanoalkyl, or arylalkyl wherein each alkyl is preferably of 1 to 5 carbon atoms, cyclic alkyl (preferably of 3 to 8 carbon atoms), alkenyl, haloalkenyl, or arylalkenyl wherein each alkenyl is preferably of 2 to 5 carbon atoms, alkynyl, haloalkynyl, or arylalkynyl wherein each alkynyl is preferably of 2 to 5 carbon atoms, aryl such as phenyl, or a group of the formula —(CH$_2$)$_m$NR$^3$R$^4$ or (CH$_2$)$_n$—Y—R$^5$ wherein m is 0 to 5 (preferably 0 to 3) and n is 1 to 5 (preferably 1 to 3);

R$^3$ is hydrogen or alkyl (preferably of 1 to 5 carbon atoms);

R$^4$ is alkyl (preferably of 1 to 5 carbon atoms) or a group —CH$_2$—Y—R$^5$;

R$^5$ is alkyl (preferably of 1 to 5 carbon atoms), alkenyl or alkynyl (preferably of 2 to 5, more preferably of 3 to 5, carbon atoms), or a radical —CH(R$^{18}$)CO$_2$R$^{19}$;

R$^{18}$ and R$^{19}$ are independently hydrogen or alkyl (preferably of 1 to 4 carbon atoms); and Y is oxygen or S(0)r in which r is 0 to 2.

A number of interesting compounds within the above subgenus comprise the series wherein R$^2$ is alkyl of 1 to 8 carbon atoms, haloalkyl, cyanoalkyl, or arylalkyl wherein each alkyl is of 1 to 5 carbon atoms, cyclic alkyl of 3 to 8 carbon atoms, alkenyl or haloalkenyl of 3 to 5 carbon atoms, alkynyl or haloalkynyl of 3 to 5 carbon atoms, or a group (CH$_2$)$_m$NR$^3$R$^4$ or (CH$_2$)$_n$—Y—R$^5$ wherein m is 0 to 3, n is 1 to 3, and R$^3$ and R$^4$ are independently alkyl of 1 to 5 carbon atoms.

Frequently, R$^2$ will be alkyl of 1 to 5 carbon atoms, especially methyl; haloalkyl of 1 to 3 carbon atoms having one or more fluorine, chlorine, or bromine atoms; cyanoalkyl or phenylalkyl of 1 to 3 alkyl carbon atoms; cyclic alkyl of 3 to 6 carbon atoms; alkenyl or alkynyl of 3 to 5 carbon atoms; haloalkenyl of 3 to 5 carbon atoms such as a halopropenyl, for example, a halo-2-propenyl having one or more halogen atoms such as chlorine; haloalkynyl of 3 to 5 carbon atoms, especially a 3-halo-2-propynyl, a group of the formula (CH$_2$)$_m$N(R$^3$)$_2$ in which m is 0 or 2 and R$^3$ is alkyl of 1 to 5 carbon atoms such as methyl; or a group of the formula (CH$_2$)$_n$—Y—R$^5$ in which n is 1 or 2, especially 2, Y is oxygen or sulfur, and R$^5$ is alkyl of 1 to 5 carbon atoms such as methyl or ethyl, alkenyl or alkynyl of 3 to 5 carbon atoms, or a radical —CH(R$^{18}$)CO$_2$R$^{19}$ in which R$^{18}$ is hydrogen or methyl and R$^{19}$ is alkyl of 1 to 4 carbon atoms such as methyl or ethyl.

Examples of specific R$^2$ groups include CH$_3$, C$_2$H$_5$, n—C$_3$H$_7$, CH(CH$_3$)$_2$, n—C$_4$H$_9$, CH$_2$CH(CH$_3$)$_2$, CH(CH$_3$)CH$_2$CH$_3$, (CH$_2$)$_2$CH(CH$_3$)$_2$, CF$_3$, CHF$_2$, CH$_2$—Cl, CHCl$_2$, CH$_2$Br, (CH$_2$)$_2$CH$_2$Cl, CH$_2$CN, CH$_2$C$_6$H$_5$, $$\overset{\text{CHCH}_2\text{CH}_2,}{\underbrace{\qquad\qquad}}$$

CH=CH$_2$, CH$_2$CH=CH$_2$, CH$_2$C(Cl)=CCl$_2$, CH$_2$=CHC$_6$H$_5$, CH$_2$C≡CH, CH$_2$C≡Cl, C$_6$H$_5$, NHCH$_3$, N(CH$_3$)$_2$, (CH$_2$)$_2$N(CH$_3$)$_2$, (CH$_2$)$_2$OCH$_3$, (CH$_2$)$_2$OCH$_2$CH$_3$, (CH$_2$)$_2$OCH$_2$CH=CH$_2$, (CH$_2$)$_2$SCH$_2$CH=CH$_2$, (CH$_2$)$_2$OCH$_2$C≡CH, (CH$_2$)$_2$OCH$_2$CO$_2$CH$_3$, and (CH$_2$)$_2$SCH$_2$CO$_2$CH$_3$.

Z is —Q—R$^7$—CO—Q$^1$R$^8$

Q and Q$^1$ are independently oxygen or sulfur.

R$^7$ is an alkylene or haloalkylene (such as fluoroalkylene) radical, preferably of 1 to 3 carbon atoms, for example, —CH$_2$—, —CH(CH$_3$)—, or —CHF—.

R$^8$ is hydrogen, alkyl or substituted alkyl (preferably of 1 to 8 carbon atoms), alkenyl or alkynyl (preferably of 2 to 5, more preferably 3 to 5, carbon atoms), for example, 2-propenyl, 1-methyl-2-propenyl, or 2-propynyl, or a monovalent cyclic group of 3 to 7 ring atoms which may be an aromatic (such as phenyl), heterocyclic (such as 3-tetrahydrofuranyl, 2-oxo-3-tetrahydrofuranyl, 3-tetrahydrothienyl or the oxide or dioxide thereof, or 3-pyridyl), or alicyclic (such as cyclopropyl, cyclopentyl, or cyclohexyl) radical, the valence being on a carbon atom of said cyclic group, or an alkyl radical of 1 to 3 (preferably 1) carbon atoms substituted with said cyclic group, for example, cyclopropylmethyl, tetrahydrofurfuryl, furfuryl, thenyl, or benzyl.

When $R^8$ is substituted alkyl, the alkyl substituent(s) will frequently be selected from nitro, halo (such as chloro, bromo, or, particularly, fluoro), cyano, alkoxy or alkyl(thio, sulfinyl, or sulfonyl) of 1 to 4 alkyl carbon atoms, phenyl(thio, sulfinyl, or sulfonyl), alkylamino or dialkylamino in which each alkyl independently is preferably of 1 to 4 carbon atoms, aminocarbonyl, or alkylaminocarbonyl or dialkylaminocarbonyl in which each alkyl independently is preferably of 1 to 4 carbon atoms.

Thus, in this aspect of the invention, Z may be $-OR^7CO_2R^8$, $-SR^7-CO-SR^8$, $-OR^7-CO-SR^8$, or $-SR^7CO_2R^8$.

In a narrower aspect of the invention Q is oxygen or sulfur (frequently oxygen), $Q^1$ is oxygen, $R^7$ is $-CH_2-$ or $-CH(CH_3)-$, and $R^8$ is hydrogen, alkyl, haloalkyl (particularly a fluoroalkyl), cyanoalkyl, alkoxyalkyl, cyclic alkyl such as cyclopentyl, (cyclic alkyl)alkyl such as cyclopropylmethyl, or alkynyl.

Examples of Z groups when Z is $-Q-R^7-CO-Q^1R^8$ include $OCH_2CO_2H$, $OCH_2CO_2C_2H_5$, $SCH_2CO_2H$, $SCH_2-CO-SCH_3$, $-OCH(CH_3)CO_2C_2H_5$, $OCH(CH_3)CO_2CH(CH_3)_2$, $OCH(CH_3)CO_2C(CH_3)_3$, $OCH(CH_3)CO_2CH(CH_2CH_3)_2$, $OCH(CH_3)CO_2CH(CH_3)CH(CH_3)_2$, $OCH(CH_3)CO_2CH[CH(CH_3)_2]_2$, $OCH(CH_3)CO_2CH(CH_3)CH_2CH_3$, $OCH(CH_3)CO_2CH(CH_2)_3CH_2$, $OCH(CH_3)CO_2H$, $SCH(CH_3)CO_2CH(CH_3)_2$, $OCH(CH_3)CO_2CH_2CHCH_2CH_2$, $SCH(CH_3)CO_2H$, $OCH(CH_3)CO_2C(CN)(CH_3)_2$, $OCH(CH_3)CO_2CH(CH_2OCH_3)_2$, $OCH(CH_3)CO_2CH(CH_3)C\equiv CH$, $OCH(CH_3)CO_2C(CH_3)_2C\equiv CH$, $OCH(CH_3)CO_2CH_2CH_2F$, $OCH(CH_3)CO_2CH_2CF_3$, $OCH(CH_3)CO_2CH(CH_2F)_2$, $OCHFCO_2H$, $SCHFCO_2H$, $OCHFCO_2CH_3$, $OCH_2CO-SC_2H_5$, $OCH(CH_3)-CO-SC_2H_5$, $-OCH(CH_3)CO_2CH_2CH=CH_2$, $-SCH(CH_3)CO_2CH_2CH=CH_2$, $OCH_2CO_2C_6H_5$, $OCH(CH_3)CO_2-$[tetrahydrofuran], $OCH(CH_3)CO_2-$[dioxolanone], $OCH(CH_3)CO_2-$[tetrahydrothiophene], $OCH_2CO_2-$[tetrahydrothiophene sulfoxide], $OCH_2CO_2-$[tetrahydrothiophene sulfone], $SCHFCO_2-$[pyridyl], $OCH(CH_3)CO_2CH(CH_2)_4CH_2$, $SCH_2CO_2CHCH_2CH_2$, $OCH(CH_3)CO_2CH_2-$[tetrahydrofuran], $OCH(CH_3)CO_2CH_2-$[tetrahydrofuran], $OCH(CH_3)CO_2CH_2C_6H_5$, $OCH(CH_3)CO_2CH_2-$[tetrahydrothiophene], $OCH(CH_3)CO_2CH_2CH_2N(CH_3)_2$, $OCH(CH_3)CO_2CH_2CON(C_2H_5)_2$, $SCH(CH_3)CO_2CH_2OCH_3$, $OCH(CH_3)CO_2CH_2SCH_3$, $OCH(CH_3)CO_2CH_2SOCH_3$, $OCH(CH_3)CO_2CH_2SO_2CH_3$, $OCH(CH_3)CO_2CH_2CONH_2$, $OCH(CH_3)CO_2CH_2CH(NO_2)CH_3$, $OCH(CH_3)CO_2CH_2CN$, and $OCH(CH_3)CO_2CH_2SC_6H_5$.

The free acids (Z is $-QR^7CO_2H$) may be converted into their salts such as their sodium, potassium, calcium, ammonium, magnesium, or mono-, di-, or tri($C_1$ to $C_4$ alkyl)ammonium salts which may also be used as herbicides.

Z is $-Q-R^7-CO_2-N=C(R^9)(R^{10})$

Q and $R^7$ are as defined above.

One of $R^9$ and $R^{10}$ is alkyl and the other is alkyl or alkylthio, each alkyl (independently) preferably being of 1 to 4 carbon atoms.

Examples of Z include $OCH(CH_3)CO_2N=C(CH_3)_2$, $SCH_2CO_2N=C(CH_3)_2$, $OCHFCO_2N=C(SCH_3)(CH_3)$, $OCH(CH_3)CO_2N=C(SCH_3)(CH_3)$, $OCH(CH_3)CO_2N=C(CH_3)(C_2H_5)$, and $OCH_2CO_2N=C(CH_3)_2$.

Z is $-Q-R^7-C(CH_3)=R^{11}$

Q and $R^7$ are as defined above.

$R^{11}$ is oxygen or $N-OR^{20}$ in which $R^{20}$ is hydrogen or alkyl (preferably of 1 to 4 carbon atoms).

Examples of Z substituents for this sub-genus include $OCH(CH_3)C(CH_3)=N-OH$, $SCH(CH_3)C(CH_3)=N-OH$, $OCH_2C(CH_3)=N-OH$, $OCHFC(CH_3)=N-OH$, $SCH(CH_3)C(CH_3)=N-OCH_3$, $OCH(CH_3)C(CH_3)=N-OCH(CH_3)_2$, $OCH(CH_3)COCH_3$, $SCH(CH_3)COCH_3$, $OCHFCOCH_3$, $OCH_2COCH_3$, and $SCH_2COCH_3$.

Z is $-Q-R^7-CO-N(R^{12})(R^{13})$

Q and $R^7$ as defined above.

$N(R^{12})(R^{13})$ $NH_2$ or the residue of a primary or secondary amine or of a sulfonamide. For example, one of $R^{12}$ and $R^{13}$ may be hydrogen, alkyl (preferably of 1 to 4 carbon atoms), or alkenyl (preferably of 3 to 5 carbon atoms) such as 2-propenyl, and the other may be hydrogen, alkyl (preferably of 1 to 4 carbon atoms), cyanoalkyl (preferably of 1 to 4 alkyl carbon atoms), alkoxyalkyl (preferably of 2 to 4 carbon atoms), alkenyl (preferably of 3 to 5 carbon atoms) such as 2-propenyl, alkynyl (preferably of 3 to 5 carbon atoms) such as 2-propynyl, alkylsulfonyl (preferably of 1 to 4 carbon atoms), arylsulfonyl in which aryl is unsubstituted phenyl or phenyl substituted with halogen (such as fluorine or chlorine)

or alkyl (preferably of 1 to 4 carbon atoms such as methyl), haloalkylsulfonyl (preferably of 1 to 4 carbon atoms), for example, a fluoroalkylsulfonyl such as trifluoromethylsulfonyl, alkylaminosulfonyl or dialkylaminosulfonyl in which each alkyl independently is preferably of 1 to 4 carbon atoms, or CH(H or CH$_3$)CO$_2$alkyl in which alkyl is preferably of 1 to 4 carbon atoms. R$^{12}$ and R$^{13}$ may also be taken together and with the nitrogen atom form a 5- or 6-membered heterocyclic ring which may contain an oxygen atom in the ring, for example, N(R$^{12}$)(R$^{13}$) may be a pyrrolidino, piperidino, or morpholino ring.

In one aspect of this embodiment, R$^{12}$ and R$^{13}$ will be the same or will be taken together to form a heterocyclic ring. In another aspect one of R$^2$ and R$^{13}$ will be alkyl or, frequently, hydrogen and will be different from the other.

Examples of Z substituents for this embodiment include OCH(CH$_3$)CONH$_2$, OCH(CH$_3$)CON(CH$_3$)$_2$, OCH(CH$_3$)CON(CH$_2$CH=CH$_2$)$_2$, OCH(CH$_3$)CONHSO$_2$C$_6$H$_5$, OCH(CH$_3$)CONHSO$_2$—C$_6$H$_4$(2—Cl), OCH(CH$_3$)CONHSO$_2$—C$_6$H$_4$(4—Cl), OCH$_2$CON(CH$_3$)(C$_2$H$_5$), OCH(CH$_3$)CONHCH(CH$_3$)$_2$, OCHFCONHSO$_2$—n—C$_3$H$_7$, OCH(CH$_3$)CONHCH$_2$C≡CH, OCH(CH$_3$)CONHCH$_2$CO$_2$CH$_3$, OCH(CH$_3$)CONHSO$_2$—C$_6$H$_4$(4—CH$_3$), OCH(CH$_3$)CONHC(CH$_3$)$_2$C≡CH, OCH(CH$_3$)CONHC(CH$_3$)$_2$CN, OCH(CH$_3$)CONHSO$_2$CF$_3$, OCH(CH$_3$)CONHSO$_2$NHCH$_3$, OCH(CH$_3$)CONHSO$_2$N(CH$_3$)$_2$, OCH(CH$_3$)CONHCH$_2$CH$_2$OCH$_3$, OCH$_2$CONH$_2$, OCHFCONHCH$_3$, OCH(CH$_3$)CONHCH(CH$_3$)CO$_2$C$_2$H$_5$, SCH(CH$_3$)CON(CH$_3$), SCH(CH$_3$)CONHCH$_2$CH=CH$_2$,

OCH(CH$_3$)CON(CH$_2$)$_4$CH$_2$, OCH(CH$_3$)CON(CH$_2$)$_3$CH$_2$,

OCH(CH$_3$)CON(CH$_2$)$_2$OCH$_2$CH$_2$, and SCH$_2$CONHSO$_2$CF$_3$.

Z is N(R$^{14}$)(R$^{15}$).

R$^{14}$ and R$^{15}$ are independently selected from hydrogen, alkyl (preferably of 1 to 4 carbon atoms), alkenyl or alkynyl (preferably of 3 to 5 carbon atoms), cyanoalkyl (preferably of 1 to 4 alkyl carbon atoms), acetyl, alkoxycarbonyl (preferably of 1 to 4 alkyl carbon atoms), alkoxyalkyl (preferably of 2 to 4 carbon atoms), aminocarbonyl, alkylaminocarbonyl or dialkylaminocarbonyl in which each alkyl is preferably of 1 to 4 carbon atoms, alkylsulfonyl (preferably of 1 to 4 carbon atoms), haloalkylsulfonyl (preferably of 1 to 4 carbon atoms), for example, a fluoroalkylsulfonyl such as trifluoromethylsulfonyl, arylsulfonyl in which aryl is unsubstituted phenyl or phenyl substituted with halogen (such as fluorine or chlorine) or alkyl (preferably of 1 to 4 carbon atoms such as methyl), and CH(H or CH$_3$)CO$_2$—alkyl in which alkyl is preferably of 1 to 4 carbon atoms, or N(R$^{14}$)(R$^{15}$) is a group N=C(R$^9$)(R$^{10}$) in which one of R$^9$ and R$^{10}$ is alkyl and the other is hydrogen, alkyl, or alkylthio, each alkyl (independently) preferably being of 1 to 4 carbon atoms. N(R$^{14}$)(R$^{15}$) may also represent a cyclic group such as tetrahydrophthalimido or 2-oxopyrrolidino.

Examples of Z groups for this embodiment include NHCON(CH$_3$)$_2$, NHCONH$_2$, NHCONHCH$_2$CH(CH$_3$)$_2$, NHCONHCH$_3$, NH$_2$, N(CH$_3$)$_2$, NHCH$_3$, N(C$_2$H$_5$)$_2$, NHCH$_2$CH=CH$_2$, NHCH$_2$C≡CH, N(CH$_2$CN)COCH$_3$, N(C$_2$H$_5$)COCH$_3$, NHCOCH$_3$, NHCH$_2$CO$_2$C$_2$H$_5$, NHCO$_2$CH$_3$, NHCH(CH$_3$)CO$_2$C$_2$H$_5$, NHCH$_2$CH$_2$OCH$_3$, NHSO$_2$CH$_3$, N(CH$_3$SO$_2$CH$_3$, N(C$_2$H$_5$)SO$_2$CH$_3$, N(SO$_2$CH$_3$)$_2$, NHSO$_2$CF$_3$, N(SO$_2$CF$_3$)$_2$, NHSO$_2$C$_6$H$_5$, NHSO$_2$—C$_6$H$_4$(4—Cl), NHSO$_2$—C$_6$H$_4$(4-CH$_3$), N=C(CH$_3$)$_2$, N=CHCH$_3$, N=C(CH$_3$)(C$_2$H$_5$), N=C(SCH$_3$)(CH$_3$),

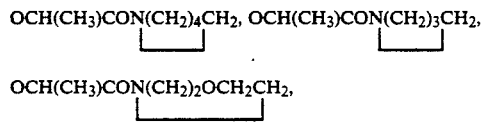, and 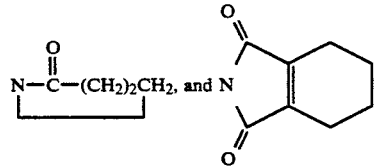.

In a particularly useful class of compounds in which Z is N(R$^{14}$)(R$^{15}$), Z is —N($^{31}$)SO$_2$R$^{30}$ wherein R$^{30}$ may be alkyl (such as straight chain or branched chain lower alkyl, e.g. methyl, ethyl, propyl), haloalkyl (such as CF$_3$ or CHF$_2$), aryl (such as phenyl, optionally substituted with one or more of: halogen such as Cl, Br or F; alkyl such as lower alkyl, e.g. methyl; alkoxy such as lower alkoxy, e.g. methyoxy, cyano; cyanomethyl; nitro, amino; arylamino such as phenylamino; mono- and dialkylamino such as methylamino or dimethylamino; carboxyl; alkoxycarbonyl such as —COOC$_2$H$_5$; alkoxyalkyl such as alkoxymethyl of 2 to 4 carbon atoms; alkoxycarbonylalkyl such as —CH$_2$COOC$_2$H$_5$; benzyl; or hydroxy).

R$^{31}$ may be hydrogen, alkyl (e.g. straight or branched chain lower alkyl such as methyl, ethyl, propyl, isopropyl, or butyl), benzyl, haloalkyl (e.g. CHF$_2$ or CH$_2$CH$_2$CH$_2$F), alkoxy (e.g. methoxy), SO$_2$R, alkynyl (such as propargyl), alkenyl (such as allyl), a group of the formula -alkylene—SO$_2$R (in which, for example, said alkylene group (e.g. —CH$_2$—) has 1 to 4 carbon atoms, alkoxymethyl (such as methoxymethyl), cyanomethyl or ethoxycarbonylmethyl.

R$^{30}$ and R$^{31}$ together may be a divalent radical such as alkylene (e.g. of 1 to 10 carbon atoms such as methylene or 1,3-propylene).

R$^{31}$ may also be a salt-forming group such as a metal (e.g. Na, K or Ca) or ammonium (e.g. NH$_4$ or lower alkyl-substituted ammonium).

In each aspect of the invention, it is often preferable that any alkyl, alkenyl, alkynyl or alkylene radical have less than 6 carbon atoms.

The compounds in which Z is N(R$^{31}$)SO$_2$R$^{30}$ are preferably those whose Methoxy Analog or Propargyloxy Analog is a herbicide. The term "Methoxy Analog" is used here to designate a compound which is otherwise identical except that it has a methoxy group instead of the

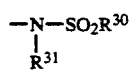

group of said compound. The term "Propargyloxy Analog" is similarly used here for a compound which is otherwise identical except that it has a propargyloxy group instead of the

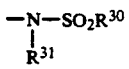

group of said compound.

The compounds in which Z is N(R³¹)SO₂R³⁰ preferably have Methoxy Analogs and Propargyloxy Analogs of marked herbicidal properties. For instance at least one (and preferably both) of said Analogs of each of those preferred compounds shows at least 50% kill of at least one of the following species of plants when applied under at least one of the following modes at the rate of 0.5 kg/ha, and more preferably shows such kill of at least 50% when applied at the rate of 0.1 kg/ha: Species: velvetleaf (*Abutilon theophrasti*), green foxtail (*Setaria viridis*); Modes: pre-emergent, post-emergent. Testing for such herbicidal activity may be carried out in the manner described below (under the heading "Herbicidal Activity").

Z is $SO_2R^{16}$ $R^{16}$ is hydrogen, amino, alkylamino or dialkylamino in which each alkyl is preferably of 1 to 4 carbon atoms, or arylamino in which aryl is unsubstituted phenyl or phenyl substituted with halogen (such as fluorine or chlorine) or alkyl (preferably of 1 to 4 carbon atoms such as methyl).

Examples of Z groups for this embodiment include $SO_2H$, $SO_2NH_2$, $SO_2$, $NHCH_3$, $SO_2N(C_2H_5)_2$, $SO_2N(CH_3)(C_2H_5)$, $SO_2NHCH(CH_3)_2$, $SO_2NHC_6H_5$, $SO_2NHC_6H_4(4-Cl)$, and $SO_2NHC_6H_4(4-CH_3)$.

Z is $CO-R^{17}$ $R^{17}$ is hydroxy, alkoxy or alkylthio (preferably of 1 to 4 carbo atoms), amino, akylamino or dialkylamino in which each alkyl is preferably of 1 to 4 carbon atoms, or arylamino in which aryl is unsubstituted phenyl or phenyl substituted with halogen (such as fluorine or chlorine) or alkyl (preferably of 1 to 4 carbon atoms such as methyl). Acid salts (same as above) are also useful.

Examples of Z groups for this embodiment include $CO_2H$, $CO_2CH_3$, $CO_2CH(CH_3)_2$, $CO-SCH_3$, $CONH_2$, $CONHCH_3$, $CON(C_2H_5)_2$, $CON(CH_3)(C_2H_5)$, $CONHCH(CH_3)_2$, $CONHC_6H_5$, $CONHC_6H_4(4-Cl)$, and $CONHC_6H_4(4-CH_3)$.

For each of the Z substituents described above, a preferred embodiment comprises the compounds in which W is oxygen, R is n-propyl or, particularly, a fluoropropyl such as 3-fluoropropyl, $X^1$ is chlorine or, especially, fluorine, and $X^2$ is chlorine or bromine. The compounds in which Z is $OR^1$ have very high herbicidal activity, especially where $R^1$ is 2-propynyl (or a 3-halo-2-propynyl such as 3-iodo- or bromo-2-propynyl).

Any free acid compound of formula I may be converted into a salt such as a sodium, potassium, calcium, ammonium, magnesium, or mono-, di- or tri(C₁ to C₄ alkyl)ammonium salt which may also be used as an herbicide.

An additional aspect of the present invention pertains to the discovery that the herbicidal compounds of the invention also have fungicidal properties. Thus, use of the present compounds as herbicides give the incidental benefit of fungus disease control, prevention or moderation, particularly with respect to rice blast. Compound 4' of Table 1' is a preferred embodiment for this aspect of the invention.

Compound 4' gave 57% rice blast control at an application rate of 0.0078 kg/ha; rice plant injury (phytotoxicity) was 30%. It was inactive against the rice blast at 0.002 kg/ha. The testing procedure is given below under the heading "Rice Blast Testing Procedure".

Many of the present herbicidal compounds may be prepared by the methods illustrated in the chemical equations below.

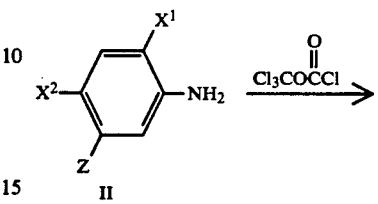

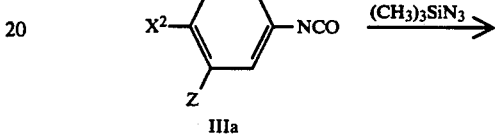

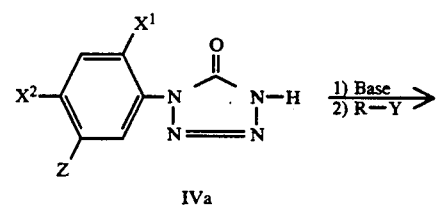

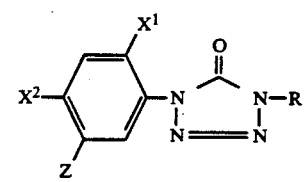

Treatment of an appropriately substituted phenylamine, II, with trichloromethyl chloroformate gives the corresponding isocyanate IIIa, which upon treatment with trimethylsilyl azide in the manner of O. Tsuge et al., *J. Org. Chem.*, 45, 5130 (1980), incorporated herein by reference, affords the intermediate tetrazolinone IVa. Intermediate IVa may also be prepared by treatment of the isocyanate IIIa with aluminum azide in the manner of J. Horwitz et al., *J. Am. Chem. Soc.*, 81, 3076 (1959), incorporated herein by reference. Treatment of the N-4 unsubstituted tetrazolinone IVa with R-Y, wherein Y is a good leaving group, in the presence of a base gives compound Ia. The leaving group Y will generally be a chlorine, bromine, or iodine atom, but may be any readily displaceable group used in the art in similar reactions such as a mesylate group. The use of sodium hydride base in dimethylformamide has been found to give satisfactory results. This method is generally useful where compound II is readily available, either commercially or by preparation, and is particularly useful where Z is hydrogen, halogen, cyano alkyl, substituted alkyl, or $-OR^1$ wherein $R^1$ is alkyl, especially lower alkyl such as methyl, or benzyl (a useful intermediate discussed below).

The corresponding thiones Ib (I, W is sulfur) may be prepared in a similar manner by treating the appropriately substituted phenylamine II with thiophosgene in the presence of triethylamine to give corresponding isothiocyanate (IIIb) and treating that first with sodium azide and water, then with acid (e.g. HCl/H₂O) to give the thione (IVb) which may be concerted by reaction with R-Y (as above for IVa) to the thione (Ib).

In some instances the desired Z group may be unstable under the conditions used in preparing II or in converting II into I. In such cases or where it is otherwise not desirable or convenient to proceed by the methods outlined above, it may be advantageous to add the desired Z substituent to the molecule subsequent to the addition of the desired R group (or a group that can be subsequently converted into the desired R group). In such cases a useful and versatile intermediate is compound I in which Z is —QH (the 5-hydroxyphenyl compound, V, or the corresponding 5-mercaptophenyl compound, VI).

Compound V (Z is OH) is readily prepared from the corresponding compound I in which Z is a lower alkoxy group or a benzyloxy group by treatment with an acidic reagent such as concentrated sulfuric acid, concentrated hydrobromic acid, or a mixture of hydrobromic and acetic acids to effect dealkylation, or, where Z is benzyloxy, by hydrogenolysis over palladium on charcoal (H₂/Pd/C/C₂H₅OH).

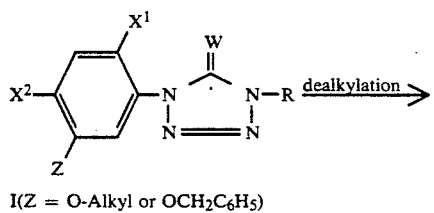

I(Z = O-Alkyl or OCH₂C₆H₅)

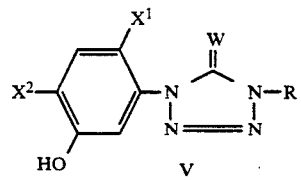

The 5-mercaptophenyl compound (VI) may be prepared from the corresponding compound in which Z is hydrogen by the following sequence of steps: nitration (e.g. HNO₃/H₂SO₄) to give the corresponding 5—NO₂ compound (I, Z is NO₂), reduction (e.g. H₂/PTO₂/C₂H₅OH) to give the corresponding 5—NH₂ compound (I, Z is NH₂), treatment first with NaNO₂/HCl then with SO₂/CuCl to give the corresponding 5—SO₂Cl compound (I, Z is SO₂Cl), and, finally, reduction (e.g. Sn/HCl) to give the 5—SH compound VI (I, Z is SH).

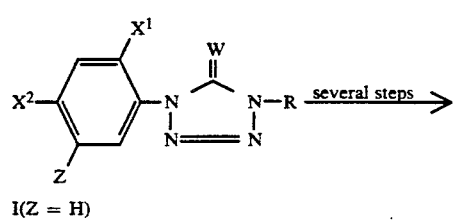

I(Z = H)

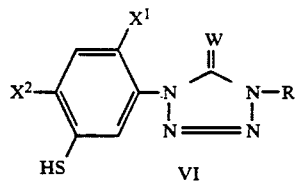

The appropriate compound V (I, Z=OH) or compound VI (I, Z=SH) is then treated in the presence of a base with the appropriate Y—R¹, Y—SO₂R², Y—R⁷—CO—QR⁸(R⁸≠H), Y—R⁷—CO₂—N=C(R⁹)(R¹⁰), or Y—R⁷—C(CH₃)=R¹¹, wherein Y is a good leaving group, to give compound I in which Z is —QR¹, OSO₂R², —QR⁷CO—QR⁸(R⁸≠H), —QR⁷CO₂N=C(R⁹)(R¹⁰), or —QR⁷C(CH₃)=R¹¹.

Alternatively, compounds of formula I in which Z is —QR⁷—CO—SR⁸ or —QR⁷CO₂N=C(R⁹)(R¹⁰) may be prepared from the corresponding compound in which Z is —QR⁷CO₂R⁸ (ester, prepared as described above) by hydrolysis to the acid (Z is —QR⁷CO H), followed by conversion to the acid chloride (Z is —QR⁷COCl), then either by treatment with R⁸SH to give I in which Z is —QR⁷—CO—SR⁸ or by treatment with (R⁹(R¹⁰)C=N—OH to give I in which Z is —QR⁷CO₂N=C(R⁹)(R¹⁰).

Similarly, compounds of formula I in which Z is —QR⁷CON(R¹²)(R¹³) may be prepared from the corresponding compound in which Z is —QR⁷COCl (prepared as described above) by treatment HN(R¹²)(R¹³).

An alternative method for preparing the compounds of formula I in which Z is —QR⁷C(CH₃)=R¹¹ wherein R¹¹ is N—OR²⁰ is by reacting the corresponding compound in which R¹¹ is oxygen (prepared as described above) with H₂N—OR²⁰.

In the conversion of V or VI into I described above, the base and the leaving group Y may be selected from those used in the art for similar reactions. The leaving group Y in R²SO₂Y will usually be chlorine or bromine. Examples of suitable bases for the reaction with R²SO₂Y are sodium hydride and triethylamine. For R¹—Y, Y will generally be chlorine, bromine, iodine, or 4-methylphenylsulfonyloxy. Suitable bases include sodium hydride and, where Y is bromine, chlorine, or iodine, potassium carbonate and potassium fluoride.

Compound I in which Z is SO₂R¹⁶ may be prepared from the corresponding compound in which Z is SO₂Cl (prepared as described above) by treatment with water (R¹⁶ is hydroxy), ammonia (R¹⁶ is NH₂) or an appropriate amine (R¹⁶ is alkylamino, dialkylamino, or arylamino).

Compounds of formula I in which Z is cyano (which may be prepared as described above from II) are useful intermediates for the corresponding compounds in which Z is —CO—R⁷ by hydrolysis followed by estrification or amide formation as the case may be.

Compounds of formula I in which Z is —N(R¹⁴)(R¹⁵) may be prepared by reduction of the corresponding nitro compound (Z=NO₂, prepared as described above) to give the amino derivative (Z=NH₂, discussed above) followed by appropriate alkylation, acylation, or sulfonylation as the case may be. The amino compound may also be converted into the corresponding isocyanate (Z=NCO) by treatment with trichloromethyl chloroformate. Treatment of the isocyanate (Z=NCO) with an appropriate amine gives the corresponding compound in which Z is —N(R$^{14}$)(R$^{15}$) and one of R$^{14}$ and R$^{15}$ is hydrogen and the other is aminocarbonyl, alkylaminocarbonyl or dialkylaminocarbonyl. The amino compound (Z=NH$_2$) may also be used to prepare the compounds in which N(R$^{14}$)(R$^{15}$) is the group N=C(R$^9$)(R$^{10}$) (by treatment with R$^9$R$^{10}$C=O or a cyclic group such as a tetrahydrophthalimido (by treatment with tetrahydrophthalic anhydride).

Compounds of formula I in which Z and X$^1$ are halogen atoms and X$^2$ is nitro may be prepared by nitration (e.g. HNO$_3$/H$_2$SO$_4$) of the corresponding compound in which X$^2$ is hydrogen (e.g. compound 226 in the tables is converted by nitration to compound 217). The Z halogen in the nitro compounds (Z and X$^1$ are halogen, X$^2$ is nitro) may be readily displaced to produce other herbicidal compounds of the invention, for example, by reaction with R$^1$—OH in the presence of a base (e.g. NaH) to give the corresponding compound in which Z is —OR$^1$.

Certain of the present compounds may be prepared from intermediate V by the method illustrated in the following chemical equation.

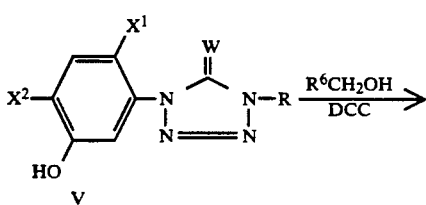

The moiety R$^6$CH$_2$ represents appropriate R$^1$ substituents. The reaction is conducted in the presence of a dehydration reagent such as dicyclohexylcarbodiimide (DCC).

Where R$^1$ is a saturated oxygen- or sulfur-containing heterocycle, a further method of preparation involves addition of the hydroxy group of V or the mercapto group of VI across the double bond of a dihydroheterocycle as shown in the equation below for 2-tetrahydrofuranyl.

The compounds in which R is a difluoroalkyl radical in which both fluorine atoms are on the same carbon atom such as —(CH$_2$)$_2$CHF$_2$ or —CH$_2$CH$_3$ may be prepared from the corresponding aldehyde or ketone (e.g. —CH$_2$CH$_2$CHO or —CH$_2$COCH$_3$) by treatment with diethylaminosulfur trifluoride (ET$_2$N—SF$_3$, "DAST") in the presence of methylene chloride.

The methods described above and in the examples for preparing compound I, and intermediates therefor, comprise a further aspect of the present invention.

An additional aspect of the invention pertains to the intermediates themselves, particularly compounds IV, V, VI, and VII.

V (Z = OH)
VI (Z = SH)
VII (Z = OCH$_2$C$_6$H$_5$)

With respect to compound IV, W is sulfur or, preferably, oxygen, one of X$^1$ and X$^2$ is fluorine, chlorine, or bromine and the other is fluorine, chlorine, bromine, alkyl (preferably of 1 to 6 carbon atoms, more preferably of 1 to 4, carbon atoms) such as methyl, or haloalkyl (preferably of 1 to 5 carbon atoms) particularly fluoromethyl, trifluoromethyl, or bromomethyl, (or X$^2$ may be NO2 when X$^1$ is F, Cl, or Br), and Z is hydrogen, fluorine, chlorine, bromine, cyano, nitro, alkyl (preferably of 1 to 6 carbon atoms) such as methyl, haloalkyl (preferably of 1 to 5 carbon atoms) such as trifluoromethyl, alkynyl (preferably of 3 to 5 carbon atoms), or QR$^1$ in which Q is sulfur or, preferably, oxygen and R$^1$ is alkyl (preferably of 1 to 6, more preferably of 1 to 4, carbon atoms), haloalkyl (preferably of 1 to 5 carbon atoms), particularly a fluoroalkyl, cyanoalkyl (preferably of 1 to 5 alkyl carbon atoms), alkoxyalkyl (preferably of 2 to 6 carbon atoms), alkylthioalkyl, alkylsulfinylalkyl, or alkylsulfonylalkyl (each preferably of 2 to 6 carbon atoms), alkenyl (preferably of 2 to 5, more preferably of 3 to 5, carbon atoms), haloalkenyl (preferably of 2 to 5, more preferably of 3 to 5, carbon atoms) such as a halo-2-propenyl, alkenyloxyalkyl (preferably of 3 to 6 carbon atoms), alkynyl (preferably of 2 to 5, more preferably 3 to 5, carbon atoms) or haloalkynyl (preferably of 2 to 5, more preferably 3 to 5, carbon atoms). $R^1$ is advantageously benzyl or lower alkyl.

With respect to compounds V, VI, and VII, W, $X^1$, and $X^2$ are as defined above for compound IV and R is alkyl (preferably of 1 to 6 carbon atoms), fluoroalkyl (preferably of 1 to 5 carbon atoms), alkoxyalkyl (preferably of 2 to 6 carbon atoms), alkylthioalkyl (preferably of 2 to 6 carbon atoms), cyanoalkyl (preferably of 1 to 5 alkyl carbon atoms), haloalkyoxyalkyl (preferably of 2 to 6 carbon atoms), trifluoromethylthio, alkenyl (preferably of 2 to 5 carbon atoms), 2-oxopropyl, 3-oxopropyl, or haloalkenyl (preferably of 2 to 5 carbon atoms). Preferably R is n—$C_3H_7$ or, particularly, a fluoroalkyl such as 3-fluoropropyl.

The compounds in which Z is $N(R^{31})SO_2R^{30}$ may be prepared by the use of steps generally described in the literature or by methods analogous or similar thereto and within the skill of the art. In the Examples below an arylamine is treated to form the corresponding aryl isocyanate whose isocyanate portion is then modified to form a tetrazolinone ring. Thereafter the benzene ring of the intermediate is nitrated, the nitro group is reduced to form an amino group, which is then treated with $R^{30}SO_2Cl$ to convert it to an —$N(SO_2R^{30})_2$ group. This may then be treated (as with a base such as NaOH) to form the corresponding —$NR^{31}SO_2R^{30}$ group, where $R^{31}$ is a salt-forming group (e.g. Na); this may then be treated with an acid to form the corresponding (acidic) —$NHSO_2R^{30}$ group. Subsequent alkylation (as by treatment with the appropriate alkyl iodide forms the corresponding

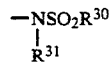

group. When the reaction sequence involves $R^{30}SO_2Cl$ treatment of an intermediate having hydrogen on the 4-nitrogen of the tetrazolinone ring, that hydrogen may also be replaced, during such treatment, by $R^{30}SO_2$— to form an intermediate (such as a compound which has 3 $R^{30}SO_2$— groups) from which the $R^{30}SO_2$— group on said 4-nitrogen may be removed readily by the treatment with the base, after which the appropriate R group may be substituted on said 4-nitrogen.

The sequence of steps may be changed. For instance one may start with a nitroaniline, such as 3-nitroaniline or 2-fluoro-5-nitroaniline, then make the corresponding isocyanate and convert the isocyanate group to a tetrazolinone ring (as by treatment with trimethylsilylazide) and then reduce the nitro group and substitute an R group on N-4 of the tetrazolinone ring, in either order. Thereafter the amino group may be converted to a $N(R^{31})SO_2R^{30}$ group, after which the compound may be halogenated (as with $SO_2Cl_2$ in dioxan) to place a halogen at the 4-position of the benzene ring (or, when the intermediate being halogenated does not yet have the halogen on its 2-position, this halogenation may place halogen atoms at both the 2- and 4-positions of the benzene ring). Thus the following series of successive intermediates may be prepared from 2-fluoro-5-nitroaniline:

2-fluoro-5-nitrophenyl isocyanate
1-(2-fluoro-5-nitrophenyl)-1,4-dihydro-5H-tetrazol-5-one;
1-(2-fluoro-5-aminophenyl)-1,4-dihydro-5H-tetrazol-5-one; or 1-(2-fluoro-5-nitrophenyl)-1,4-dihydro-4-(3-fluoropropyl)-5H-tetrazol-5-one;
1-(2-fluoro-5-aminophenyl)-1,4-dihydro-4-(3-fluoropropyl)-5H-tetrazol-5-one;
1-[2-fluoro-5-(bis(N-ethylsulfonyl)amino)phenyl]-1,4-dihydro-4-(3-fluoropropyl-5H-tetrazol-5-one;
1-[2-fluoro-5-(ethylsulfonylamino)phenyl]-1,4-dihydro-4-(3-fluoropropyl)-5H-tetrazol-5-one.

When the starting material is 3-nirophenylaniline, the corresponding intermediates without the 2-fluoro substituent may be formed, and the last intermediate may then be treated to place the halogens at its 2- and 4-positions of its benzene ring.

Representative compounds of the invention are shown in Tables 1 and 1'. Characterizing data for many of the compounds are given in Table 2 and 2'.

The preparation and herbicidal activity of representative compounds of this invention are illustrated further in the examples below. All temperatures are in degrees Celsius, and all pressures are in mm Hg.

EXAMPLE 1

1,4-Dihydro-4-propyl-1-(2,4,5-trichlorophenyl)-5H-tetrazol-5-one

Step A: 1,4-Dihydro-1-(2,4,5-trichlorophenyl)-5H-tetrazol-5-one

In a manner similar to that disclosed by Tsuge et al., *J. Org. Chem.*, 45, 5230 (1980), the reaction of 6.2 g (0.028 mole) of 2,4,5-trichlorophenyl isocyanate and 6.4 g (0.056 mole) of trimethylsilyl azide produced 1,4-dihydro-1-(2,4,5-trichlorophenyl)-5H-tetrazol-5-one as a solid, 175°–176° C.

The nmr and ir spectra were consistent with the proposed structure.

Analysis calc'd for $C_7H_3Cl_3N_4O$: C 31.66; H 1.14; N 21.10; Found: C 34.78; H 1.62; N 18.02.

Step B: 1,4-Dihydro-4-propyl-1-(2,4,5-trichlorophenyl)-5H-tetrazol-5-one

To a stirred mixture of 0.24 g (0.005 mole) of sodium hydride (60% oil suspension) in 45 mL of N,N-dimethylformamide was added 1.3 g (0.005 mole) of 1,4-dihydro-1-(2,4,5-trichlorophenyl)-5H-tetrazol-5-one. The mixture was stirred at room temperature for 15 minutes, then 0.85 g (0.005 mole) of 1-iodopropane and several drops of 1,4,7,10,13,16-hexaoxacyclooctadecane (18-crown-6) were added. After complete addition, the reaction mixture was stirred at room temperature for 4 days. The reaction mixture was poured into ice water and the resulting mixture extracted with diethyl ether. The ether extract was dried over anhydrous magnesium sulfate, filtered, and the filtrate evaporated under reduced pressure to leave a solid. The solid was purified by column chromatography on silica gel, eluting with methylene chloride. Recrystallization from ethanol gave 0.3 g of 1,4-dihydro-4-propyl-1-(2,4,5-trichlorophenyl)-5H-tetrazol-5-one as a solid, mp 89°–90° C.

The nmr and ir spectra were consistent with the proposed structure.

The tetrazolinone of Example 1 is listed in Table 1 as compound 1. Compounds 2, 3 and 109–114 were prepared by an analagous method.

EXAMPLE 2

1-(2,4-Dichloro-5-methylphenyl)-1,4-dihydro-4-propyl-5H-tetrazol-5-one

Step A: 3-Acetamidotoluene

Acetic anhydride (176 mL) was added slowly to a stirred mixture of 103.2 mL of m-toluidine in 300 mL of water. After complete addition, the mixture was stirred for 4 hours at room temperature. The mixture was cooled in an ice bath, then extracted with diethyl ether. The ether extract was dried over anhydrous sodium sulfate, filtered, and the filtrate evaporated under reduced pressure to leave an oily residue which solidified. The solid was collected, washed with water, then dissolved in diethyl ether. The etheral solution was dried over anhydrous sodium sulfate, filtered, and the filtrate evaporated under reduced pressure to yield 3-acetamidotoluene as a solid, mp 59°-61° C.

Step B: 2,4-Dichloro-5-methylacetanilide

Sulfuryl chloride (120 mL) was added dropwise to 75.0 g (0.05 mole) of 3-acetamidotoluene with stirring. After complete addition, the reaction mixture became solid and was allowed to stand at room temperature for approximately 60 hours. The solid mixture was heated until a slurry formed, then stirred for approximately 5 hours. The mixture was cooled to room temperature and treated with ice water and methylene chloride. The resulting two-phase mixture was filtered, and the organic phase was separated, dried over anhydrous sodium sulfate, then filtered. The solvent was evaporated from the filtrate under reduced pressure to leave a solid. The solid was purified by recrystallization from ethyl acetate to yield 10.5 g of 2,4-dichloro-5-methylacetanilide, mp 133°-135° C.

Step C: 2,4-Dichloro-5-methylaniline

A solution of 3.7 g (0.09 mole) of sodium hydroxide in 96 mL of water was added to a stirred suspension of 9.0 g (0.0041 mole) of 2,4-dichloro-5-methylacetanilide in 96 mL of ethanol. After complete addition, the reaction mixture was heated at reflux for 2 hours. The reaction mixture was cooled, diluted with 200 mL of water, and the resultant mixture stirred at room temperature for approximately 60 hours. A precipitate had formed and was collected by filtration and purified by recrystallization from ethyl acetate to yield 4.0 g of 2,4-dichloro-5-methylaniline.

Step D: 2,4-Dichloro-5-methylphenyl isocyanate

In a manner similar to Kurita, et al., *J. Org. Chem.*, 41, 2070 (1976), incorporated herein by reference, the reaction of 3.43 g (0.0156 mole) of 2,4-dichloro-5-methylaniline and 3.5 g (0.018 mole) of trichloromethyl chloroformate in 50 mL of toluene produced 3.4 g of 2,4-dichloro-5-methylphenyl isocyanate.

Step E: 1-[2,4-Dichloro-5-methylphenyl)-1,4-dihydro-5H-tetrazol-5-one

In the manner of Example 1, Step A, the reaction of 3.4 g (0.016 mole) of 2,4-dichloro-5-methylphenyl isocyanate and 3.6 g (0.031 mole) of trimethylsilyl azide produced 1.07 g of 1-(2,4-dichloro-5-methylphenyl)-1,4-dihydro-5H-tetrazol-5-one as a solid, mp 135°-137° C.

The nmr and ir spectra were consistent with the proposed structure.

Step F: 1-(2,4-Dichloro-5-methylphenyl)-1,4-dihydro-4-propyl-5H-tetrazol-5-one

Under a dry nitrogen atmosphere, 0.06 g (0.0012 mole) of sodium hydride (50% oil suspension) was washed with petroleum ether to remove the oil, then suspended in 5 mL of anhydrous N,N-dimethylformamide. To the suspension was added 0.3 g (0.0012 mole) of 1-(2,4-dichloro-5-methylphenyl)-1,4-dihydro-4H-tetrazol-5-one. After complete addition, the mixture was stirred at room temperature for 30 minutes then heated at 60° C. for 15 minutes. The mixture was cooled to room temperature and 0.4 g (0.0024 mole) of 1-iodopropane added. The resultant mixture was stirred at room temperature for approximately 60 hours then poured into ice water. The mixture was extracted with ethyl acetate and the organic phase washed with a saturated aqueous solution of sodium chloride. The organic phase was dried over anhydrous sodium sulfate, filtered, and the filtrate evaporated to leave an oil. The oil was purified by column chromatography on silica gel, eluting with ethyl acetate:n-hexane (15:85), to yield 0.12 g of 1-(2,4-dichloro-5-methylphenyl)-1,4-dihydro-4-propyl-5H-tetrazol-5-one as a solid, mp 47°-48° C.

The nmr and ir spectra were consistent with the proposed structure.

The tetrazolinone prepared in Example 2 is listed as compound 4 in Table 1. Compounds 5 and 90 were prepared by a similar method starting from the appropriately substituted aniline.

EXAMPLE 3

1-(2,4-Dichloro-5-methoxyphenyl)-1,4-dihydro-4-methyl-5H-tetrazol-5-one

Step A: 3-Hydroxyacetanilide

In the manner of Example 2, Step A, the reaction of 66.0 g (0.60 mole) of 3-aminophenol and 77.8 g (0.76 mole) of acetic anhydride in 180 mL of water gave 81.0 g of 3-hydroxyacetanilide as a solid, mp 144°-146.C. The reaction was repeated to obtain an additional quantity of product.

Step B: 2,4-Dichloro-5-hydroxyacetanilide

In the manner of Example 2, Step B, the chlorination of 100.0 g (0.66 mole) of 3-hydroxyacetanilide with 179.8 g (1.33 mole) of sulfuryl chloride in 1570 mL of glacial acetic acid produced 63.5 g of 2,4-dichloro-5-hydroxyacetanilide as a solid, mp 224°-226° C.

Step C: 2,4-Dichloro-5-methoxyacetanilide

A stirred mixture of 35.0 g (0.16 mole) of 2,4-dichloro-5-hydroxyacetanilide, 33.1 g (0.24 mole) of potassium carbonate, and 34.1 g (0.24 mole) of methyl iodide in 300 mL of acetone was heated at reflux for approximately 18 hours. The mixture was cooled and filtered. The filtrate was evaporated under reduced pressure to leave 37.4 g of 2,4-dichloro-5-methoxyacetanilide as a solid.

Step D: 2,4-Dichloro-5-methoxyaniline

In the manner of Example 2, Step C, the reaction of 37.4 g (0.16 mole) of 2,4-dichloro-5-methoxyacetanilide with 12.8 g (0.32 mole) of sodium hydroxide in 30 mL of water and 30 mL of ethanol produced 16.7 g of 2,4-dichloro-5-methoxyaniline.

1-(2,4-Dichloro-5-methoxyphenyl)-1,4-dihydro-4-methyl-5H-tetrazol-5-one (compound 6) and compounds 7, 9 and 14–20 of Table 1 were prepared from 2,4-dichloro-5-methoxyaniline using the method described in Steps D, E and F of Example 2. Compounds 21–27, 30, 37, 73, 77, 100 and 101 were also prepared by the method of Example 2, Steps D, E, and F from the corresponding 2,4-dichloro-5-alkoxyaniline compounds which were prepared in the manner of Example 3.

EXAMPLE 4

1-(2,4-Difluoro-5-methoxyphenyl)-1,4-dihydro-4-ethyl-5H-tetrazol-5-one

Step A: 2,4-Difluoro-5-methoxyaniline

Hydrogenation of 3.0 g (0.017 mole) of 2,4-difluoro-5-methoxy-1-nitrobenzene in the presence of 0.1 g of platinum oxide and 0.3 mL of morpholine in 110 mL of absolute ethanol produced 1.5 g of 2,4-difluoro-5-methoxyaniline as a solid, mp 43°–45° C.

The nmr and ir spectra were consistent with the proposed structure.

1-(2,4-Dichloro-5-methoxyphenyl)-1,4-dihydro-4-methyl-5H-tetrazol-5-one (compound 8) and compound 10 of Table 1 were prepared from 2,4-difluoro-5-methoxyaniline by the method of Example 2, Steps D, E, and F.

EXAMPLE 5

1-(4-Chloro-2-fluoro-5-methoxyphenyl)-1,4-dihydro-4-propyl-5H-tetrazol-5-one Step A: 2-Chloro-4-fluorophenyl 4-methylphenylsulfonate A stirred solution of 20.0 g (0.137 mole) of 2-chloro-4-fluorophenol in 150 mL of pyridine was cooled in an ice bath. To this solution was added portionwise 31.2 g (0.164 mole) of 4-methylphenylsulfonyl chloride. After complete addition, the mixture was stirred for 2 hours, then allowed to stand in a freezer for approximately 16 hours. The mixture was poured into ice water, filtered, and the filter cake washed with water. The solid was dried in a dessicator to yield 41.0 g of 2-chloro-4-fluorophenyl 4-methylphenylsulfonate, mp 92°–94° C.

Step B: 2-Chloro-4-fluoro-5-nitrophenyl 4-methyl-3-nitrophenylsulfonate

Nitration of 41.0 g (0.16 mole) of 2-chloro-4-fluorophenyl 4-methylphenylsulfonate in 340 mL of fuming nitric acid produced a solid which was recrystallized from ethanol to yield 40.0 g of 2-chloro-4-fluoro-5-nitrophenyl 4-methyl-3-nitrophenylsulfonate.

Step C: 2-Chloro-4-fluoro-5-nitrophenol

A solution of 12.84 g (0.195 mole) of potassium hydroxide in 200 mL of water was added to a vigorously stirred solution of 34.0 g (0.097 mole) of 2-chloro-4-fluoro-5-nitrophenyl 4-methyl-3-nitrophenylsulfonate in 190 mL of p-dioxane. The resultant mixture was stirred at room temperature for approximately 18 hours. The reaction mixture was filtered and the filtrate acidified with concentrated hydrochloric acid. The acidic solution was extracted with diethyl ether. The ether extract was dried over anhydrous sodium sulfate, filtered, and the solvent evaporated under reduced pressure to leave a solid. The solid was washed with petroleum ether to yield 15.07 g of 2-chloro-4-fluoro-5-nitrophenol.

Step D: 1-Chloro-5-fluoro-2-methoxy-4-nitrobenzene

To a stirred solution of 8.0 g (0.042 mole) of 2-chloro-4-fluoro-5-nitrophenol in 200 mL of acetone was added 6.09 g (0.0435 mole) of potassium carbonate. The mixture was heated at reflux temperature for 15 minutes, and 8.9 g (0.063 mole) of iodomethane was added. The resultant mixture was heated at reflux temperature for 5 hours, then stirred at room temperature for approximately 18 hours. The mixture was filtered and the filtrate evaporated under reduced pressure to leave a residue. The residue was dissolved in diethyl ether, filtered, and the filtrate washed with a saturated sodium chloride solution. The ether solution was dried over anhydrous sodium sulfate, filtered, and the filtrate evaporated to yield 6.6 g of 1-chloro-5-fluoro-2-methoxy-4-nitrobenzene as a solid, 63°–65° C.

The nmr spectrum was consistent with the proposed structure.

Step E: 4-Chloro-2-fluoro-5-methoxyaniline

Hydrogenation of 6.6 g (0.032 mole) of 1-chloro-5-fluoro-2-methoxy-4-nitrobenzene in the presence of 0.2 g of platinum oxide and 0.7 g (0.008 mole) of pyridine in 200 mL of absolute ethanol produced 6.5 g of 4-chloro-2-fluoro-5-methoxyaniline.

1-(4-Chloro-2-fluoro-5-methoxyphenyl)-1,4-dihydro-4-propyl-5H-tetrazol-5-one (compound 11) was prepared by the method described in Example 2, Steps D, E, and F from 4-chloro-2-fluoro-5-methoxyaniline.

EXAMPLE 6

1-(4-Bromo-2-chloro-5-methoxyphenyl)-1,4-dihydro-4-propyl-5H-tetrazol-5-one

Step A: 4-Bromo-2-chloro-5-methoxyaniline

A stirred solution of 9.7 g (0.050 mole) of 2-chloro-5-methoxyaniline hydrochloride in 120 mL of acetic acid was cooled to 15° C. To this cold mixture was added 4.0 g (0.025 mole) of bromine. After complete addition, the mixture was allowed to warm to room temperature and was stirred for approximately 18 hours. The mixture was poured into ice water. To the resultant mixture was added a solution of 2.0 g (0.05 mole) of sodium hydroxide in 10 mL of water. This mixture was extracted with 200 mL of diethyl ether. The ether extract was dried over anhydrous magnesium sulfate, filtered, and the filtrate evaporated under reduced pressure to leave an oil. The oil was purified by column chromatography on silica gel, eluting with methylene chloride, to yield 7.3 g of 4-bromo-2-chloro-5-methoxyaniline as a solid, mp 40°–41° C.

1-(4-Bromo-2-chloro-5-methoxyphenyl)-1,4-dihydro-4-propyl-5H-tetrazol-5-one (compound 12) was prepared from 4-bromo-2-chloro-5-methoxyaniline by the method of Example 2, Steps D, E, and F.

EXAMPLE 7

1-(2-Bromo-4chloro-5-methoxyphenyl)-1,4-dihydro-4-propyl-5H-tetrazol-5-one

Step A: 5-Methoxyacetanilide

In the manner of Example 2, Step A, the reaction of 103.1 g (0.837 mole) of 3-methoxyaniline and 170.5 g (1.67 moles) of acetic anhydride in 300 mL of water produced 138.0 g of 5-methoxyacetanilide as a solid, mp 60°–62° C.

Step B: 4-Chloro-5-methoxyacetanilide

In the manner of Example 2, Step B, the reaction of 50.0 g (0.303 mole) of 5-methoxyacetanilide with 40.9 g (0.303 mole) of sulfuryl chloride in 300 mL of chloroform produced a solid. The solid was triturated in ethyl acetate:n-hexane and collected on a filter paper to give 17.0 g of a solid. Recrystallization from ethyl acetate:n-hexane provided 4.3 g of 4-chloro-5-methoxyacetanilide, mp 83°–85° C.

The nmr spectrum was consistent with the proposed structure.

Step C: 2-Bromo-4-chloro-5-methoxyacetanilide

Bromination of 4.0 g (0.03 mole) of 4-chloro-5-methoxyacetanilide with 3.2 g (0.02 mole) of bromine in 50 mL of glacial acetic acid produced 3.9 g of 2-bromo- 4-chloro-5-methoxyacetanilide as a solid, mp 143°–145° C.

The nmr spectrum was consistent with the proposed structure.

Step D: 2-Bromo-4-chloro-5-methoxyaniline

In the manner of Example 2, Step C, the reaction of 3.9 g (0.013 mole) of 2-bromo-4-chloro-5-methoxyacetanilide with 1.13 g (0.028 mole) of sodium hydroxide in 30 mL of water and 25 mL of ethanol produced 2.9 g of 2-bromo-4-chloro-5-methoxyaniline.

The nmr and ir spectra were consistent with the proposed structure.

1-(2-Bromo-4-chloro-5-methoxyphenyl)-1,4-dihydro-4-propyl-5H-tetrazol-5-one (compound 13) was prepared from 2-bromo-4-chloro-5-methoxyaniline using the method of Example 2, Steps D, E, and F.

EXAMPLE 8

1-[2,4-Dibromo-5-(1-methylethoxy)phenyl]-1,4-dihydro-4-(2-propenyl)-5H-tetrazol-5-one Step A: 2,4-Dibromo-5-hydroxyacetanilide Using the method of Example 6, the bromination of 30.2 g (0.20 mole) of 3-hydroxyacetanilide (Example 3, Step A) with 32 g (0.20 mole) of bromine in 100 mL of glacial acetic acid produced a solid. The solid was treated with an additional 32.0 g (0.20 mole) of bromine in 400 mL of glacial acetic acid to yield 12.5 g of 2,4-dibromo-5-hydroxyacetanilide as a solid, mp 233°–240° C.

Step B: 2,4-Dibromo-5-(1-methylethoxy)acetanilide

To a stirred mixture of 12.0 g (0.038 mole) of 2,4-dibromo-5-hydroxyacetanilide in 80 mL of acetone was added 7.0 g (0.050 mole) of potassium carbonate followed by 8.0 g (0.050 mole) of 2-iodopropane. The mixture was heated at reflux temperature for approximately 18 hours, cooled, then filtered. The filtrate was evaporated to leave a solid which was recrystallized from ethanol to produce 11.7 g of 2,4-dibromo-5-(1-methylethoxy)acetanilide, mp 129°–130° C.

Step C: 2,4-Dibromo-5-(1-methylethoxy)aniline

A stirred mixture of 11.7 g (0.038 mole) of 2,4-dibromo-5-(1-methylethoxy)acetanilide in 100 mL of dilute hydrochloric acid was heated at reflux temperature for 30 minutes. The reaction mixture was cooled, filtered, and the filter cake suspended in 100 mL of water. To the aqueous suspension was added 4.0 g (0.038 mole) of sodium carbonate, and the resulting mixture was stirred for approximately 1 hour. The mixture was filtered and the filter cake dried under reduced pressure to yield 6.2 9 of 2,4-dibromo-5-(1-methylethoxy)aniline.

1-[2,4-Dibromo-5-(1-methylethoxy)phenyl]-1,4-dihydro-4-(2-propenyl)-5H-tetrazol-5-one (compound 28) and compound 29 of Table 1 were prepared from 2,4-dibromo-5-(1-methylethoxy)aniline by the method of Example 2, Steps D, E, and F.

EXAMPLE 9

1-(4-Chloro-5-methoxy-2-methylphenyl-1,4-dihydro-4-propyl-5H-tetrazol-5-one

Step A: 1-Methoxy-4-methyl-3-nitrobenzene

In the manner of Example 8, Step C, the reaction of 25.0 g (0.162 mole) of 4-methyl-3-nitrophenol, 23.3 g (0.168 mole) of potassium carbonate, and 34.1 9 (0.24 mole) of methyl iodide produced 26.4 g of 1-methoxy-4-methyl-3-nitrobenzene as an oil.

The nmr spectrum was consistent with the proposed structure.

Step B: 5-Methoxy-2-methylaniline

Hydrogenation of 26.4 g (0.157 mole) of 1-methoxy-4-methyl-3-nitrobenzene in the presence of 0.5 g of platinum oxide in 200 mL of absolute ethanol produced 20.2 g of 5-methoxy-2-methylaniline as a solid, mp 36°–38° C.

The nmr spectrum was consistent with the proposed structure.

Step C: 5-Methoxy-2-methylacetanilide

In the manner of Example 2, Step A, the reaction of 19.4 g (0.14 mole) of 5-methoxy-2-methylaniline with 28.2 g (0.28 mole) of acetic anhydride in 100 mL of water produced 17.1 g of 5-methoxy-2-methylacetanilide as a solid, 68°–70° C.

The nmr spectrum was consistent with the proposed structure.

Step D: 4-Chloro-5-methoxy-2-methylacetanilide

In the manner of Example 2, Step B, the chlorination of 16.0 g (0.089 mole) of 5-methoxy-2-methylacetanilide with 12.0 g (0.089 mole) of sulfuryl chloride in 150 mL of chloroform produced 13.3 g of 4-chloro-5-methoxyacetanilide as a solid, mp 170°–171° C.

The nmr spectrum was consistent with the proposed structure.

Step E: 2-Chloro-5-methoxy-2-methylaniline

In the manner of Example 2, Step C, the reaction of 13.3 g (0.062 mole) of 4-chloro-5-methoxyacetanilide with 5.0 g (0.125 mole) of sodium hydroxide in 125 mL of water and 125 mL of ethanol produced 4.5 g of 2-chloro-5-methoxy-2-methylaniline as a solid, mp 83°–85° C.

1-(4-Chloro-5-methoxy-2-methylphenyl)-1,4-dihydro-4-propyl-5H-tetrazol-5-one (compound 95) and compound 96 of Table 1 were produced from 2-chloro-5-methoxy-2-methylaniline by the method of Example 2, Steps D, E, and F.

EXAMPLE 10

1-[2,4-Dichloro-5-(3-iodo-2-propynyloxy)phenyl]-1,4-dihydro-4-propyl-5H-tetrazol-5-one Step A: 1-(2,4-Dichloro-5-hydroxyphenyl)-1,4-dihydro-4-propyl-5H-tetrazol-5-one A stirred mixture of 2.0 g (0.0066 mole) of 1-(2,4-dichloro-5-methoxyphenyl)-1,4-dihydro-4-propyl-5H-tetrazol-5-one (compound 9) and 30 mL of concentrated hydrobromic acid was heated at reflux temperature for approximately 18 hours. The reaction mixture was cooled, filtered, and the filter cake dissolved in methylene chloride. The methylene chloride solution was evaporated under reduced pressure to leave 1.35 g of 1-(2,4-dichloro-5-hydroxphenyl)-1,4-dihydro-4-propyl-5H-tetrazol-5-one as a solid, mp 125°–128° C.

The nmr structure was consistent with the proposed structure.

Step B: 1-[2,4-Dichloro-5-(2-propynyloxy)phenyl]-1,4-dihydro-4-propyl-5H-tetrazol-5-one To a stirred solution of 0.5 g (0.0017 mole) of 1-(2,4-dichloro-5-hydroxyphenyl)-1,4-dihydro-4-propyl-5H-tetrazone-5-one in 15 mL of anhydrous N,N-dimethylformamide was added 0.11 g (0.0019 mole) of potassium fluoride, several drops of 18-crown-6, and 0.14 g (0.0019 mole) of propargyl chloride. The mixture was stirred at 80° C. for approximately 20 hours, then cooled to room temperature. A portion of the solvent was removed by distillation under reduced pressure, and the remainder of the mixture was poured into water. The aqueous mixture was extracted with ethyl acetate, and the organic layer washed with a saturated aqueous solution of sodium chloride. The organic phase was dried over anhydrous sodium sulfate, filtered, and the filtrate evaporated under reduced pressure to leave a residue. The residue was purified by column chromatography on silica gel, eluting with ethyl acetate: n-hexane (15:85), to yield 0.27 g of 1-[2,4-dichloro-5-(2-propynyloxy)-phenyl]-1,4-dihydro-4-propyl-5H-tetrazol-5-one as a solid, mp 70°-72° C.

The nmr spectrum was consistent with the proposed structure.

This experiment was repeated on a larger scale to obtain additional quantities of 1-[2,4-dichloro-5-(2-propynyloxy)phenyl]-1,4-dihydro-4-propyl-5H-tetrazol-5-one.

The tetrazolinone prepared in Example 10, Steps A and B is listed in Table 1 as compound 45. Other tetrazolinones prepared in a similar manner are compounds 31, 32, 34, 38–42, 45, 46, 49, 50, 57, 58, 63–65, 80 and 91–93. In some instances 18-crown-6 was not used. Also, in some instances, acetone was used as the solvent in place of N,N-dimethylformamide.

Step C: 1-[2,4-Dichloro-5-(3-iodo-2-propynyloxy)-phenyl]-1,4-dihydro-4-propyl-5H-tetrazol-5-one To a cold solution of 0.5 g (0.00153 mole) of 1-[2,4-dichloro-5-(2-propynyloxy)phenyl]-1,4-dihydro-4-propyl-5H-tetrazol-5-one in 20 mL of methanol was added 2 mL of a saturated aqueous solution of sodium hydroxide and an additional 10 mL of methanol. To this mixture was added a solution of 0.39 g (0.00153 mole) of iodine in 5 mL of methanol. After complete addition, the reaction mixture was allowed to warm to room temperature and was stirred for approximately 18 hours. The reaction mixture was filtered and a solid collected. The solid was purified by column chromatography to yield 0.14 g of 1-[2,4-dichloro-5-(3-iodo-2-propynyloxy)phenyl]-1,4-dihydro-4-propyl-5H-tetrazol-5-one as a solid, mp 134°-138° C.

The nmr spectrum was consistent with the proposed structure.

The tetrazolinone prepared in Step C is listed in Table 1 as compound 61.

EXAMPLE 11

1-[2,4-Difluoro-5-(1-methylethoxy)phenyl]-1,4-dihydro-4-propyl-5H-tetrazol-5-one Step A: 1-(2,4-Difluoro-5-hydroxyphenyl)-1,4-dihydro-4-propyl-5H-tetrazol-5-one Under a dry nitrogen atmosphere a stirred solution of 0.18 G (0.00067 mole) of 1-(2,4-difluoro-5-methoxyphenyl)-1,4-dihydro-4-propyl-5H-tetrazol-5-one (compound 10) in 5 mL of methylene chloride was cooled to −40° C. To this cold solution was added dropwise a solution of 0.5 g (0.002 mole) of boron tribromide in 5 mL of methylene chloride. After complete addition, the mixture was allowed to warm to room temperature and was stirred for approximately 70 hours. The mixture was poured into ice water and the two phases separated. The aqueous phase was extracted with methylene chloride. The organic phases were combined, dried over anhydrous sodium sulfate, and filtered. The filtrate was evaporated to leave 0.14 g of 1-(2,4-difluoro-5-hydroxyphenyl)-1,4-dihydro-4-propyl-5H-tetrazol-5-one as a solid, mp 65°-67° C.

The nmr spectrum was consistent with the proposed structure.

This reaction was repeated to obtain additional quantities of product.

Step B: 1-(2,4-Difluoro-5-(1-methylethoxy)phenyl]-1,4-dihydro-4-propyl-5H-tetrazol-5-one A stirred mixture of 0.87 g (0.0034 mole) of 1-(2,4-difluoro-5-hydroxyphenyl)-1,4-dihydro-4-propyl-5H-tetrazol-5-one, 0.7 g (0.0051 mole) of potassium carbonate, and 1.2 g (0.007 mole) of 2-iodopropane in 40 mL of acetone was heated at reflux for approximately 18 hours. The mixture was cooled, filtered, and the solvent evaporated under reduced pressure to leave an oil. The oil was purified by filtration through a small amount of silica gel followed by crystallization from heptane to yield 0.38 g of 1-[2,4-difluoro-5-(1-methylethoxy)-phenyl]-1,4-dihydro-4-propyl-5H-tetrazol-5-one, mp 76.5°-77° C..

The tetrazolinone prepared in Example 11 is listed in Table 1 as compound 35. Other tetrazolinones prepared by this method were compounds 36, 43, 48, 51–53, 55, 56, 59, 60, 67, 74, 75, 78, 83–85 and 97–99. In some cases the intermediate 5-hydroxyphenyl compound was prepared by the method of Example 10, Step A.

EXAMPLE 12

1-[2,4-Dichloro-5-[2-butynyloxy)phenyl]-1,4-dihydro-4-propyl-5H-tetrazol-5-one

To a stirred solution of 0.5 g (0.0017 mole) of 1-(2,4-dichloro-5-hydroxyphenyl)-1,4-dihydro-4-propyl-5H-tetrazol-5-one (Example 10, Step A) and 0.15 g (0.0021 mole) of 2-butyn-1-ol in 5 mL of acetonitrile was added 0.33 g (0.0016 mole) of dicyclohexylcarbodiimide. The reaction mixture was heated at reflux temperature for 4 days, cooled to room temperature, and filtered. The filtrate was washed with 10 mL of a 10% aqueous sodium hydroxide solution, diluted with methylene chloride, and washed with 10 mL of 6N hydrochloric acid. The washed organic phase was dried over anhydrous magnesium sulfate, filtered, and the filtrate evaporated to leave an oil. The oil was purified by column chromatography on silica gel, eluting with ethyl acetate: heptane (20:80), to yield 0.12 g of 1-[2,4-dichloro-5-(2-butynyloxy)phenyl]-1,4-dihydro-4-propyl-5H-tetrazol-5-one as a solid, mp 58°-60° C.

The nmr and ir spectra were consistent with the proposed structure.

The tetrazolinone prepared in Example 12 is listed as compound 62 in Table 1.

EXAMPLE 13

1-(2,4-Dichloro-5-methoxymethoxyphenyl)-1,4-dihydro-4-ethyl-5H-tetrazol-5-one

Step A: 1-(2,4-Dichloro-5-hydroxyphenyl)-1,4-dihydro-4-ethyl-5H-tetrazol-5-one

In the manner of Example 11, Step A, the reaction of 1.56 g (0.0054 mole) of 1-(2,4-dichloro-5-methoxyphenyl)-1,4-dihydro-4-ethyl-5H-tetrazol-5-one (compound 7) and 4.06 g (0.016 mole) of boron tribromide in 20 mL of methylene chloride produced 1.25 g of 1-(2,4-dichloro-5-hydroxyphenyl)-1,4-dihydro-4-ethyl-5H-tetrazol-5-one, mp 149°-150° C.

Step B: 1-(2,4-Dichloro-5-methoxymethoxyphenyl)-1,4-dihydro-4-ethyl-5H-tetrazol-5-one To a stirred mixture of 0.8 g (0.0029 mole) of 1-(2,4-dichloro-5-hydroxyphenyl)-1,4-dihydro-4-ethyl-5H-tetrazol-5-one, 2.8 g (0.032 mole) of N,N-dimethylacetamide, and 0.14 g (0.0029 mole) of sodium hydride (50% in oil) in 25 mL of toluene was added 0.47 g (0.0058 mole) of chloromethyl methyl ether. The reaction mixture was stirred at room temperature for approximately 18 hours then poured into ice water and extracted with diethyl ether. The extract was dried over anhydrous magnesium sulfate, filtered, and the filtrate evaporated to leave a solid. The solid was purified by recrystallization from heptane to yield 0.19 g of 1-(2,4-dichloro-5-methoxymethoxyphenyl)-1,4-dihydro-4-ethyl-5H-tetrazol-5-one, mp 112°-113° C.

The nmr spectrum was consistent with the proposed structure.

The tetrazolinone prepared in Example 13 is listed as compound 66 in Table 1. Other tetrazolinones prepared by this method were compounds 68-72.

EXAMPLE 14

1-[2,4-Dichloro-5-(2-tetrahydrofuranyloxy)phenyl]-1,4-dihydro-4-propyl-5H-tetrazol-5-one To a stirred solution of 1.0 g (0.0035 mole) of 1-(2,4-dichloro-5-hydroxyphenyl)-1,4-dihydro-4-propyl-5H-tetrazol-5-one (Example 10, Step A) and 0.05 g (0.00026 mole) of 4-methylphenylsulfonic acid in 40 mL of p-dioxane was added slowly 0.88 g (0.0126 mole) of dihydrofuran in 20 mL of p-dioxane. The mixture was stirred at room temperature for approximately 18 hours, and an additional 0.88 g of dihydrofuran was added. The mixture was stirred at room temperature for an additional 48 hours. One mL of methanol saturated with ammonia was added to the mixture and stirring was continued for a short period of time. The reaction mixture was evaporated under reduced pressure to leave a residue. The residue was purified by column chromatography on silica gel, eluting with methylene chloride, to yield 0.58 g of 1-[2,4-dichloro-5-(2-tetrahydrofuranyloxy)phenyl]-1,4-dihydro-4-propyl-5H-tetrazol-5-one as a solid, mp 89°-90° C.

The nmr spectrum was consistent with the proposed structure.

The tetrazolinone of Example 14 is listed as compound 76 in Table 1. Compounds 79, 102, and 103 were also prepared by this process.

EXAMPLE 15

1-(5-Acetyloxy-2,4-dichlorophenyl)-1,4-dihydro-4-propyl-5H-tetrazol-5-one

To a stirred mixture of 0.1 g (0.0021 mole) of sodium hydride (50% in oil) in 30 mL of tetrahydrofuran was added slowly 0.5 g (0.0017 mole) of 1-(2,4-dichlorofuranyloxy)phenyl]-1,4-dihydro-4-propyl-5H-tetrazol-5-one (Example 10, Step A). The mixture was stirred for 15 minutes and 0.16 g (0.0021 mole) of acetyl chloride was slowly added. The reaction mixture was stirred at room temperature for approximately 18 hours. The mixture was poured into ice water, and the resulting precipitate was collected on a filter paper. Recrystallization from ethyl acetate:heptane gave 0.15 g of 1-(5-acetoxy-2,4-dichlorophenyl)-1,4-dihydro-4-propyl-5H-tetrazol-5-one, mp 91°-92° C.

The nmr spectrum was consistent with the proposed structure.

The tetrazolinone prepared in Example 15 is listed in Table 1 as compound 81.

EXAMPLE 16

2,4-Dichloro-5-(1,4-dihydro-5-oxo-4-propyl-tetrazol-1-yl)phenoxyacetic acid

A stirred solution of 0.5 g (0.0014 mole) of methyl 2,4-dichloro-5-(1,4-dihydro-5-oxo-4-propyltetrazol-1-yl)phenoxyacetate (compound 83) and 0.08 g (0.0021 mole) of sodium hydroxide in 10 mL of methanol was heated at reflux temperature for 1.5 hours. The reaction mixture was cooled, then evaporated under reduced pressure to leave a solid residue. The residue was dissolved in 20 mL of water, and the solution acidified with concentrated hydrochloric acid. A solid precipitate formed and was collected by filtration and washed with cold water. Recrystallization from diethyl ether:pentane provided 0.2 g of 2,4-dichloro-5-[1,4-dihydro-5-oxo-4-propyltetrazol-1-yl)phenoxyacetic acid, mp 134°-136° C.

The nmr spectrum was consistent with the proposed structure.

The tetrazolinone prepared in Example 16 is listed in Table 1 as compound 82.

EXAMPLE 17

1-(2,4-Dichloro-5-methylsulfonyloxyphenyl)-1,4-dihydro-4-propyl-5H-tetrazol-5-one A stirred solution of 0 5 g (0.0017 mole) of 1-(2,4-dichloro-5-hydroxyphenyl)-1,4-dihydro-4-propyl-5H-tetrazol-5-one (Example 10, Step A) and 0.26 g (0.0026 mole) of triethylamine in 30 mL of methylene chloride was cooled to 0° C. Methanesulfonyl chloride (0.22 g, 0.0019 mole) was added slowly to the reaction mixture. After complete addition, the mixture was allowed to warm to room temperature and was stirred for several days. The mixture was poured into ice water and extracted with diethyl ether. The ether extract was dried over anhydrous magnesium sulfate, filtered, and the filtrate evaporated under reduced pressure to leave a residue. The residue was purified by column chromatography on silica gel to yield 0.33 g of 1-(2,4-dichloro-5-methylsulfonyloxyphenyl)-1,4-dihydro-4-propyl-5H-tetrazol-5-one was a solid, mp 64°-65° C.

The nmr spectrum was consistent with the proposed structure.

The tetrazolinone prepared in Example 17 is listed in Table 1 as compound 86. Compounds 87-89 were also prepared by this method.

EXAMPLE 18

1-(2-Chloro-5-methoxy-4-trifluoromethylphenyl)-1,4-dihydro-4-propyl-5H-tetrazol-5-one Under a dry nitrogen atmosphere a stirred mixture of 6.0 g (0.044 mole) of sodium trifluoroacetate and 4.18 g (0.022 mole) of copper(I) iodide in 40 mL of N,N-dimethylacetamide was heated at 150° C. To the hot mixture was added 3.3 9 (0.011 mole) of 1-(4-bromo-2-chloro-5-methoxyphenyl)-1,4-dihydro-4-propyl-5H-tetrazol-5-one (compound 12). After complete addition, the hot mixture was stirred for 3 hours then allowed to cool to room temperature. The mixture was filtered and the filtrate diluted with ice water to form a precipitate. The solid was collected by filtration and purified, first by column chromatography on silica gel eluting with methylene chloride:heptane (80:20), then by recrystallization from heptane to yield 0.7 g of 1-(2-chloro-5- methoxy-4-trifluoromethylphenyl)-1,4-dihydro-4-propyl-5H-tetrazol-5-one, mp 82°-83° C.

The nmr spectrum was consistent with the proposed structure.

The tetrazolinone prepared in Example 18 is listed in Table 1 as compound 94. Compound 108 was also prepared by this method.

EXAMPLE 19

1-[2-Chloro-4-fluoro-5-(2-propynyloxy)phenyl]-1,4-dihydro-4-ethyl-5H-tetrazol-5-one Step A: Di-4-chloro-2-fluorophenyl carbonate A stirred solution of 11.5 g (0.078 mole) of 2-fluoro-4-chlorophenol sodium salt in 80 mL of p-dioxane and 30 mL of water was cooled to 5°-10° C. A solution of phosgene in toluene (35 mL of a 12.5% solution, 0.039 mole phosgene) was added slowly to the cold reaction mixture. After complete addition, the mixture was stirred at room temperature for approximately 18 hours. The mixture was poured into ice water and the organic phase separated. The organic phase was dried over anhydrous magnesium sulfate, filtered, and the filtrate evaporated to leave an oil The oil was purified by crystallization from petroleum ether to yield 6.0 g of di-4-chloro-2-fluorophenyl carbonate, mp 89°-90° C.

Step B: Di-4-chloro-2-fluoro-5-nitrophenyl carbonate

To 50 mL of fuming nitric acid, cooled to 10° C., was added 6.0 g (0.02 mole) of di-4-chloro-2-fluorophenyl carbonate. After complete addition, the mixture was stirred for 30 minutes at 10° C. then poured into ice water. A solid formed and was collected by filtration and rinsed with water to yield 7.5 g of di-4-chloro-2-fluoro-5-nitrophenyl carbonate.

Step C: 4-Chloro-2-fluoro-5-nitrophenol

A solution of 1.2 g (0.03 mole) of sodium hydroxide in 30 mL of water was added to a stirred solution of 7.5 g (0.019 mole) of di-4-chloro-2-fluoro-5-nitrophenyl carbonate in 60 mL of p-dioxane. After complete addition, the mixture was stirred for 1 hour. The mixture was diluted with 100 mL of water and the resulting solution neutralized with concentrated hydrochloric acid. A solid formed and was collected by filtration and washed with petroleum ether to yield 6.0 g of 4-chloro-2-fluoro-5-nitrophenol, mp 85°-86° C.

The nmr spectrum was consistent with the proposed structure.

Step D: 1-Chloro-3-fluoro-4-methoxy-6-nitrobenzene

In the manner of Example 3, Step C, the reaction of 6.0 g (0.031 mole) of 4-chloro-2-fluoro-5-nitrophenol, 6.35 g (0.046 mole) of potassium carbonate, and 8.8 g (0.062 mole) of methyl iodide in 80 mL of acetone produced 6 1 g of 1-chloro-3-fluoro-4-methoxy-6-nitrobenzene as a solid, mp 80°-81° C.

Step E: 2-Chloro-4-fluoro-5-methoxyaniline

The hydrogenation of 4.5 9 (0.022 mole) of 1-chloro-3-fluoro-4-methoxy-6-nitrobenzene in the presence of 0.15 g of platinum oxide in 200 mL of absolute ethanol produced 3.2 g of 2-chloro-4-fluoro-5-methoxyaniline.

Step F: 2-Chloro-4-fluoro-5-methoxyphenyl isocyanate

In the manner of Example 2, Step D, the reaction of 3.0 g (0.017 mole) of 2-chloro-4-fluoro-5-methoxyaniline with 1.68 g (0.0085 mole) of trichloromethyl chloroformate in 20 mL of toluene produced 3.0 g of 2-chloro-4-fluoro-5-methoxyphenyl isocyanate.

Step G: 1-(2-Chloro-4-fluoro-5-methoxyphenyl)-1,4-dihydro-5H-tetrazol-5-one

In the manner of Example 2, Step E, the reaction of 3.2 g (0.016 mole) of 2-chloro-4-fluoro-5-methoxyphenyl isocyanate with 3.2 g (0.028 mole) of trimethylsilyl azide produced 3.0 g of 1-(2-chloro-4-fluoro-5-methoxyphenyl)-1,4-dihydro-5H-tetrazol-5-one.

Step H: 1-(2-Chloro-4-fluoro-5-methoxyphenyl)-1,4-dihydro-4-ethyl-1,4-dihydro-5H-tetrazol-5-one In the manner of Example 2, Step F, the reaction of 1.33 g (0.0054 mole) of 1-(2-chloro-4-fluoro-5-methoxyphenyl)-1,4-dihydro-5H-tetrazol-5-one with 0.26 g (0.0054 mole) of sodium hydride and 1.6 g (0.01 mole) of iodoethane in 60 mL of dimethylsulfoxide produced 1.26 g of 1-(2-chloro-4-fluoro-5-methoxyphenyl)-1,4-dihydro-4-ethyl-5H-tetrazol-5-one, compound 105, 79°-80° C. Compound 106 was prepared in a similar manner.

Step I: 1-(2-Chloro-4-fluoro-5-hydroxyphenyl)-1,4-dihydro-4-ethyl-5H-tetrazol-5-one In the manner of Example 11, Step A, the reaction of 0.9 g (0.0033 mole) of 1-(2-chloro-4-fluoro-5-methoxyphenyl)-1,4-dihydro-4-ethyl-5H-tetrazol-5-one with 2.5 g (0.01 mole) of boron tribromide in 15 mL of methylene chloride produced 0.8 g of 1-(2-chloro-4-fluoro-5-hydroxyphenyl)-1,4-dihydro-4-ethyl-5H-tetrazol-5-one.

Step J: 1-[2-Chloro-4-fluoro-5-(2-propynyloxy)phenyl]-1,4-dihydro-4-ethyl-5H-tetrazol-5-one In the manner of Example 8, Step B, the reaction of 0.8 g (0.0031 mole) of 1-(2-chloro-4-fluoro-5-hydroxyphenyl)-1,4-dihydro-4-ethyl-5H-tetrazol-5-one with 0.9 g (0.0062 mole) of 1-bromo-2-propyne and 0.63 g (0.0046 mole) of potassium carbonate in 25 mL of acetone produced 0.6 g of 1-[2-chloro-4-fluoro-5-(2-propynyloxy)phenyl]-1,4-dihydro-4-ethyl-5H-tetrazol-5-one, mp 88°-89° C.

The nmr spectrum was consistent with the proposed structure.

The tetrazolinone prepared in Example 19 is listed in Table 1 as compound 44. Compound 47 was also prepared by the process described in this Example.

EXAMPLE 20

1-(2,4-Dichloro-5-methoxyphenyl)-4-ethenyl-1,4-dihydro-5H-tetrazol-5-one

Step A: 1-(2,4-Dichloro-5-methoxyphenyl)-1,4-dihydro-4-(2-hydroxyethyl)-5H-tetrazol-5-one In the manner of Example 10, Step B, 3.3 g (0.058 mole) of potassium fluoride was reacted with 3.0 g (0.0115 mole) of 1-(2,4-dichloro-5-methoxyphenyl)-1,4-dihydro-5H-tetrazol-5-one (prepared from 2,4-dichloro-5-methoxyaniline, Example 3, using the process of Example 2, Steps D and E) in 45 mL of N,N-dimethylformamide. Subsequent treatment with 5.9 g (0.035 mole) of 2-iodoethanol produced 1.1 g of 1-(2,4-dichloro-5-methoxyphenyl)-2,5-dihydro-4-(2-hydroxyethyl)-5H-tetrazol-5-one as a solid, mp 109°-110° C.

Step B: 1-(2,4-Dichloro-5-methoxyphenyl)-1,4-dihydro-4-[2-(methylsulfonyloxy)ethyl]-5H-tetrazol-5-one A stirred solution of 0.9 g (0.003 mole) of 1-(2,4-dichloro-5-methoxyphenyl)-1,4-dihydro-4-(2-hydroxyethyl)-5H-tetrazol-5-one and 0.45 g (0.0044 mole) of triethylamine in 35 mL of methylene chloride was cooled to 0° C. To the cool solution was added 0.37 g (0.0033 mole) of methanesulfonyl chloride. After complete addition, the mixture was allowed to warm to room temperature and was stirred for approximately 18 hours. The mixture was poured into ice water. Sodium chloride was added and the mixture was extracted with diethyl ether. The ether extract was dried over anhydrous magnesium sulfate, filtered, and the filtrate evaporated under reduced pressure to yield 1.0 g of 1-(2,4-dichloro-5-methoxyphenyl)-1,4-dihydro-4-2-(methylsulfonyloxy)ethyl]-5H-tetrazol-5-one as an oil.

Step C: 1-(2,4-Dichloro-5-methoxyphenyl)-4-ethenyl-1,4-dihydro-5H-tetrazol-5-one A stirred mixture of 0.38 g (0.0066 mole) of potassium fluoride and 0.85 g (0.0022 mole) of 1-(2,4-dichloro-5-methoxyphenyl)-1,4-dihydro-4-[2(methylsulfonyloxy)ethyl]-5H-tetrazol-5-one in 35 mL of N,N-dimethylformamide was heated at 120°–130° C. for 2 hours, then stirred at room temperature for 3 days. The reaction mixture was poured into ice water then extracted with diethyl ether. The ether extract was dried over anhydrous magnesium sulfate, filtered, and the filtrate evaporated under reduced pressure to leave a residue. The residue was purified by column chromatography on silica gel, eluting with methylene chloride, then recrystallized from ethyl acetate:heptane to yield 0.25 g of 1-(2,4-dichloro-5-methoxyphenyl)-4-ethenyl-1,4-dihydro-5H-tetrazol-5-one, mp 142°–143° C.

The nmr and ir spectra were consistent with the proposed structure.

The tetrazolinone prepared in Example 20 is listed as compound 104 in Table 1.

EXAMPLE 21

1-(4-Bromomethyl-2-chloro-5-isopropoxyphenyl)-1,4-dihydro-4-propyl-5H-tetrazol-5-one Under a dry nitrogen atmosphere, a stirred solution of 4.4 g (0.014 mole) of 1-(2-chloro-4-methyl-5-isopropoxyphenyl)-1,4-dihydro-4-propyl-5H-tetrazol-5-one (compound 91), 2.5 g (0.014 mole) of N-bromosuccinimide, and 0.06 g (0.00025 mole) of benzoyl peroxide in 80 mL of carbon tetrachloride was heated at reflux temperature for two days. The reaction mixture was allowed to cool to room temperature, filtered, and the filtrate washed with a saturated aqueous sodium chloride solution. The washed filtrate was dried over anhydrous magnesium sulfate, filtered, and the filtrate evaporated under reduced pressure to leave an oil. The oil was crystallized from petroleum ether to yield 2.7 g of 1-(4-bromomethyl-2-chloro-5-isopropoxyphenyl)-1,4-dihydro-4-propyl-5H-tetrazol-5-one, mp 68°–70° C.

The nmr spectrum was consistent with the proposed structure.

The tetrazolinone of Example 21 is listed as compound 107 in Table 1.

EXAMPLE I'

Synthesis of 1-(5-Amino-4-chloro-2-fluorophenyl)-1,4-dihydro-4-(3-fluoropropyl-5H-tetrazol-5-one as an intermediate Step A Synthesis of 4-chloro-2-fluorophenyl isocyanate as an intermediate To a stirred solution of 20.0 grams (0.13 mole) of 4-chloro-2-fluoroaniline in 250 ml of toluene was added dropwise a solution of 17.2 ml (0.13 mole) of trichloromethyl chloroformate in 40 ml of toluene. Upon completion of addition the reaction mixture was heated to reflux where it stirred for 16 hours. The solvent was separated from the reaction mixture by distillation to yield 21.8 grams of 4-chloro-2-fluorophenyl isocyanate as an oil. The reaction was repeated several times.

Step B Synthesis of 1-(4-chloro-2-fluorophenyl)-1,4-dihydro-5H-tetrazol-5-one as an intermediate A stirred solution of 17.1 grams (0.10 mole) of 4-chloro-2-fluorophenyl isocyanate and 20.0 grams (0.17 mole) of azidotrimethylsilane was heated under reflux for 16 hours. The reaction mixture was cooled to ambient temperature and 60 ml of toluene and 100 ml of water were added. The mixture was allowed to stand for two hours and the resultant solid collected by filtration. The filter cake was washed with petroleum ether to yield 14.5 grams of 1-(4-chloro-2-fluorophenyl)-1,4-dihydro-5H-tetrazol-5-one; m.p. 185°–187° C. The reaction was repeated several times.

Step C Synthesis of 1-(4-Chloro-2-fluorophenyl)-1,4-dihydro-4-(3-fluoropropyl)-5H-tetrazol-5-one as an intermediate A stirred solution of 4.7 grams (0.22 mole) of 1-(4-chloro-2-fluorophenyl)-1,4-dihydro-5H-tetrazole, 4.0 grams (0.028 mole) of 3-fluoropropyl bromide and 4.0 grams (0.028 mole) of potassium carbonate in 60 ml of dimethylformamide was heated at 60° C. for 16 hours. The reaction mixture was poured into water and the mixture extracted with diethyl ether. The combined ether extract was dried with magnesium sulfate and filtered. The filtrate was concentrated under reduced pressure to a residue. The residue was dissolved in methylene chloride and passed through a pad of silica gel. The eluate was concentrated under reduced pressure to yield 3.5 grams of 1-(4-chloro-2-fluorophenyl-1,4-dihydro-4-(3-fluoropropyl)-5H-tetrazol-5-one; m.p. 62°–63° C. The reaction was repeated several times.

Step D Synthesis of 1-(4-chloro-2-fluoro-5-nitrophenyl)-1,4-dihydro-4-(3-fluoropropyl)-5H-tetrazol-5-one as an intermediate To a stirred solution of 3.1 grams (0.011 mole) of 1-(4-chloro-2-fluorophenyl)-1,4-dihydro-4-(3-fluoropropyl)-5H-tetrazol-5-one in 5 ml of concentrated sulfuric acid was added dropwise 0.9 ml (0.011 mole) of 70% nitric acid. Upon completion of addition the reaction mixture was stirred for two hours at ambient temperature then was poured into ice-water. The mixture was extracted with diethyl ether. The combined extracts were dried with magnesium sulfate and filtered. The filtrate was concentrated under reduced pressure to a residue. The residue was dissolved in methylene chloride and passed through a pad of silica gel. The eluate was concentrated under reduced pressure to yield 2.8 grams of 1-(4-chloro-2-fluoro-5-nitrophenyl)-1,4-dihydro-4-(3-fluoropropyl)-5H-tetrazol-5-one; m.p. 80°–81° C. The reaction was repeated several times.

Step E Synthesis of 1-(5-amino-4-chloro-2-fluorophenyl)-1,4-dihydro-4-(3-fluoropropyl)-5H-tetrazol-5-one as an intermediate To a 500 ml Parr hydrogenation bottle was added 0.2 gram of platinum oxide, 200 ml of methanol, then 14.0 grams (0.014 mole) of 1-(4-chloro-2-fluoro-5-nitrophenyl)-1,4-dihydro-4-(3-fluoropropyl)-5H-tetrazol-5-one. The bottle was placed in a Parr hydrogenator and the reaction mixture hydrogenated until the theoretical amount of hydrogen was taken up. The bottle was removed from the hydrogenator and the reaction mixture filtered. The filtrate was concentrated under reduced pressure to a residue. The residue was dissolved in methylene chloride and subjected to column chromatography on silica gel. The appropriate fractions were combined and concentrated under reduced pressure to yield 10.0 grams of 1-(5-amino-4-chloro-2-fluorophenyl)-1,4-dihydro-4-(3-fluoropropyl)-5H-tetrazol-5-one; m.p. 84°-86° C. The reaction was repeated several times.

EXAMPLE II'

Synthesis of 1-[4-Chloro-2-fluoro-5-[bis(N-ethylsulfonyl)amino]-phenyl]-1,4-dihydro-4-(3-fluoropropyl)-5H-tetrazol-5-one To a stirred solution of 1.0 gram (0.0035 mole) of 1-(5-amino-4-chloro-2-fluorophenyl)-1,4-dihydro-4-(3-fluoropropyl)-5H-tetrazol-5-one (prepared as in Example I') in 20 ml of methylene chloride was slowly added 0.7 gram (0.007 mole) of triethylamine. The reaction mixture was cooled to 10° C. and 0.9 gram (0.007 mole) of ethanesulfonyl chloride was added dropwise. Upon completion of addition the reaction mixture was allowed to warm to ambient temperature where it stirred for 16 hours. The reaction mixture was poured into ice-water and the organic layer separated. The organic layer was concentrated under reduced pressure to a residue. The residue was dissolved in methylene chloride and subjected to column chromatography on silica gel. The appropriate fractions were combined and concentrated under reduced pressure to yield 0.56 gram of 1-[4-Chloro-2-fluoro-5-[bis(N-ethylsulfonyl)-amino]-phenyl]-1,4-dihydro-4-(3-fluoropropyl)-5H-tetrazol-5-one; m.p. 127°-129° C.

The nmr spectrum was consistent with the proposed structure.

EXAMPLE III'

Synthesis of 1-[4-Chloro-2-fluoro-5-(ethylsulfonylamino)phenyl]-1,4-dihydro-4-(3-fluoropropyl)-5H-tetrazol-5-one To a stirred solution of 7.9 grams (0.017 mole) of 1-[4-chloro-2-fluoro-5-[bis(N-ethylsulfonyl)-amino]-phenyl]-1,4-dihydro-4-(3-fluoropropyl)-5H-tetrazol-5-one (prepared as in Example II') in 100 ml of ethanol was added dropwise a solution of 1.3 grams (0.033 mole) of sodium hydroxide in 6 ml of water. Upon completion of addition the reaction mixture stirred for 10 minutes and 100 ml of water was added. The mixture was neutralized with concentrated hydrochloric acid and the resultant solid collected by filtration. The solid was dried to yield 5.0 grams of 1-[4-chloro-2-fluoro-5-(ethylsulfonylamino)phenyl]-1,4-dihydro-4-(3-fluoropropyl)-5H-tetrazol-5-one; m.p. 84°-85° C.

The nmr spectrum was consistent with the proposed structure.

EXAMPLE IV'

Synthesis of 1-[4-Bromo-2-fluoro-5-[bis(N-methylsulfonyl)amino]-phenyl]-1,4-dihydro-4-(3-fluoropropyl)-5H-tetrazol-5-one This compound was prepared by a method analogous to that of Example II' using 1.0 gram (0.003 mole) of 1-(5-amino-4-bromo-2-fluorophenyl)-1,4-dihydro-4-(3-fluoropropyl)-5H-tetrazol-5-one (prepared as in Example I'), 0.69 gram (0.006 mole) of methanesulfonyl chloride, and 0.61 gram (0.006 mole) of triethylamine in 20 ml of methylene chloride. The yield of 1-[4-bromo-2-fluoro-5-[bis(N-methylsulfonyl)amino]phenyl]-1,4-dihydro-4-(3-fluoropropyl)-5H-tetrazol-5-one was 0.6 gram; m.p. 143°-144° C.

The nmr spectrum was consistent with the proposed structure.

RICE BLAST TESTING PROCEDURE

Preparation of Inoculum

Media Preparation: A mixture of 5.0 g of agar in 500 mL of water was heated until the agar melted. A mixture of 40.0 g of Quaker ® Instant Oatmeal in 250 mL of water was added. The mixture was placed in an autoclave and was heated at 121° C. for 0.5 hour. After cooling, approximately 50 mL of the media was poured into each of 15 petri dishes.

Inoculum Preparation: Under sterile conditions, each petri dish was inoculated with mycelial plugs of [Pyricularia oryzae (race IB-49) onto the surface of the media. The inoculated plates were incubated for seven to ten days in a growth chamber at 25° C., approximately 40% humidity, and a photo period of 12 hours of light and 12 hours of dark using fluorescent lamps. The mycelia from the incubated plates were scraped into a beaker, and the resulting mixture was blended. This mixture was filtered through cheesecloth, and the filtrate which contained the rice blast spores was saved for the inoculation of rice plants.

Rice Treatment

Plastic pots (7 cm×7 cm×6.5 cm) were filled to an approximate depth of 4.5 cm with steam-sterilized sandy loam soil. The soil was leveled and pressed with a flat templet. Approximately 10 to 15 seeds of rice were placed on the flattened soil, and the seeds were firmly pressed into soil. A topping soil of equal proportions of sand and sandy loam soil was placed uniformly on top of each flat to a depth of approximately 0.5 cm.

The pots were placed in a greenhouse and watered regularly for 14 days after which the pots were drenched with a solution of the test compound as described below. One day post treatment the rice plants were inoculated with the rice blast spore suspension using a DeVilbiss hand held sprayer. The inoculated plants were immediately placed in a dark, humidified growth chamber (72° F., 88% humidity) for 24 hours. The flats were moved to a greenhouse and were bottom watered for the duration of the test.

The test compounds were applied as 50 g/liter flowable or an emulsifiable concentrate at rates equivalent to 0.125 kg/ha or submultiples thereof, i.e., 0.0313 kg/ha, 0.0078 kg/ha, and so on. The applications were made as soil drenches using 20 mL of test solution of the appropriate concentration for each of these pots per compound.

For pots the size described above, an application rate of 0.125 kg/ha of test compound is equivalent to 0.000079 g/pot. A solution of 0.000435 g of test compound in 120 mL of distilled water containing 0.5% v/v of sorbitan monolaurate emulsifier/solubilizer was prepared. For application as a soil drench to the test pots, 60 mL of this solution was divided equally between the three pots (i.e. 20 mL per pot). The remaining 60 ml of the 0.125 kg/ha solution was decanted into 60 mL of the distilled water/emulsifier solution to produce a 120 mL solution containing 0.000217 g of the test compound, a rate of 0.0625 kg/ha. Sixty mL of this solution was decanted into 60 mL of the water/emulsifier solution to produce 120 mL of a mixture which contained 0.000108 g of the test compound, a rate of 0.0313 kg/ha. The process above was repeated, i.e. 60 mL of the 0.0313 kg/ha solution was used for the soil drench application and 60 mL was decanted into 60 mL of water/emulsifier solution for the 0.0156 kg/ha rate, etc.

The rice plant injury (phytotoxicity) and fungicidal activity were recorded at seven days post treatment. Phytotoxicity data were taken as percent control.

HERBICIDAL ACTIVITY

The plant test species used in demonstrating the herbicidal activity of compounds of this invention include cotton (*Gossypium hirsutum* var. Stoneville), soybean (*Glycine max* var. Williams), field corn (*Zea mays* var. Agway 595S), rice (*Oryza sativa* var. Labelle), wheat (*Triticum aestivium* var. Prodax), field bindweed (*Convolvulus arvensis*), morningglory (*Ipomea lacunosa* or *Ipomea hederacea*), velvetleaf (*Abutilon theophrasti*), barnyardgrass (*Echinochloa crus galli*), green foxtail (*Setaria viridis*), johnsongrass (*Sorghum halepense*), and yellow nutsedge (*Cyperus esculentus*).

Seeds or tubers of the plant test species were planted in furrows in steam sterilized sandy loam soil contained in disposable fiber flats. A topping soil of equal portions of sand and sandy loam soil was placed uniformly on top of each flat to a depth of approximately 0.5 cm.

The flats for the preemergence test were watered, then drenched with the appropriate amount of a solution of the test compound in a mixture of acetone and water containing a small amount (up to 0.5% v/v) of sorbitan monolaurate emulsifier/solubilizer. The concentration of the test compound in solution was varied to give a range of application rates, generally 8.0 kg/ha and submultiplies thereof. The flats were placed in a greenhouse and watered regularly at the soil surface for 21 days at which time phytotoxicity data were recorded.

The flats for the postemergence test were placed in a greenhouse and watered for 8-10 days, then the foliage of the emerged test plants was sprayed with a solution of the test compound in acetone-water containing up to 0.5% sorbitan monolaurate. After spraying, the foliage was kept dry for 24 hours, then watered regularly for 21 days, and phytotoxicity data recorded.

Phytotoxicity data were taken either as percent kill or percent control. Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. The present rating system is as follows:

| Rating Percent Control | Description of Main Categories | Crop Description | Weed Description |
|---|---|---|---|
| 0 | No effect | No crop reduction or injury | No weed control |
| 10 | Slight effect | Slight discoloration or stunting | Very poor weed control |
| 20 | | Some discoloration, stunting or stand loss | Poor weed control |
| 30 | | Crop injury more pronounced but not lasting | Poor to deficient weed control |
| 40 | Moderate effect | Moderate injury, crop usually recovers | Deficient weed control |
| 50 | | Crop injury more lasting, recovery | Deficient to moderate weed control |
| 60 | | Lasting crop injury no recovery | Moderate weed control |
| 70 | Severe | Heavy injury and stand loss | Control somewhat less than satisfactory |
| 80 | | Crop nearly destroyed a few survivors | Satisfactory to good weed control |
| 90 | | Only occasional live plants left | Very good to excellent control |
| 100 | Complete effect | Complete crop destruction | Complete weed destruction |

Herbicidal data at selected application rates are given for various compounds of the invention in Table 3 and 4 below. The test compounds are identified in the tables below by numbers which correspond to those in Table 1 above.

In the tables of herbicidal data below:
"kg/ha" is kilograms per hectare,
"% K" is percent kill, and
"% C" is percent control.

It is clear that the generic class of aryltetrazolinones and thiones described and illustrated herein is characterized by herbicidal activity, and that the degree of this activity varies among specific compounds within this class and to some extent among the species of plant to which these compounds may be applied. Thus, selection of a specific herbicidal compound for control of a specific plant may readily be made.

For herbicidal application, the active compounds as above defined are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, water-soluble or water-dispersible granules, as powdery dusts, as wettable powders, as emulsifiable concentrates, as solutions or as any of several other known types of formulations, depending on the desired mode of application.

For preemergence application these herbicidal compositions are usually applied either as sprays, dusts, or granules to the areas in which suppression of vegetation is desired. For postemergence control of established plant growth, sprays or dusts are most commonly used. These formulations may contain as little as 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently, additional wetting agent and/or oil will be added to the tank-mix for post-emergence application to facilitate dispersion on the foliage and absorption by the plant.

Other useful formulations for herbicidal applications are emulsifiable concentrates. Emulsifiable concentrates are homogeneous liquid or past compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Typical wetting, dispersing or emulsifying agents used in agricultural formulations include, for example, the alkyl and alkylaryl sulfonates and sulfates and their sodium salts; polyhydric alcohols; and other types of surface active agents, many of which are available in commerce. The surface active agent, when used, normally comprises 1% to 15% by weight of the herbicidal composition.

Other useful formulations for herbicidal applications include simple solutions of the active ingredient in a dispersant in which it is completely soluble at the desired concentration, such as acetone, alkylated naphthalenes, xylene or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal application of the present compounds. Such granular formulations are free-flowing, non-dusty, and readily water-soluble or water-miscible. This soluble or dispersible granular formulations described in U.S. Pat. No. 3,920,442, incorporated herein by reference are useful herein with the present herbicidal compounds.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed. The amount may be as low as, for example, 7 g/ha or lower.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl)-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-{[4-chloro-6-(ethylamino)-1,3,5-triazin-2-yl]amino}-2-methyl-propanenitrile (cyanazine); dinitrolaniline herbicides such as 2,6-dinitro-N,N-dipropyl-4-(trifluoromethyl)-benzeneamine (trifluralin); and aryl urea herbicides such as N'-(3,4-dichlorophenyl)-N,N-dimethylurea (diuron) and N,N-dimethyl-N'-[3-(trifluoromethyl)phenyl]urea (fluometuron).

It is apparent that various modifications may be made in the formulation and application of the compounds of this invention without departing from the inventive concepts herein as defined in the claims.

TABLE 1

Representative Compounds

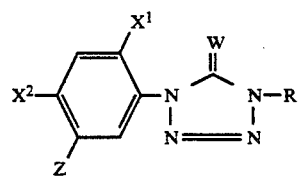

| Cpd No. | $X^1$ | $X^2$ | Z | R | W |
|---|---|---|---|---|---|
| 1 | Cl | Cl | Cl | $n$-$C_3H_7$ | O |
| 2 | Cl | Cl | Cl | $CH_2CH=CH_2$ | O |
| 3 | Cl | Cl | Cl | $CH_2OCH_3$ | O |
| 4 | Cl | Cl | $CH_3$ | $n$-$C_3H_7$ | O |
| 5 | Cl | Cl | $CH_3$ | $CH_2CH=CH_2$ | O |
| 6 | Cl | Cl | $OCH_3$ | $CH_3$ | O |
| 7 | Cl | Cl | $OCH_3$ | $C_2H_5$ | O |
| 8 | F | F | $OCH_3$ | $C_2H_5$ | O |
| 9 | Cl | Cl | $OCH_3$ | $n$-$C_3H_7$ | O |
| 10 | F | F | $OCH_3$ | $n$-$C_3H_7$ | O |
| 11 | F | Cl | $OCH_3$ | $n$-$C_3H_7$ | O |
| 12 | Cl | Br | $OCH_3$ | $n$-$C_3H_7$ | O |
| 13 | Br | Cl | $OCH_3$ | $n$-$C_3H_7$ | O |

TABLE 1-continued

Representative Compounds

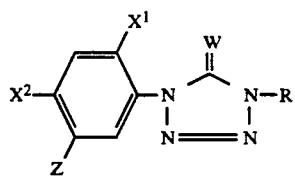

| Cpd No. | X¹ | X² | Z | R | W |
|---|---|---|---|---|---|
| 14 | Cl | Cl | OCH$_3$ | n-C$_4$H$_9$ | O |
| 15 | Cl | Cl | OCH$_3$ | CH(CH$_3$)$_2$ | O |
| 16 | Cl | Cl | OCH$_3$ | CH$_2$CH(CH$_3$)$_2$ | O |
| 17 | Cl | Cl | OCH$_3$ | CHF$_2$ | O |
| 18 | Cl | Cl | OCH$_3$ | CH$_2$CH$_2$F | O |
| 19 | Cl | Cl | OCH$_3$ | (CH$_2$)$_2$CH$_2$F | O |
| 20 | Cl | Cl | OCH$_3$ | CH$_2$CH=CH$_2$ | O |
| 21 | Cl | Cl | OC$_2$H$_5$ | CH$_2$CH=CH$_2$ | O |
| 22 | Cl | Cl | OC$_2$H$_5$ | CH$_2$OCH$_3$ | O |
| 23 | Cl | Cl | O-n-C$_3$H$_7$ | CH$_3$ | O |
| 24 | Cl | Cl | O-n-C$_3$H$_7$ | n-C$_3$H$_7$ | O |
| 25 | Cl | Cl | O-n-C$_3$H$_7$ | CH$_2$CH=CH$_2$ | O |
| 26 | Cl | Cl | OCH(CH$_3$)$_2$ | n-C$_3$H$_7$ | O |
| 27 | Cl | Cl | OCH(CH$_3$)$_2$ | CH$_2$CH=CH$_2$ | O |
| 28 | Br | Br | OCH(CH$_3$)$_2$ | CH$_2$CH=CH$_2$ | O |
| 29 | Br | Br | OCH(CH$_3$)$_2$ | CH$_2$OCH$_3$ | O |
| 30 | Cl | Cl | O-n-C$_4$H$_9$ | n-C$_3$H$_7$ | O |
| 31 | Cl | Cl | OCH$_2$CH$_2$F | n-C$_3$H$_7$ | O |
| 32 | Cl | Cl | O(CH$_2$)$_2$CH$_2$F | n-C$_3$H$_7$ | O |
| 33 | Cl | Cl | OCHF$_2$ | n-C$_3$H$_7$ | O |
| 34 | Cl | Cl | OCH$_2$CF$_3$ | n-C$_3$H$_7$ | O |
| 35 | F | F | OCH(CH$_3$)$_2$ | n-C$_3$H$_7$ | O |
| 36 | Cl | Br | OCH(CH$_3$)$_2$ | n-C$_3$H$_7$ | O |
| 37 | Cl | Cl | OCH$_2$CH(CH$_3$)$_2$ | n-C$_3$H$_7$ | O |
| 38 | Cl | Cl | OCH$_2$CH$_2$OH | n-C$_3$H$_7$ | O |
| 39 | Cl | Cl | OCH$_2$CH=CH$_2$ | n-C$_3$H$_7$ | O |
| 40 | Cl | Cl | OCH$_2$C(Cl)=CH$_2$ | n-C$_3$H$_7$ | O |
| 41 | Cl | Cl | OCH$_2$C≡CH | CH$_3$ | O |
| 42 | Cl | Cl | OCH$_2$C≡CH | C$_2$H$_5$ | O |
| 43 | F | F | OCH$_2$C≡CH | C$_2$H$_5$ | O |
| 44 | Cl | F | OCH$_2$C≡CH | C$_2$H$_5$ | O |
| 45 | Cl | Cl | OCH$_2$C≡CH | n-C$_3$H$_7$ | O |
| 46 | F | F | OCH$_2$C≡CH | n-C$_3$H$_7$ | O |
| 47 | Cl | F | OCH$_2$C≡CH | n-C$_3$H$_7$ | O |
| 48 | F | Cl | OCH$_2$C≡CH | n-C$_3$H$_7$ | O |
| 49 | Cl | Br | OCH$_2$C≡CH | n-C$_3$H$_7$ | O |
| 50 | Br | Cl | OCH$_2$C≡CH | n-C$_3$H$_7$ | O |
| 51 | Cl | Cl | OCH$_2$C≡CH | CH(CH$_3$)$_2$ | O |
| 52 | Cl | Cl | OCH$_2$C≡CH | n-C$_4$H$_9$ | O |
| 53 | Cl | Cl | OCH$_2$C≡CH | CH$_2$CH(CH$_3$)$_2$ | O |
| 54 | Cl | Cl | OCH$_2$C≡CH | CHF$_2$ | O |
| 55 | Cl | Cl | OCH$_2$C≡CH | CH$_2$CH$_2$F | O |
| 56 | Cl | Cl | OCH$_2$C≡CH | (CH$_2$)$_2$CH$_2$F | O |
| 57 | Cl | Cl | OCH$_2$C≡CH | (CH$_2$)$_2$CH$_2$Br | O |
| 58 | Cl | Cl | OCH$_2$C≡CH | CH$_2$=CH$_2$ | O |
| 59 | Cl | Cl | OCH$_2$C≡CH | CH$_2$OCH$_3$ | O |
| 60 | Cl | Cl | OCH$_2$C≡CH | CH$_2$OC$_2$H$_5$ | O |
| 61 | Cl | Cl | OCH$_2$C≡CCl | n-C$_3$H$_7$ | O |
| 62 | Cl | Cl | OCH$_2$C≡CCH$_3$ | n-C$_3$H$_7$ | O |
| 63 | Cl | Cl | OCH$_2$CN | n-C$_3$H$_7$ | O |
| 64 | Cl | Cl | OCH(CH$_3$)CN | n-C$_3$H$_7$ | O |
| 65 | Cl | Cl | OCH(CN)CH(CH$_3$)$_2$ | n-C$_3$H$_7$ | O |
| 66 | Cl | Cl | OCH$_2$OCH$_3$ | C$_2$H$_5$ | O |
| 67 | Cl | Cl | OCH$_2$OCH$_3$ | n-C$_3$H$_7$ | O |
| 68 | F | F | OCH$_2$OCH$_3$ | n-C$_3$H$_7$ | O |
| 69 | F | Cl | OCH$_2$OCH$_3$ | n-C$_3$H$_7$ | O |
| 70 | Cl | Br | OCH$_2$OCH$_3$ | n-C$_3$H$_7$ | O |
| 71 | Cl | Cl | OCH$_2$OC$_2$H$_5$ | n-C$_3$H$_7$ | O |
| 72 | Cl | Cl | OCH$_2$OCH$_3$ | (CH$_2$)$_2$CH$_2$F | O |
| 73 | Cl | Cl | O(CH$_2$)$_2$OC$_2$H$_5$ | n-C$_3$H$_7$ | O |
| 74 | Cl | Br | O(CH$_2$)$_2$OC$_2$H$_5$ | n-C$_3$H$_7$ | O |
| 75 | Cl | Cl | O(CH$_2$)$_2$OCH=CH$_2$ | n-C$_3$H$_7$ | O |
| 76 | Cl | Cl | 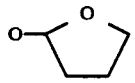 | n-C$_3$H$_7$ | O |

TABLE 1-continued

Representative Compounds

| Cpd No. | $X^1$ | $X^2$ | Z | R | W |
|---|---|---|---|---|---|
| 77 | Cl | Cl | OCH$_2$-(tetrahydrofuran-2-yl) | n-C$_3$H$_7$ | O |
| 78 | Cl | Cl | OCH$_2$-(1,3-dioxolan-2-yl) | n-C$_3$H$_7$ | O |
| 79 | Cl | Cl | O-(tetrahydropyran-2-yl) | n-C$_3$H$_7$ | O |
| 80 | Cl | Cl | OCH$_2$-(1,3-dioxan-2-yl) | n-C$_3$H$_7$ | O |
| 81 | Cl | Cl | O—C(=O)CH$_3$ | n-C$_3$H$_7$ | O |
| 82 | Cl | Cl | OCH$_2$CO$_2$H | n-C$_3$H$_7$ | O |
| 83 | Cl | Cl | OCH$_2$CO$_2$CH$_3$ | n-C$_3$H$_7$ | O |
| 84 | Cl | Cl | OCH$_2$CO$_2$C$_2$H$_5$ | n-C$_3$H$_7$ | O |
| 85 | Cl | Cl | OCH$_2$SCH$_3$ | n-C$_3$H$_7$ | O |
| 86 | Cl | Cl | OSO$_2$CH$_3$ | n-C$_3$H$_7$ | O |
| 87 | Cl | Br | OSO$_2$CH$_3$ | n-C$_3$H$_7$ | O |
| 88 | Cl | Cl | OSO$_2$CH(CH$_3$)$_2$ | n-C$_3$H$_7$ | O |
| 89 | Cl | Cl | OSO$_2$CF$_3$ | n-C$_3$H$_7$ | O |
| 90 | Cl | CH$_3$ | OCH$_3$ | n-C$_3$H$_7$ | O |
| 91 | Cl | CH$_3$ | OCH(CH$_3$)$_2$ | n-C$_3$H$_7$ | O |
| 92 | Cl | CH$_3$ | OCH$_2$C≡CH | n-C$_3$H$_7$ | O |
| 93 | Cl | CH$_3$ | O(CH$_2$)$_2$OC$_2$H$_5$ | n-C$_3$H$_7$ | O |
| 94 | Cl | CF$_3$ | OCH$_3$ | n-C$_3$H$_7$ | O |
| 95 | CH$_3$ | Cl | OCH$_3$ | n-C$_3$H$_7$ | O |
| 96 | CH$_3$ | Cl | OCH$_3$ | CH$_2$CH=CH$_2$ | O |
| 97 | CH$_3$ | Cl | OCH$_2$C≡CH | n-C$_3$H$_7$ | O |
| 98 | CH$_3$ | Cl | OCH$_2$C≡CH | CH$_2$CH=CH$_2$ | O |
| 99 | CH$_3$ | Cl | OCH$_2$OCH$_3$ | n-C$_3$H$_7$ | O |
| 100 | Cl | Cl | OCH(CH$_3$)$_2$ | CH(CH$_3$)$_2$ | O |
| 101 | Cl | Cl | OCH(CH$_3$)$_2$ | CH$_2$OCH$_3$ | O |
| 102 | Cl | Br | O-(tetrahydrofuran-2-yl) | n-C$_3$H$_7$ | O |
| 103 | Cl | Br | O-(tetrahydropyran-2-yl) | n-C$_3$H$_7$ | O |
| 104 | Cl | Cl | OCH$_3$ | CH=CH$_2$ | O |
| 105 | Cl | F | OCH$_3$ | C$_2$H$_5$ | O |
| 106 | Cl | F | OCH$_3$ | n-C$_3$H$_7$ | O |
| 107 | Cl | CH$_2$Br | OCH(CH$_3$)$_2$ | n-C$_3$H$_7$ | O |
| 108 | Cl | CF$_3$ | OCH(CH$_3$)$_2$ | n-C$_3$H$_7$ | O |
| 109 | Cl | Cl | H | n-C$_3$H$_7$ | O |
| 110 | Cl | Cl | H | CH(CH$_3$)$_2$ | O |
| 111 | Cl | Cl | H | CH$_2$OCH$_3$ | O |
| 112 | Cl | Cl | H | CH$_2$SCH$_3$ | O |
| 113 | Cl | Cl | H | CH$_2$CH=CH$_2$ | O |

TABLE 1-continued

Representative Compounds

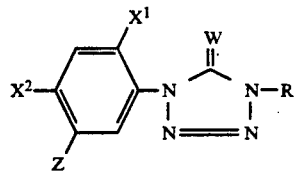

| Cpd No. | X¹ | X² | Z | R | W |
|---|---|---|---|---|---|
| 114 | Cl | Cl | H | $CH_2CN$ | O |
| 115 | F | Cl | $OCH_2C\equiv Cl$ | $n\text{-}C_3H_7$ | O |
| 116 | F | Cl | $OCH_2C\equiv CH$ | $C_2H_5$ | O |
| 117 | Cl | Cl | $OCH_2OC_2H_5$ | $(CH_2)_2CH_2F$ | O |
| 118 | F | Cl | $OCH_3$ | $C_2H_5$ | O |
| 119 | Cl | Cl | $OCH_2C_6H_5$ | $CH_2C(O)CH_3$ | O |
| 120 | F | Cl | $OCH_2C_6H_5$ | $(CH_2)_2CH_2F$ | O |
| 121 | F | Cl | $OCH_2C\equiv CH$ | $(CH_2)_2CH_2F$ | O |
| 122 | Cl | Cl | $OCH_2CBr=CHBr$ | $n\text{-}C_3H_7$ | O |
| 123 | Cl | Cl | $OCH_2C_6H_5$ | $CH_2CH_2OH$ | O |
| 124 | Cl | Cl | $OCH(CH_3)CO_2C_2H_5$ | $n\text{-}C_3H_7$ | O |
| 125 | F | Br | $OCH_2C\equiv CH$ | $n\text{-}C_3H_7$ | O |
| 126 | Cl | Cl | $OCH(CH_3)CO_2C_2H_5$ | $(CH_2)_2CH_2F$ | O |
| 127 | Cl | Cl | $OCO_2C_2H_5$ | $(CH_2)_2CH_2F$ | O |
| 128 | F | Cl | $OCH(CH_3)CO_2C_2H_5$ | $(CH_2)_2CH_2F$ | O |
| 129 | Cl | Cl | $OCH(CH_3)C(O)CH_3$ | $(CH_2)_2CH_2F$ | O |
| 130 | Cl | Cl | $OCH(CH_3)CO_2CH(CH_3)_2$ | $(CH_2)_2CH_2F$ | O |
| 131 | Cl | Cl | $OCH_3$ | $CH_2CH_2C(O)H$ | O |
| 132 | Cl | Cl | $OCH(CH_3)CO_2CH_2CH_2F$ | $(CH_2)_2CH_2F$ | O |
| 133 | F | Cl | $OCH_2C\equiv Cl$ | $(CH_2)_2CH_2F$ | O |
| 134 | Cl | Cl | $OCH(CH_3)CO_2CH_2CF_3$ | $(CH_2)_2CH_2F$ | O |
| 135 | Cl | Cl | $OCH(CH_3)CO_2CH(CH_2F)_2$ | $(CH_2)_2CH_2F$ | O |
| 136 | Cl | Cl | $OCH(CH_3)CN$ | $(CH_2)_2CH_2F$ | O |
| 137 | F | Cl | $OCH(CH_3)CO_2C(CH_3)_3$ | $(CH_2)_2CH_2F$ | O |
| 138 | F | Cl | $OCH(CH_3)CO_2CH(CH_3)_2$ | $(CH_2)_2CH_2F$ | O |
| 139 | F | Cl | $OCH(CH_3)CN$ | $(CH_2)_2CH_2F$ | O |
| 140 | F | Cl | $OCH(CH_3)CO_2CH(C_2H_5)_2$ | $(CH_2)_2CH_2F$ | O |
| 141 | F | Cl | $OCH_2C\equiv CH$ | $(CH_2)_2CHF_2$ | O |
| 142 | F | Cl | $OCH(CH_3)CO_2CH(CH_3)CH(CH_3)_2$ | $(CH_2)_2CH_2F$ | O |
| 143 | F | Cl | $OCH(CH_3)_2$ | H | S |
| 144 | F | Cl | OH | $(CH_2)_2CH_2F$ | O |
| 145 | Cl | Cl | $OSO_2CF_3$ | $(CH_2)_2CH_2F$ | O |
| 146 | Cl | Cl | $OCH_3$ | $(CH_2)_2CHF_2$ | O |
| 147 | Cl | Cl | $NO_2$ | $n\text{-}C_3H_7$ | O |
| 148 | Cl | Cl | $OCH_3$ | $CH_2CH_2C(O)H$ | S |
| 149 | Cl | Cl | $OCH_3$ | $(CH_2)_2CHF_2$ | S |
| 150 | F | Cl | $OCH_2C_6H_5$ | $CH_2CH_2C(O)H$ | O |
| 151 | Cl | Cl | $OCH(CH_3)_2$ | $CH_2CH_2C(O)H$ | S |
| 152 | F | Cl | $OCH(CH_3)CO_2CH(CH_2F)_2$ | $(CH_2)_2CH_2F$ | O |
| 153 | F | Cl | $OCH(CH_3)CO_2CH[CH(CH_3)_2]_2$ | $(CH_2)_2CH_2F$ | O |
| 154 | F | Cl | $OCH(CH_3)CO_2N=C(CH_3)_2$ | $(CH_2)_2CH_2F$ | O |
| 155 | F | Cl | $OCH_2C_6H_5$ | $CH(CH_3)_2$ | O |
| 156 | F | Cl | $OCH(CH_3)_2$ | $CH_2CH_2C(O)H$ | S |
| 157 | F | Cl | $OCH_2C_6H_5$ | $CH_3$ | O |
| 158 | F | Cl | $OCH(CH_3)CO_2CH(CH_3)C_2H_5$ | $(CH_2)_2CH_2F$ | O |
| 159 | F | Cl | $OCH_2C\equiv CH$ | $CH(CH_3)_2$ | O |
| 160 | F | Cl | $OCH(CH_3)C(O)NH_2$ | $(CH_2)_2CH_2F$ | O |
| 161 | F | Cl | $OCH_2C\equiv CH$ | $CH_3$ | O |
| 162 | F | Cl | $OCH_2C_6H_5$ | $n\text{-}C_3H_7$ | O |
| 163 | Cl | Cl | $OCH(CH_3)COCH_3$ | $n\text{-}C_3H_7$ | O |
| 164 | F | Cl | $OCH(CH_3)CO_2CH(CH_2)_3CH_2$ | $(CH_2)_2CH_2F$ | O |
| 165 | F | Cl | $OCH(C_2H_5)CO_2CH(CH_3)_2$ | $(CH_2)CH_2F$ |  |
| 166 | F | Cl | $OCH(CH_3)CO_2CH(CH_3)C\equiv CH$ | $(CH_2)_2CH_2F$ | O |
| 167 | F | Cl | $OCH(CH_3)CO_2C(CH_3)_2C\equiv CH$ | $(CH_2)_2CH_2F$ | O |
| 168 | F | Cl | $OCH_2C\equiv CH$ | $n\text{-}C_4H_9$ | O |
| 169 | F | Cl | $OCH(CH_3)C\equiv CH$ | $(CH_2)_2CH_2F$ | O |
| 170 | Cl | Cl | $OCH(CH_3)C\equiv CH$ | $n\text{-}C_3H_7$ | O |
| 171 | F | Cl | $OCH(CH_3)CO_2CH_2CHCH_2CH_2$ | $(CH_2)_2CH_2F$ | O |
| 172 | F | Cl | $OCH(CH_3)_2$ | $(CH_2)_2CHF_2$ | S |
| 173 | F | Cl | $OCH_2C\equiv CH$ | $CH_2CHFCH_3$ | O |
| 174 | F | Cl | $OCH_2C\equiv CH$ | $(CH_2)_2CHF_2$ | S |
| 175 | F | Cl | $OCH(CH_3)CO_2CH(CH_3)_2$ | $(CH_2)_2CHF_2$ | S |
| 176 | F | Cl | $OCH_2C_6H_5$ | $CH_2C(O)CH_3$ | O |

TABLE 1-continued

Representative Compounds

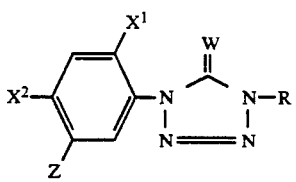

| Cpd No. | X¹ | X² | Z | R | W |
|---|---|---|---|---|---|
| 177 | F | Cl | OH | $(CH_2)_2CHF_2$ | S |
| 178 | F | Cl | $OCH_2C_6H_5$ | $CH_2CHFCH_3$ | O |
| 179 | F | Cl | $OCH(CH_3)CO_2H$ | H | O |
| 180 | F | Cl | $OCH_2C_6H_5$ | $CH(CH_3)C_2H_5$ | O |
| 181 | F | Cl | OH | $CH(CH_3)C_2H_5$ | O |
| 182 | F | Cl | $OCH(CH_3)CO_2H$ | $(CH_2)_2CH_2F$ | O |
| 183 | F | Cl | $OCH(CH_3)CO_2CH(CH_2OCH_3)_2$ | $(CH_2)_2CH_2F$ | O |
| 184 | F | Cl | $OCH(CH_3)CO_2C_3H_7$ | $(CH_2)_2CHF$ | O |
| 185 | F | Cl | $OCH_2C\equiv CH$ | $CH(CH_3)C_2H_5$ | O |
| 186 | F | Cl | $NO_2$ | H | O |
| 187 | F | Cl | H | $(CH_2)_2CH_2F$ | O |
| 188 | F | Cl | $OCH(CH_3)CO_2C(CH_3)_2CN$ | $(CH_2)_2CH_2F$ | O |
| 189 | F | Cl | $NO_2$ | $(CH_2)_2CH_2F$ | O |
| 190 | F | Cl | $OCH_2OCH_3$ | $(CH_2)_2CH_2F$ | O |
| 191 | F | Cl | $NHC(O)N(CH_3)_2$ | $(CH_2)_2CH_2F$ | O |
| 192 | F | Cl | $NHC(O)NHCH_2CH(CH_3)_2$ | $(CH_2)_2CH_2F$ | O |
| 193 | F | Cl | $OCH_2C\equiv CH$ | $CH_2OCH_3$ | O |
| 194 | F | Cl | (tetrahydrophthalimide ring) | $(CH_2)_2CH_2F$ | O |
| 195 | F | Cl | $N(SO_2CH_3)_2$ | $(CH_2)_2CH_2F$ | O |
| 196 | F | Cl | OH | $CH_2OCH_3$ | O |
| 197 | F | Cl | $OCH_2C_6H_5$ | $CH_2OCH_3$ | O |
| 198 | F | Cl | $OCH_2C_6H_5$ | $CH_2SCH_3$ | O |
| 199 | F | Cl | $OCH(CH_3)C(O)N(CH_2CH=CH_2)_2$ | $(CH_2)_2CH_2F$ | O |
| 200 | F | Cl | $N(CH_2CN)C(O)CH_3$ | $(CH_2)_2CH_2F$ | O |
| 201 | F | Cl | $N(C_2H_5)C(O)CH_3$ | $(CH_2)_2CH_2F$ | O |
| 202 | F | Cl | $NHC(O)CH_3$ | $(CH_2)_2CH_2F$ | O |
| 203 | F | Cl | $O(CH_2)_2OC_2H_5$ | $(CH_2)_2CH_2F$ | O |
| 204 | F | Cl | $OCH(CH_3)_2$ | $(CH_2)_2CH_2F$ | O |
| 205 | F | Cl | $OCH(CH_3)CH_2OCH_3$ | $(CH_2)_2CH_2F$ | O |
| 206 | F | Br | $OCH_2C\equiv CH$ | $(CH_2)_2CH_2F$ | O |
| 207 | F | Cl | $NH_2$ | $(CH_2)_2CH_2F$ | O |
| 208 | F | Cl | $OCH_2SCH_3$ | $(CH_2)_2CH_2F$ | O |
| 209 | F | Br | $OCH(CH_3)CO_2C(CH_3)_2C\equiv CH$ | $(CH_2)_2CH_2F$ | O |
| 210 | F | Br | OH | $(CH_2)_2CH_2F$ | O |
| 211 | F | Br | $OCH_2C_6H_5$ | H | O |
| 212 | F | Br | $OCH_2C_6H_5$ | $(CH_2)_2CH_2F$ | O |
| 213 | F | Cl | $OCH_2C_6H_5$ | $SCF_3$ | O |
| 214 | F | Cl | $OCH_2C_6H_5$ | $CH_2CN$ | O |
| 215 | F | Cl | $CH_3$ | $(CH_2)_2CH_2F$ | O |
| 216 | F | Cl | $OCH_2S(O)CH_3$ | $(CH_2)_2CH_2F$ | O |
| 217 | F | $NO_2$ | F | $(CH_2)_2CH_2F$ | O |
| 218 | F | Cl | (tetrahydrofuranyl-oxy) | $(CH_2)_2CH_2F$ | O |
| 219 | F | Cl | $O(CH_2)_2OCH_3$ | $(CH_2)_2CH_2F$ | O |
| 220 | F | $NO_2$ | $OCH_2C\equiv CH$ | $(CH_2)_2CH_2F$ | O |
| 221 | F | Cl | $OCH(CH_3)C(O)CH_3$ | $(CH_2)_2CH_2F$ | O |
| 222 | F | Cl | $OCH(CH_3)C(CH_3)=N-OH$ | $(CH_2)_2CH_2F$ | O |
| 223 | Cl | Cl | $NHCH_2CO_2C_2H_5$ | $n-C_3H_7$ | O |
| 224 | F | Br | $OCH_2OCH_3$ | $(CH_2)_2CH_2F$ | O |
| 225 | F | Br | $OCH(CH_3)C\equiv CH$ | $(CH_2)_2CH_2F$ | O |
| 226 | F | H | F | $(CH_2)_2CH_2F$ | O |
| 227 | F | $CH_3$ | $OCH_2C_6H_5$ | $(CH_2)_2CH_2F$ | O |
| 228 | F | $CH_3$ | OH | $(CH_2)_2CH_2F$ | O |
| 229 | F | $CH_3$ | $OCH_2C\equiv CH$ | $(CH_2)_2CH_2F$ | O |
| 230 | F | $CH_3$ | $OCH(CH_3)CO_2CH(CH_3)_2$ | $(CH_2)_2CH_2F$ | O |

TABLE 1-continued

Representative Compounds

| Cpd No. | X¹ | X² | Z | R | W |
|---|---|---|---|---|---|
| 231 | F | $C_2H_5$ | $OCH_2C_6H_5$ | $(CH_2)_2CH_2F$ | O |
| 232 | F | $C_2H_5$ | OH | $(CH_2)_2CH_2F$ | O |
| 233 | F | $C_2H_5$ | $OCH_2C\equiv CH$ | $(CH_2)_2CH_2F$ | O |
| 234 | F | $C_2H_5$ | $OCH(CH_3)CO_2CH(CH_3)_2$ | $(CH_2)_2CH_2F$ | O |
| 235 | F | Cl | $OCH_2C\equiv CH$ | $CH_2CF_2CH_3$ | O |
| 236 | F | Cl | $OCH(CH_3)CO_2CH(CH_3)_2$ | $CH_2CF_2CH_3$ | O |
| 237 | F | Cl | $SCH_2CN$ | $(CH_2)_2CH_2F$ | O |
| 238 | F | Cl | $SCH_2C\equiv CH$ | $(CH_2)_2CH_2F$ | O |
| 239 | F | Cl | $SCH(CH_3)CO_2CH(CH_3)_2$ | $(CH_2)_2CH_2F$ | O |
| 240 | F | Cl | $N(CH_3)(SO_2CH_3)$ | $(CH_2)_2CH_2F$ | O |
| 241 | F | Cl | $N(C_2H_5)(SO_2CH_3)$ | $(CH_2)_2CH_2F$ | O |
| 242 | F | Cl | $N(CH_3)_2$ | $(CH_2)_2CH_2F$ | O |
| 243 | F | Cl | $N(C_2H_5)_2$ | $(CH_2)_2CH_2F$ | O |
| 244 | F | Cl | $N(SO_2CF_3)_2$ | $(CH_2)_2CH_2F$ | O |
| 245 | F | Cl | $NHCO_2CH_3$ | $(CH_2)_2CH_2F$ | O |
| 246 | F | Cl | $NHCH_2C\equiv CH$ | $(CH_2)_2CH_2F$ | O |
| 247 | F | Cl | $NHCH(CH_3)CO_2C_2H_5$ | $(CH_2)_2CH_2F$ | O |
| 248 | F | Cl | $NHCH_2CO_2C_2H_5$ | $(CH_2)_2CH_2F$ | O |
| 249 | F | Cl | 2-oxopyrrolidin-1-yl | $(CH_2)_2CH_2F$ | |
| 250 | F | Cl | $N=C(CH_3)_2$ | $(CH_2)_2CH_2F$ | O |
| 251 | F | Cl | $N=CHCH_3$ | $(CH_2)_2CH_2F$ | O |
| 252 | F | Cl | $OCH(CH_3)OCH_3$ | $(CH_2)_2CH_2F$ | O |
| 253 | F | Cl | $OCH(CH_3)S(O)CH_3$ | $(CH_2)_2CH_2F$ | O |
| 254 | F | Cl | (1-oxotetrahydrothiophen-2-yl)oxy | $(CH_2)_2CH_2F$ | O |
| 255 | F | Cl | $OCH(CH_3)CON(CH_3)_2$ | $(CH_2)_2CH_2F$ | O |
| 256 | F | Cl | $OCH(CH_3)CONHS(O)_2$-(2-chlorophenyl) | $(CH_2)_2CH_2F$ | O |
| 257 | F | Cl | $OCH(CH_3)CONHS(O)_2CH_3$ | $(CH_2)_2CH_2F$ | O |
| 258 | $CF_3$ | Cl | $OCH_2C\equiv CH$ | $(CH_2)_3CH_2F$ | O |
| 259 | F | Cl | $OCH_2C\equiv CH$ | $(CH_2)_2CH_2F$ | S |
| 260 | F | Cl | $OC(CH_3)_2C\equiv CH$ | $(CH_2)_2CH_2F$ | O |
| 261 | F | Cl | $OCH_2C\equiv CH$ | $CH_2CH=CHF$ | O |
| 262 | F | Cl | CN | $(CH_2)_2CH_2F$ | O |
| 263 | F | Cl | $CO_2C_2H_5$ | $(CH_2)_2CH_2F$ | O |
| 264 | F | Cl | $CO_2H$ | $(CH_2)_2CH_2F$ | O |
| 265 | F | Cl | $SO_3H$ | $(CH_2)_2CH_2F$ | O |
| 266 | F | Cl | $SO_2N(C_2H_5)_2$ | $(CH_2)_2CH_2F$ | O |
| 267 | F | Cl | $SO_2NHC_6H_5$ | $(CH_2)_2CH_2F$ | O |
| 268 | F | Cl | $SO_2NH_2$ | $(CH_2)_2CH_2F$ | O |
| 269 | F | Cl | $CH(OC_2H_5)_2$ | $(CH_2)_2CH_2F$ | O |
| 270 | F | Cl | $C(CH_3)(OC_2H_5)_2$ | $(CH_2)_2CH_2F$ | O |
| 271 | F | Cl | $CH_2C\equiv CH$ | $(CH_2)_2CH_2F$ | O |
| 272 | F | Cl | H | $(CH_2)_2CH_2F$ | S |
| 273 | F | Cl | $OCH_2C_6H_5$ | H | O |
| 274 | Cl | Cl | $OCH_2C\equiv CH$ | $CH_2CH_2OCHF_2$ | O |
| 275 | F | Cl | $OCH_2C\equiv CH$ | $CH_2CH_2OCHF_2$ | O |
| 276 | Cl | Cl | $NH_2$ | $n-C_3H_7$ | O |
| 277 | Cl | Cl | $NHC(O)CH_3$ | $n-C_3H_7$ | O |
| 278 | F | Cl | $OCH_2C_6H_5$ | $(CH_2)_2CHF_2$ | O |

TABLE 1-continued

Representative Compounds

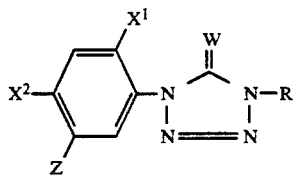

| Cpd No. | X¹ | X² | Z | R | W |
|---|---|---|---|---|---|
| 279 | F | Cl | OH | (CH$_2$)$_2$CHF$_2$ | O |
| 280 | Cl | Cl | OCH$_2$C≡CH | (CH$_2$)$_2$CHF$_2$ | S |
| 281 | F | Cl | OH | CH(CH$_3$)$_2$ | O |
| 282 | F | Cl | OH | CH$_3$ | O |
| 283 | F | Cl | OH | n-C$_3$H$_7$ | O |
| 284 | F | Cl | OCH$_2$C$_6$H$_5$ | CH$_2$CF$_2$CH$_3$ | O |
| 285 | F | Cl | OH | CH$_2$CF$_2$CH$_3$ | O |
| 286 | F | Cl | OH | (CH$_2$)$_2$CH$_2$F | S |
| 287 | F | Cl | OH | CH$_2$CHFCH$_3$ | O |
| 288 | F | Cl | OCH$_2$CO$_2$C$_2$H$_5$ | (CH$_2$)$_2$CH$_2$F | O |
| 289 | F | Cl | H | H | O |
| 290 | F | Cl | NCO | (CH$_2$)$_2$CH$_2$F | O |
| 291 | F | Cl | OH | CH$_2$SCH$_3$ | O |
| 292 | F | Cl | OCH$_2$C≡CH | CH$_2$SCH$_3$ | O |
| 293 | F | Cl | CH$_3$ | H | O |
| 294 | Cl | Cl | OCH$_2$C≡CH | CH$_2$CF$_2$CH$_3$ | O |
| 295 | F | H | F | H | O |
| 296 | F | Cl | OCH$_3$ | H | O |
| 297 | F | Cl | OCH$_2$C≡CBr | (CH$_2$)$_2$CH$_2$F | O |
| 298 | F | Cl | OCH$_2$CO$_2$Na | (CH$_2$)$_2$CH$_2$F | O |
| 299 | F | Cl | OCH(CH$_3$)CO$_2$K | (CH$_2$)$_2$CH$_2$F | O |
| 300 | F | Cl | OCH(CH$_3$)CO$_2$NH$_4$ | (CH$_2$)$_2$CH$_2$F | O |
| 301 | F | Cl | CO$_2$Na | (CH$_2$)$_2$CH$_2$F | O |
| 302 | F | Cl | SO$_3$Na | (CH$_2$)$_2$CH$_2$F | O |
| 303 | F | Cl | OCH(CH$_3$)CO$_2$H | (CH$_2$)$_2$CH$_2$F | O |
| 304 | F | Cl | OCH(CH$_3$)CH=CH$_2$ | (CH$_2$)$_2$CH$_2$F | O |
| 305 | F | Cl | SCH(CH$_3$)$_2$ | (CH$_2$)$_2$CH$_2$F | O |
| 306 | F | Cl | SCHF$_2$ | (CH$_2$)$_2$CH$_2$F | O |
| 307 | F | Cl | SCH$_2$C≡CI | (CH$_2$)$_2$CH$_2$F | O |
| 308 | F | Cl | SCH$_2$CF$_3$ | (CH$_2$)$_2$CH$_2$F | O |
| 309 | F | Cl | SCH$_2$OCH$_3$ | (CH$_2$)$_2$CH$_2$F | O |
| 310 | F | Cl | SCH$_2$SCH$_3$ | (CH$_2$)$_2$CH$_2$F | O |
| 311 | F | Cl | O(CH$_2$)$_2$F | (CH$_2$)$_2$CH$_2$F | O |
| 312 | F | Cl | O(CH$_2$)$_2$Br | (CH$_2$)$_2$CH$_2$F | O |
| 313 | F | Cl | OSO$_2$CH$_3$ | (CH$_2$)$_2$CH$_2$F | O |
| 314 | F | Cl | OSO$_2$CF$_3$ | (CH$_2$)$_2$CH$_2$F | O |
| 315 | F | Cl | OSO$_2$CH$_2$CH(CH$_3$)$_2$ | (CH$_2$)$_2$CH$_2$F | O |
| 316 | F | Cl | OSO$_2$CHCl$_2$ | (CH$_2$)$_2$CH$_2$F | O |
| 317 | F | Cl | OSO$_2$CH$_2$C$_6$H$_5$ | (CH$_2$)$_2$CH$_2$F | O |
| 318 | F | Cl | OSO$_2$CH$_2$CN | (CH$_2$)$_2$CH$_2$F | O |
| 319 | F | Cl | OSO$_2$CH$_2$C≡CH | (CH$_2$)$_2$CH$_2$F | O |
| 320 | F | Cl | OSO$_2$CH$_2$C≡CI | (CH$_2$)$_2$CH$_2$F | O |
| 321 | F | Cl | OSO$_2$NHCH$_3$ | (CH$_2$)$_2$CH$_2$F | O |
| 322 | F | Cl | OSO$_2$(CH$_2$)$_2$N(CH$_3$)$_2$ | (CH$_2$)$_2$CH$_2$F | O |
| 323 | F | Cl | OSO$_2$(CH$_2$)$_2$SCH$_2$CH=CH$_2$ | (CH$_2$)$_2$CH$_2$F | O |
| 324 | F | Cl | OSO$_2$(CH$_2$)$_2$OCH$_2$C≡CH | (CH$_2$)$_2$CH$_2$F | O |
| 325 | F | Cl | OSO$_2$(CH$_2$)$_2$OCH$_2$CO$_2$CH$_3$ | (CH$_2$)$_2$CH$_2$F | O |
| 326 | F | Cl | OSO$_2$(CH$_2$)$_2$OCH$_2$CO$_2$H | (CH$_2$)$_2$CH$_2$F | O |
| 327 | F | Cl | OSO$_2$(CH$_2$)$_2$OCH(CH$_3$)CO$_2$Na | (CH$_2$)$_2$CH$_2$F | O |
| 328 | F | Cl | OSO$_2$(CH$_2$)$_2$SCH(CH$_3$)CO$_2$CH$_3$ | (CH$_2$)$_2$CH$_2$F | O |
| 329 | F | Cl | SCH$_2$CO$_2$H | (CH$_2$)$_2$CH$_2$F | O |
| 330 | F | Cl | SCH$_2$CO—SCH$_3$ | (CH$_2$)$_2$CH$_2$F | O |
| 331 | F | Cl | OCH(CH$_3$)CO$_2$CH$_2$CH=CH$_2$ | (CH$_2$)$_2$CH$_2$F | O |
| 332 | F | Cl | OCHFCO$_2$H | (CH$_2$)$_2$CH$_2$F | O |
| 333 | F | Cl | SCH$_2$CO$_2$N=C(CH$_3$)$_2$ | (CH$_2$)$_2$CH$_2$F | O |
| 334 | F | Cl | OCHFCO$_2$N=C(SCH$_3$)(CH$_3$) | (CH$_2$)$_2$CH$_2$F | O |
| 335 | F | Cl | OCH(CH$_3$)CO$_2$N=C(SCH$_3$)(CH$_3$) | (CH$_2$)$_2$CH$_2$F | O |
| 336 | F | Cl | OCH(CH$_3$)CO$_2$N=C(CH$_3$)(C$_2$H$_5$) | (CH$_2$)$_2$CH$_2$F | O |
| 337 | F | Cl | OCH$_2$CO$_2$N=C(CH$_3$)$_2$ | (CH$_2$)$_2$CH$_2$F | O |
| 338 | F | Cl | SCH(CH$_3$)C(CH$_3$)=NOH | (CH$_2$)$_2$CH$_2$F | O |
| 339 | F | Cl | OCH$_2$C(CH$_3$)=NOH | (CH$_2$)$_2$CH$_2$F | O |
| 340 | F | Cl | SCH(CH$_3$)C(CH$_3$)=N—OCH$_3$ | (CH$_2$)$_2$CH$_2$F | O |
| 341 | F | Cl | OCH(CH$_3$)C(CH$_3$)=N—OCH(CH$_3$)$_2$ | (CH$_2$)$_2$CH$_2$F | O |
| 342 | F | Cl | SCH(CH$_3$)COCH$_3$ | (CH$_2$)$_2$CH$_2$F | O |
| 343 | F | Cl | OCH$_2$COCH$_3$ | (CH$_2$)$_2$CH$_2$F | O |
| 344 | F | Cl | SCH$_2$COCH$_3$ | (CH$_2$)$_2$CH$_2$F | O |
| 345 | F | Cl | N=C(SCH$_3$)(CH$_3$) | (CH$_2$)$_2$CH$_2$F | O |
| 346 | F | Cl | CO—SCH$_3$ | (CH$_2$)$_2$CH$_2$F | O |
| 347 | F | Cl | CONH$_2$ | (CH$_2$)$_2$CH$_2$F | O |
| 348 | F | Cl | CONHCH$_3$ | (CH$_2$)$_2$CH$_2$F | O |

TABLE 1-continued
Representative Compounds

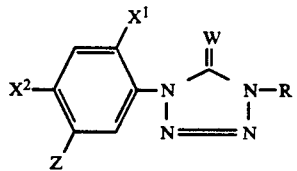

| Cpd No. | X$^1$ | X$^2$ | Z | R | W |
|---|---|---|---|---|---|
| 349 | F | Cl | CON(C$_2$H$_5$)$_2$ | (CH$_2$)$_2$CH$_2$F | O |
| 350 | F | Cl | CONHC$_6$H$_5$ | (CH$_2$)$_2$CH$_2$F | O |
| 351 | F | Cl | OCH$_2$C≡CH | SCF$_3$ | O |
| 352 | F | CH$_2$F | OCH$_2$C≡CH | (CH$_2$)$_2$CH$_2$F | O |
| 353 | F | Cl | CF$_3$ | (CH$_2$)$_2$CH$_2$F | O |

Other representative compounds are those which are identical with compounds 1-353 respectively except that X$^2$ is CF$_3$. Still other representative compounds are those which are identical with compounds 1-353 respectively except that X$^1$ is Br.

TABLE 2

| Compound No. | mp (°C.) | Empirical Formula | Elemental Analysis C | H | N |
|---|---|---|---|---|---|
| 1 | 89-90 | C$_{10}$H$_9$Cl$_3$N$_4$O | C 39.05 | 2.95 | 18.22 |
| | | | F 39.13 | 3.22 | 17.80 |
| 2 | 100-101 | C$_{10}$H$_7$Cl$_3$N$_4$O | C 39.31 | 2.31 | 18.34 |
| | | | F 40.38 | 2.64 | 18.33 |
| 3 | 114-115 | C$_9$H$_7$Cl$_3$N$_4$O$_2$ | C 34.92 | 2.28 | 18.10 |
| | | | F 36.01 | 2.59 | 17.91 |
| 4 | 47-48 | C$_{11}$H$_{12}$Cl$_2$N$_4$O | C | | |
| | | | F | | |
| 5 | 55-57 | C$_{11}$H$_{10}$Cl$_2$N$_4$O | C | | |
| | | | F | | |
| 6 | 158-159 | C$_9$H$_8$Cl$_2$N$_4$O$_2$ | C 39.29 | 2.93 | 20.37 |
| | | | F 39.35 | 3.14 | 20.30 |
| 7 | 99-100 | C$_{10}$H$_{10}$Cl$_2$N$_4$O$_2$ | C 41.54 | 3.49 | 19.38 |
| | | | F 42.55 | 3.50 | 16.91 |
| 8 | 59-60 | C$_{10}$H$_{10}$F$_2$O$_2$N$_4$ | C | | |
| | | | F | | |
| 9 | 86-87 | C$_{11}$H$_{12}$Cl$_2$N$_4$O$_2$ | C 43.57 | 3.99 | 18.48 |
| | | | F 44.40 | 4.02 | 16.35 |
| 10 | 65-67 | C$_{11}$H$_{12}$F$_2$N$_4$O$_2$ | C | | |
| | | | F | | |
| 11 | 60-62 | C$_{11}$H$_{12}$ClFN$_4$O$_2$ | C | | |
| | | | F | | |
| 12 | 89-90 | C$_{11}$H$_{12}$BrClN$_4$O$_2$ | C 38.00 | 3.48 | 16.11 |
| | | | F 38.07 | 3.41 | 15.96 |
| 13 | 65-67 | C$_{11}$H$_{12}$BrClN$_4$O$_2$ | C | | |
| 14 | 54-56 | C$_{12}$H$_{14}$Cl$_2$N$_4$O$_2$ | C | | |
| | | | F | | |
| 15 | 81-85 | C$_{11}$H$_{12}$Cl$_2$N$_4$O$_2$ | C | | |
| | | | F | | |
| 16 | 58-59 | C$_{12}$H$_{14}$Cl$_2$N$_4$O$_2$ | C 45.44 | 4.45 | 17.66 |
| | | | F 45.51 | 4.28 | 17.17 |
| 17 | 144-145 | C$_9$H$_6$Cl$_2$F$_2$N$_4$O$_2$ | C 34.75 | 1.95 | 18.01 |
| | | | F 34.97 | 2.14 | 18.01 |
| 18 | 110-111 | C$_{10}$H$_9$Cl$_2$FN$_4$O$_2$ | C 39.11 | 2.95 | 18.24 |
| | | | F 39.10 | 2.90 | 18.18 |
| 19 | 80-81 | C$_{11}$H$_{11}$Cl$_2$FN$_4$O$_2$ | C 41.14 | 3.45 | 17.44 |
| | | | F 41.39 | 3.36 | 16.64 |
| 20 | 107-108 | C$_{11}$H$_{10}$Cl$_2$N$_4$O$_2$ | C 43.87 | 3.35 | 18.61 |
| | | | F 43.95 | 3.40 | 17.05 |
| 21 | 103-104 | C$_{12}$H$_{12}$Cl$_2$N$_4$O$_2$ | C 45.73 | 3.84 | 17.78 |
| | | | F 45.99 | 3.85 | 15.99 |
| 22 | 108-109 | C$_{11}$H$_{12}$Cl$_2$N$_4$O$_3$ | C 41.39 | 3.79 | 17.56 |
| | | | F 43.97 | 4.04 | 14.24 |
| 23 | 86-87 | C$_{11}$H$_{12}$Cl$_2$N$_4$O$_2$ | C 43.58 | 4.00 | 18.48 |
| | | | F 43.51 | 4.02 | 18.28 |
| 24 | oil | C$_{13}$H$_{16}$Cl$_2$N$_4$O$_2$ | C 47.14 | 4.87 | 16.91 |
| | | | F 47.40 | 4.94 | 15.75 |
| 25 | 85-86 | C$_{13}$H$_{14}$Cl$_2$N$_4$O$_2$ | C 47.43 | 4.29 | 17.02 |
| | | | F 47.66 | 4.35 | 17.02 |
| 26 | oil | C$_{13}$H$_{16}$Cl$_2$N$_4$O$_2$ | C 47.14 | 4.87 | 16.91 |
| | | | F 47.77 | 4.99 | 15.05 |
| 27 | oil | C$_{13}$H$_{14}$Cl$_2$N$_4$O$_2$ | C 47.43 | 4.29 | 17.02 |
| | | | F 47.72 | 4.15 | 15.80 |
| 28 | oil | C$_{13}$H$_{14}$Br$_2$N$_4$O$_2$ | C 37.34 | 3.38 | 13.40 |
| | | | F 37.51 | 3.48 | 13.32 |
| 29 | 94-95 | C$_{12}$H$_{14}$Br$_2$N$_4$O$_3$ | C 34.15 | 3.34 | 13.28 |
| | | | F 34.28 | 3.41 | 13.28 |
| 30 | 71-72 | C$_{14}$H$_{18}$Cl$_2$N$_4$O$_2$ | C 48.79 | 5.26 | 16.23 |
| | | | F 50.48 | 5.91 | 16.71 |
| 31 | 74-75 | C$_{12}$H$_{13}$Cl$_2$FN$_4$O$_2$ | C 43.00 | 3.91 | 16.72 |
| | | | F 42.93 | 3.84 | 16.71 |
| 32 | 78-79 | C$_{13}$H$_{15}$Cl$_2$FN$_4$O$_2$ | C 44.71 | 4.33 | 16.05 |
| | | | F 44.72 | 4.28 | 15.83 |
| 33 | oil | C$_{11}$H$_{10}$Cl$_2$F$_2$N$_4$O$_2$ | C | | |
| | | | F | | |
| 34 | 83-84 | C$_{12}$H$_{11}$Cl$_2$F$_3$N$_4$O$_2$ | C 38.83 | 2.99 | 15.10 |
| | | | F 38.84 | 2.90 | 14.99 |
| 35 | 77-78 | C$_{13}$H$_{16}$F$_2$N$_4$O$_2$ | C 52.34 | 5.41 | 18.77 |
| | | | F 52.38 | 5.18 | 18.71 |
| 36 | 49-50 | C$_{13}$H$_{16}$BrClN$_4$O$_2$ | C 41.56 | 4.29 | 14.92 |
| | | | F 42.02 | 4.22 | 14.73 |
| 37 | 51-52 | C$_{14}$H$_{18}$Cl$_2$N$_4$O$_2$ | C 48.70 | 5.26 | 16.23 |
| | | | F 48.79 | 5.16 | 16.09 |
| 38 | 87-88 | C$_{12}$H$_{14}$Cl$_2$N$_4$O$_3$ | C 43.26 | 4.24 | 16.82 |
| | | | F 43.63 | 4.29 | 16.86 |
| 39 | 57-58 | C$_{13}$H$_{14}$Cl$_2$N$_4$O$_2$ | C 47.43 | 4.29 | 17.02 |
| | | | F 47.49 | 4.50 | 16.86 |
| 40 | 56-57 | C$_{13}$H$_{13}$Cl$_3$N$_4$O$_2$ | C 42.94 | 3.60 | 15.41 |
| | | | F 43.65 | 3.68 | 14.96 |
| 41 | 155 | C$_{11}$H$_8$Cl$_2$N$_4$O$_2$ | C 44.17 | 2.69 | 18.73 |
| | | | F 44.33 | 2.88 | 18.55 |
| 42 | 120-121 | C$_{12}$H$_{10}$Cl$_2$N$_4$O$_2$ | C 46.03 | 3.22 | 17.89 |
| | | | F 46.60 | 3.20 | 16.37 |
| 43 | 71-72 | C$_{12}$H$_{10}$F$_2$N$_4$O$_2$ | C 51.43 | 3.59 | 19.99 |
| | | | F 51.74 | 3.47 | 19.95 |
| 44 | 88-89 | C$_{12}$H$_{10}$FClN$_4$O$_2$ | C 48.58 | 3.39 | 18.88 |
| | | | F 48.70 | 3.37 | 18.90 |
| 45 | 70-72 | C$_{13}$H$_{12}$Cl$_2$N$_4$O$_2$ | C | | |
| | | | F | | |
| 46 | oil | C$_{13}$H$_{12}$F$_2$N$_4$O$_2$ | C | | |
| | | | F | | |
| 47 | 72-73 | C$_{13}$H$_{12}$ClFO$_2$N$_4$ | C 50.25 | 3.89 | 18.03 |
| | | | F 50.21 | 3.79 | 17.97 |
| 48 | 60-62 | C$_{13}$H$_{12}$ClFN$_4$O$_2$ | C | | |
| | | | F | | |
| 49 | 87-88 | C$_{13}$H$_{12}$BrClN$_4$O$_2$ | C 42.01 | 3.26 | 15.08 |
| | | | F 41.94 | 3.34 | 14.96 |
| 50 | 70-71 | C$_{13}$H$_{12}$BrClN$_4$O$_2$ | C | | |
| | | | F | | |
| 51 | 120-121 | C$_{13}$H$_{12}$Cl$_2$N$_4$O$_2$ | C 47.72 | 3.70 | 17.12 |
| | | | F 47.67 | 3.32 | 16.70 |
| 52 | 73-74 | C$_{14}$H$_{14}$Cl$_2$N$_4$O$_2$ | C 49.27 | 4.14 | 16.42 |
| | | | F 50.04 | 3.94 | 15.07 |
| 53 | 90-91 | C$_{14}$H$_{14}$Cl$_2$N$_4$O$_2$ | C 49.28 | 4.14 | 16.42 |
| | | | F 49.22 | 3.96 | 15.65 |
| 54 | 63-65 | C$_{11}$H$_6$Cl$_2$F$_2$N$_4$O$_2$ | C | | |

TABLE 2-continued

| Compound No. | mp (°C.) | Empirical Formula | Elemental Analysis C | H | N |
|---|---|---|---|---|---|
| 55 | 118–120 | $C_{12}H_9Cl_2FN_4O_2$ | C 44.53<br>F 43.52 | 2.69<br>2.74 | 16.69<br>16.92 |
| 56 | 86–87 | $C_{13}H_{11}Cl_2FN_4O_2$ | C 45.54<br>F 45.23 | 3.15<br>3.21 | 16.05<br>16.23 |
| 57 | oil | $C_{13}H_{11}BrCl_2N_4O_2$ | C 38.44<br>F 39.40 | 2.73<br>2.83 | 13.80<br>13.03 |
| 58 | 115–116 | $C_{12}H_8Cl_2N_4O_2$ | C 46.24<br>F 47.12 | 2.59<br>2.83 | 17.98<br>16.93 |
| 59 | 127–128 | $C_{12}H_{10}Cl_2N_4O_3$ | C 43.79<br>F 44.42 | 3.06<br>3.01 | 17.02<br>17.03 |
| 60 | 79–80 | $C_{13}H_{12}Cl_2N_4O_3$ | C 45.50<br>F 45.84 | 3.52<br>3.18 | 16.32<br>17.07 |
| 61 | 134–138 | $C_{13}H_{11}Cl_2IN_4O_2$ | C 34.46<br>F 34.85 | 2.45<br>2.46 | 12.37<br>12.37 |
| 62 | 58–60 | $C_{14}H_{14}Cl_2N_4O_2$ | C<br>F | | |
| 63 | oil | $C_{12}H_{11}Cl_2N_5O_2$ | C 43.92<br>F 43.48 | 3.38<br>3.37 | 21.34<br>19.09 |
| 64 | oil | $C_{13}H_{13}Cl_2N_5O_2$ | C 45.63<br>F 45.66 | 3.82<br>3.72 | 20.46<br>20.10 |
| 65 | oil | $C_{15}H_{17}Cl_2N_5O_2$ | C<br>F | | |
| 66 | 112–113 | $C_{11}H_{12}Cl_2N_4O_3$ | C 41.39<br>F 42.09 | 3.79<br>3.81 | 17.56<br>17.35 |
| 67 | 76–77 | $C_{12}H_{14}Cl_2N_4O_3$ | C 43.26<br>F 43.73 | 4.23<br>3.97 | 16.82<br>16.82 |
| 68 | oil | $C_{12}H_{14}F_4N_4O_3$ | C 47.99<br>F 48.21 | 4.70<br>4.72 | 18.66<br>18.08 |
| 69 | oil | $C_{12}H_{14}ClFN_4O_3$ | C<br>F | | |
| 70 | 72–73 | $C_{12}H_{14}BrClN_4O_3$ | C 38.16<br>F 38.14 | 3.74<br>3.88 | 14.84<br>14.95 |
| 71 | 60–61 | $C_{13}H_{16}Cl_2N_4O_3$ | C 44.90<br>F 45.20 | 4.64<br>4.52 | 16.13<br>15.89 |
| 72 | — | $C_{12}H_{13}Cl_2FN_4O_3$ | C 41.04<br>F 35.44 | 3.73<br>3.12 | 15.96<br>11.49 |
| 73 | 60–61 | $C_{14}H_{18}Cl_2N_4O_3$ | C 46.42<br>F 46.44 | 5.29<br>4.93 | 15.47<br>15.06 |
| 74 | 63–64 | $C_{14}H_{13}BrClN_4O_3$ | C 41.45<br>F 41.47 | 4.47<br>4.56 | 13.81<br>13.71 |
| 75 | 87–88 | $C_{14}H_{16}Cl_2N_4O_3$ | C 46.81<br>F 46.95 | 4.49<br>4.39 | 15.60<br>15.60 |
| 76 | 89–90 | $C_{14}H_{16}Cl_2N_4O_3$ | C 46.81<br>F 47.00 | 4.49<br>4.20 | 15.60<br>15.44 |
| 77 | 81–82 | $C_{15}H_{18}Cl_2N_4O_3$ | C 48.26<br>F 48.47 | 4.86<br>4.84 | 15.01<br>15.06 |
| 78 | 99–101 | $C_{14}H_{16}Cl_2N_4O_4$ | C 44.81<br>F 44.93 | 4.30<br>4.32 | 14.93<br>14.58 |
| 79 | 83–84 | $C_{15}H_{18}Cl_2N_4O_3$ | C 48.27<br>F 48.44 | 4.86<br>4.85 | 15.01<br>14.78 |
| 80 | oil | $C_{15}H_{18}Cl_2N_4O_4$ | C<br>F | | |
| 81 | 91–92 | $C_{12}H_{12}Cl_2N_4O_3$ | C 43.52<br>F 43.58 | 3.65<br>3.76 | 16.91<br>16.83 |
| 82 | 134–136 | $C_{12}H_{12}Cl_2N_4O_4$ | C<br>F | | |
| 83 | 76–78 | $C_{13}H_{14}Cl_2N_4O_4$ | C<br>F | | |
| 84 | 80–81 | $C_{14}H_{16}Cl_2N_4O_4$ | C 44.81<br>F 45.45 | 4.30<br>4.22 | 14.93<br>13.48 |
| 85 | 58–59 | $C_{12}H_{14}Cl_2N_4O_2S$ | C 41.28<br>F 41.63 | 4.04<br>3.86 | 16.05<br>16.07 |
| 86 | 64–65 | $C_{11}H_{12}Cl_2N_4O_4S$ | C 35.98<br>F 36.37 | 3.29<br>3.28 | 15.25<br>14.55 |
| 87 | 75–76 | $C_{11}H_{12}BrClN_4O_4S$ | C 32.09<br>F 32.15 | 2.94<br>2.84 | 13.61<br>13.59 |
| 88 | 60–61 | $C_{13}H_{16}Cl_2N_4O_4S$ | C 39.50<br>F 39.76 | 4.08<br>4.00 | 14.17<br>13.98 |
| 89 | 52–53 | $C_{11}H_9Cl_2F_3N_4O_4S$ | C 31.37<br>F 31.76 | 2.15<br>2.13 | 13.31<br>13.38 |
| 90 | 74–75 | $C_{12}H_{15}ClN_4O_2$ | C 50.97<br>F 51.04 | 5.35<br>5.40 | 19.82<br>19.77 |
| 91 | 67–68 | $C_{14}H_{19}ClN_4O_2$ | C 54.10<br>F 54.39 | 6.16<br>6.22 | 18.03<br>17.95 |
| 92 | 89–90 | $C_{14}H_{15}ClN_4O_2$ | C 54.81<br>F 54.70 | 4.93<br>4.97 | 18.27<br>18.15 |
| 93 | 50–51 | $C_{15}H_{21}ClN_4O_3$ | C 52.86<br>F 53.20 | 6.21<br>6.33 | 16.44<br>16.29 |
| 94 | 82–83 | $C_{12}H_{12}ClF_3N_4O_2$ | C 42.81<br>F 42.05 | 3.59<br>3.42 | 16.63<br>16.02 |
| 95 | 59–60 | $C_{12}H_{15}ClN_4O_2$ | C<br>F | | |
| 96 | 65–66 | $C_{12}H_{13}ClN_4O_2$ | C<br>F | | |
| 97 | 100–101 | $C_{14}H_{15}ClN_4O_2$ | C<br>F | | |
| 98 | 129–130 | $C_{14}H_{13}ClN_4O_2$ | C<br>F | | |
| 99 | oil | $C_{13}H_{17}ClN_4O_3$ | C<br>F | | |
| 100 | oil | $C_{13}H_{16}Cl_2N_4O_2$ | C 47.14<br>F 48.14 | 4.87<br>4.84 | 16.91<br>15.01 |
| 101 | 68–69 | $C_{12}H_{14}Cl_2N_4O_3$ | C 43.26<br>F 43.68 | 4.24<br>4.36 | 16.81<br>16.31 |
| 102 | 170–171 | $C_{14}H_{16}BrClN_4O_3$ | C 41.66<br>F 41.66 | 3.99<br>3.79 | 13.87<br>13.69 |
| 103 | 83–84 | $C_{15}H_{18}BrClN_4O_3$ | C 43.13<br>F 43.12 | 4.34<br>4.04 | 13.41<br>13.25 |
| 104 | 142–143 | $C_{10}H_8Cl_2N_4O_2$ | C 41.83<br>F 41.70 | 2.81<br>2.72 | 19.51<br>19.51 |
| 105 | 79–80 | $C_{10}H_{10}ClFN_4O_2$ | C<br>F | | |
| 106 | 85–86 | $C_{11}H_{12}ClFN_4O_2$ | C<br>F | | |
| 107 | 68–70 | $C_{14}H_{18}BrClN_4O_2$ | C<br>F | | |
| 108 | oil | $C_{14}H_{16}ClF_3N_4O_2$ | C 46.10<br>F 45.33 | 4.41<br>4.41 | 15.35<br>14.12 |
| 109 | 40–41 | $C_{10}H_{10}Cl_2N_4O$ | C 43.95<br>F 44.42 | 3.69<br>3.84 | 20.52<br>20.34 |
| 110 | 58–59 | $C_{10}H_{10}Cl_2N_4O$ | C 43.95<br>F 43.64 | 3.69<br>3.69 | 20.52<br>20.37 |
| 111 | 116–117 | $C_9H_8Cl_2N_4O_2$ | C 39.27<br>F 39.29 | 2.93<br>2.90 | 20.37<br>20.45 |
| 112 | 99–100 | $C_9H_8Cl_2N_4OS$ | C 37.12<br>F 37.15 | 2.77<br>2.82 | 19.24<br>18.96 |
| 113 | 49–50 | $C_{10}H_8Cl_2N_4O$ | C 44.30<br>F 44.73 | 2.97<br>3.07 | 20.66<br>20.50 |
| 114 | 121–122 | $C_9H_5Cl_2N_5O$ | C 40.02<br>F 40.28 | 1.87<br>1.79 | 25.93<br>25.98 |
| 115 | 104–105 | $C_{13}H_{11}ClFIN_4O_2$ | C 35.76<br>F 38.87 | 2.54<br>3.03 | 12.83<br>12.84 |
| 116 | 90–91 | $C_{12}H_{10}ClFN_4O_2$ | C 48.58<br>F 49.30 | 3.40<br>3.49 | 18.89<br>18.80 |
| 117 | 45–46 | $C_{13}H_{15}Cl_2N_4O_3F$ | C 42.75<br>F 43.37 | 4.15<br>4.30 | 15.34<br>15.85 |
| 118 | 70–72 | $C_{10}H_{10}ClFN_4O_2$ | C<br>F | | |
| 119 | 154–155 | $C_{17}H_{14}Cl_2N_4O_3$ | C<br>F | | |
| 120 | 78–79 | $C_{17}H_{15}ClF_2N_4O_2$ | C<br>F | | |
| 121 | 49–51 | $C_{13}H_{11}ClF_2N_4O_2$ | C 47.50<br>F 47.85 | 3.38<br>3.38 | 17.04<br>16.40 |
| 122 | 64–65 | $C_{13}H_{12}Br_2Cl_2N_2O_2$ | C 32.06<br>F 31.93 | 2.48<br>2.53 | 11.51<br>11.27 |
| 123 | 117–118 | $C_{16}H_{14}Cl_2N_4O_3$ | C<br>F | | |
| 124 | oil | $C_{15}H_{18}Cl_2N_4O_4$ | C 46.28<br>F 48.50 | 4.67<br>5.49 | 14.39<br>11.68 |
| 125 | oil | $C_{13}H_{12}BrFN_4O_2$ | C<br>F | | |
| 126 | oil | $C_{15}H_{17}Cl_2FN_4O_4$ | C 44.24<br>F 46.66 | 4.21<br>4.87 | 13.76<br>12.32 |
| 127 | oil | $C_{13}H_{13}Cl_2FN_4O_4$ | C 41.18<br>F 41.70 | 3.46<br>3.52 | 14.78<br>14.53 |
| 128 | oil | $C_{15}H_{17}ClF_2N_4O_4$ | C 46.10<br>F 46.95 | 4.64<br>4.16 | 14.34<br>13.65 |
| 129 | oil | $C_{14}H_{15}Cl_2FN_4O_3$ | C 44.58<br>F 44.89 | 4.01<br>3.93 | 14.85<br>14.05 |
| 130 | oil | $C_{16}H_{19}Cl_2FN_4O_4$ | C 45.62<br>F 45.95 | 4.55<br>4.56 | 13.30<br>12.98 |
| 131 | 73–74 | $C_{11}H_{10}Cl_2N_4O_3$ | C 41.66<br>F 42.10 | 3.18<br>3.25 | 17.67<br>16.87 |
| 132 | oil | $C_{15}H_{16}Cl_2F_2N_4O_4$ | C 42.37<br> | 3.79<br> | 13.18<br> |

TABLE 2-continued

| Compound No. | mp (°C.) | Empirical Formula | Elemental Analysis C | H | N |
|---|---|---|---|---|---|
| 133 | 120–123 | C₁₃H₁₀ClF₂IN₄O₂ | F 42.97 C 34.12 F 34.96 | 4.10 2.20 2.35 | 10.89 12.24 11.78 |
| 134 | oil | C₁₅H₁₄Cl₂F₂O₄N₄ | C 39.06 F 39.43 | 3.06 2.99 | 12.14 11.26 |
| 135 | oil | C₁₆H₁₇Cl₂F₃N₄O₄ | C 42.03 F 41.90 | 3.75 3.59 | 12.25 11.60 |
| 136 | oil | C₁₃H₁₂Cl₂FN₅O₂ | C 43.35 F 43.42 | 3.36 3.14 | 19.45 18.30 |
| 137 | oil | C₁₇H₂₁ClF₂N₄O₄ | C 48.75 F 48.55 | 5.06 5.01 | 13.38 12.52 |
| 138 | oil | C₁₆H₁₉ClF₂N₄O₄ | C 47.47 F 47.73 | 4.74 4.69 | 13.84 13.48 |
| 139 | oil | C₁₃H₁₂ClF₂N₅O₂ | C 45.42 F 47.42 | 3.52 3.88 | 20.37 18.90 |
| 140 | oil | C₁₈H₂₃ClF₂N₄O₄ | C 49.94 F 50.64 | 5.36 5.75 | 12.94 12.28 |
| 141 | 44–47 | C₁₃H₁₀ClF₃N₄O₂ | C F | | |
| 142 | oil | C₁₈H₂₃ClF₂N₄O₄ | C 49.94 F 49.65 | 5.36 5.26 | 12.94 12.54 |
| 143 | 134–135 | C₁₀H₁₀ClFN₄OS | C F | | |
| 144 | 83–85 | C₁₀H₉ClF₂N₄O₂ | C F | | |
| 145 | oil | C₁₁H₈Cl₂F₄N₄O₄S | C 30.08 F 30.89 | 1.84 1.89 | 12.76 12.49 |
| 146 | 81–82 | C₁₁H₁₀Cl₂F₂N₄O₂ | C F | | |
| 147 | 77–78 | C₁₀H₉Cl₂N₅O₃ | C F | | |
| 148 | 80–83 | C₁₁H₁₀Cl₂N₄O₂S | C F | | |
| 149 | 81–83 | C₁₁H₁₀Cl₂F₂N₄OS | C F | | |
| 150 | 83–84 | C₁₇H₁₄ClFN₄O₃ | C F | | |
| 151 | oil | C₁₅H₁₇Cl₂N₃O₂S | C F | | |
| 152 | oil | C₁₆H₁₇ClF₄N₄O₄ | C 43.60 F 44.72 | 3.88 3.90 | 12.70 12.08 |
| 153 | oil | C₂₀H₂₇ClF₂N₄O₄ | C 52.11 F 52.76 | 5.91 5.83 | 12.16 11.37 |
| 154 | oil | C₁₆H₁₈ClF₂N₅O₄ | C 46.00 F 46.70 | 4.34 4.26 | 16.79 15.37 |
| 155 | oil | C₁₇H₁₆ClFN₄O₂ | C F | | |
| 156 | oil | C₁₃H₁₄ClFN₄O₂S | C F | | |
| 157 | 93–95 | C₁₅H₁₂ClFN₄O₂ | C F | | |
| 158 | oil | C₁₇H₂₁ClF₂N₄O₄ | C 48.74 F 48.57 | 5.05 4.76 | 13.38 13.10 |
| 159 | oil | C₁₃H₁₂ClFN₄O₂ | C F | | |
| 160 | oil | C₁₃H₁₄ClFN₅O₃ | C F | | |
| 161 | 137–138 | C₁₁H₈ClFN₄O₂ | C 46.74 F 47.14 | 2.85 2.93 | 19.82 19.77 |
| 162 | oil | C₁₈H₁₈ClN₄O₂ | C F | | |
| 163 | 52–54 | C₁₄H₁₆Cl₂N₄O₃ | C F | | |
| 164 | oil | C₁₈H₂₁ClF₂N₄O₄ | C 50.18 F 52.44 | 4.91 5.27 | 13.00 11.26 |
| 165 | oil | C₁₇H₂₁ClF₂N₄O₄ | C 48.74 F 49.10 | 5.05 5.26 | 13.38 13.20 |
| 166 | oil | C₁₇H₁₇ClF₂N₄O₄ | C 49.22 F 49.49 | 4.13 4.02 | 13.51 13.19 |
| 167 | oil | C₁₈H₁₉ClF₂N₄O₄ | C 50.41 F 53.62 | 4.47 4.68 | 13.07 10.98 |
| 168 | 58–59 | C₁₄H₁₄ClFN₄O₂ | C 51.78 F 51.91 | 4.35 4.41 | 17.25 17.22 |
| 169 | 78–79 | C₁₄H₁₃ClF₂N₄O₂ | C F | | |
| 170 | 80–81 | C₁₄H₁₄Cl₂N₄O₂ | C 49.28 F 49.45 | 4.14 4.19 | 16.42 16.59 |
| 171 | oil | C₁₇H₁₉ClF₂N₄O₄ | C 48.98 | 4.60 | 13.44 |
| 172 | oil | C₁₃H₁₄ClF₃N₄OS | F 49.38 C F | 4.51 | 12.71 |
| 173 | oil | C₁₃H₁₁ClF₂N₄O₂ | C 47.50 F 47.80 | 3.37 3.35 | 17.05 16.32 |
| 174 | 86–87 | C₁₃H₁₀ClF₃N₄OS | C 43.04 F 43.71 | 2.78 2.98 | 15.45 15.56 |
| 175 | oil | C₁₆H₁₈ClF₃N₄O₃S | C 43.78 F 44.19 | 4.14 4.07 | 12.77 12.07 |
| 176 | 154–156 | C₁₇H₁₄ClFN₄O₃ | C 54.19 F 55.15 | 3.75 3.75 | 14.87 13.83 |
| 177 | 95–97 | C₁₀H₈ClF₃N₄OS | C F | | |
| 178 | oil | C₁₇H₁₅ClF₂N₄O₂ | C F | | |
| 179 | 122–123 | C₁₀H₈ClFN₄O₄ | C F | | |
| 180 | 68–70 | C₁₈H₁₈ClFN₄O₂ | C F | | |
| 181 | 102–105 | C₁₁H₁₂ClFN₄O₂ | C F | | |
| 182 | oil | C₁₃H₁₃ClFN₄O₄ | C F | | |
| 183 | oil | C₁₈H₂₃ClF₂N₄O₆ | C 46.51 F 48.03 | 4.98 5.09 | 12.05 12.02 |
| 184 | oil | C₁₆H₁₉ClF₂N₄O₄ | C 47.47 F 47.46 | 4.92 4.77 | 13.84 13.65 |
| 185 | oil | C₁₄H₁₄ClFN₄O₂ | C 51.78 F 50.79 | 4.35 4.39 | 17.25 16.55 |
| 186 | 157–158 | C₇H₃ClFN₅O₃ | C F | | |
| 187 | 62–63 | C₁₀H₉ClF₂N₄O | C F | | |
| 188 | oil | C₁₇H₁₈ClF₂N₅O₄ | C 47.50 F 47.57 | 4.22 4.05 | 16.29 15.48 |
| 189 | 80–81 | C₁₀H₈ClF₂N₅O₃ | C F | | |
| 190 | oil | C₁₂H₁₃ClFN₄O₃ | C F | | |
| 191 | oil | C₁₅H₁₉ClF₂N₆O₂ | C 46.33 F 46.59 | 4.93 4.85 | 21.61 21.32 |
| 192 | 132–134 | C₁₅H₁₉ClF₂N₆O₂ | C 46.33 F 46.43 | 4.93 4.85 | 21.61 21.45 |
| 193 | 115–116 | C₁₂H₁₀ClFN₄O₃ | C 46.09 F 46.64 | 3.22 3.10 | 17.92 17.68 |
| 194 | oil | C₁₈H₁₆ClF₂N₅O₃ | C F | | |
| 195 | 92–94 | C₁₂H₁₄ClF₂N₅O₅S₂ | C F | | |
| 196 | 130–131 | C₉H₈ClFN₄O₃ | C F | | |
| 197 | oil | C₁₆H₁₄ClFN₄O₃ | C F | | |
| 198 | 67–68 | C₁₆H₁₄ClFN₄O₂S | C F | | |
| 199 | oil | C₁₉H₂₂ClF₂N₅O₃ | C 51.64 F 49.12 | 5.01 4.55 | 15.84 14.44 |
| 200 | 113–115 | C₁₄H₁₃ClF₂N₆O₂ | C F | | |
| 201 | oil | C₁₄H₁₆ClF₂N₅O₂ | C F | | |
| 202 | 112–113 | C₁₂H₁₂ClF₂N₅O₂ | C F | | |
| 203 | oil | C₁₄H₁₇ClF₂N₄O₃ | C 46.35 F 46.65 | 4.72 4.65 | 15.45 15.30 |
| 204 | oil | C₁₃H₁₅ClF₂N₄O₂ | C 46.92 F 47.10 | 4.54 4.23 | 16.84 16.50 |
| 205 | oil | C₁₄H₁₇ClF₂N₄O₃ | C 46.35 F 46.25 | 4.72 4.36 | 15.44 15.15 |
| 206 | 75–76 | C₁₃H₁₁BrF₂N₄O₂ | C 41.84 F 42.03 | 2.96 2.89 | 15.01 14.70 |
| 207 | 81–84 | C₁₀H₁₀ClF₂N₅O | C F | | |
| 208 | 66–67 | C₁₂H₁₃ClF₂N₄O₂S | C F | | |
| 209 | oil | C₁₃H₁₉BrF₂N₄O₂ | C 45.68 F 45.98 | 4.05 4.20 | 11.84 11.37 |
| 210 | 121–122 | C₁₀H₉BrF₂N₄O₂ | C | | |

TABLE 2-continued

| Compound No. | mp (°C.) | Empirical Formula | Elemental Analysis C | H | N |
|---|---|---|---|---|---|
| 211 | 171–172 | $C_{14}H_{10}BrFN_4O_2$ | C<br>F | | |
| 212 | 84–86 | $C_{17}H_{15}BrF_2N_4O_2$ | C<br>F | | |
| 213 | 75–76 | $C_{15}H_9ClF_4N_4O_2$ | C<br>F | | |
| 214 | 111–112 | $C_{16}H_{11}ClFN_5O_2$ | C<br>F | | |
| 215 | 44–45 | $C_{11}H_{11}ClF_2N_4O$ | C<br>F | | |
| 216 | oil | $C_{12}H_{13}ClF_2N_4O_3S$ | C 39.30<br>F 40.07 | 3.57<br>3.89 | 15.28<br>13.94 |
| 217 | oil | $C_{10}H_8F_3N_5O_3$ | C 39.61 | 2.66 | 23.10 |
| 218 | oil | $C_{14}H_{15}ClF_2N_4O_3$ | F 39.55<br>C 46.60<br>F 46.30 | 3.09<br>4.19<br>3.97 | 21.27<br>15.53<br>14.91 |
| 219 | 69–70 | $C_{13}H_{15}ClF_2N_4O_3$ | C 44.77<br>F 44.78 | 4.34<br>4.24 | 16.07<br>16.08 |
| 220 | oil | $C_{13}H_{11}ClF_2N_5O_4$ | C 46.02<br>F 45.59 | 3.27<br>3.45 | 20.64<br>20.85 |
| 221 | oil | $C_{14}H_{15}ClF_2N_4O_3$ | C 46.61<br>F 46.41 | 4.19<br>4.15 | 15.53<br>15.31 |
| 222 | 100–106 | $C_{14}H_{16}ClF_2N_5O_3$ | C 44.63<br>F 44.51 | 4.28<br>4.38 | 18.59<br>17.70 |
| 223 | 81–82 | $C_{14}H_{17}Cl_2N_5O_4$ | C 44.71<br>F 44.93 | 4.19<br>4.58 | 18.72<br>18.72 |
| 224 | oil | $C_{12}H_{13}BrF_2N_4O_3$ | C 38.01<br>F 37.76 | 3.46<br>3.30 | 14.77<br>14.34 |
| 225 | 78–80 | $C_{14}H_{13}BrF_2N_4O_2$ | C<br>F | | |
| 226 | oil | $C_{10}H_9F_3N_4O$ | C<br>F | | |

TABLE 3

Preemergence Herbicidal Activity

| Compound No. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| Rate (kg/ha) | 4.0 | 4.0 | 4.0 | 4.0 | 4.0 | 4.0 | 4.0 | 4.0 | 4.0 | 4.0 | 0.25 | 4.0 | 4.0 | 4.0 | 4.0 | 4.0 | 4.0 | 4.0 | 4.0 | 4.0 | 4.0 | 4.0 | 4.0 | 4.0 | 4.0 |
| Species | %K | %K | %K | %K | %K | %K | %K | %K | %K | %K | %K | %K | %K | %K | %K | %K | %K | %K | %K | %K | %K | %K | %K | %K | %K |
| Cotton | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 20 |
| Soybean | 0 | 0 | — | 0 | 0 | 0 | 0 | 0 | 60 | 50 | 0 | 0 | — | 0 | 0 | 0 | 0 | 0 | 80 | — | 0 | 0 | 0 | 60 | 10 |
| Field Corn | — | — | — | — | 0 | — | 10 | 100 | — | — | 30 | — | — | — | — | — | — | 60 | 100 | 30 | 20 | 95 | 0 | 95 | 0 |
| Rice | 0 | 75 | 0 | 0 | 80 | 0 | 20 | 100 | 100 | 90 | 20 | — | 30 | 20 | 100 | — | 0 | 0 | 60 | 0 | 30 | 85 | 90 | 80 | 10 |
| Wheat | 0 | 0 | — | 0 | 0 | — | — | 0 | — | 0 | 0 | 0 | — | — | 0 | — | — | 0 | 100 | 0 | 0 | 0 | 0 | 0 | 0 |
| Field Bindweed | — | 100 | 0 | 0 | 80 | 0 | 0 | 100 | 0 | 100 | 0 | 0 | 100 | 0 | 100 | 0 | 100 | 100 | 40 | 100 | 0 | 20 | 0 | 0 | 90 |
| Morningglory | 100 | 100 | 100 | 80 | 100 | 90 | 100 | 100 | 100 | 100 | 80 | 100 | 100 | 100 | 80 | 100 | 100 | 100 | 100 | 100 | 100 | 100 | 75 | 100 | 90 |
| Velvetleaf | 0 | 0 | 0 | 25 | 0 | 0 | 70 | 100 | 100 | 100 | 80 | 100 | 95 | 40 | 100 | 100 | 90 | 100 | 100 | 20 | 50 | 0 | 95 | 100 | 90 |
| Barnyardgrass | 90 | 95 | 90 | 85 | 60 | 100 | 100 | 100 | 100 | 100 | 95 | 100 | 100 | 100 | 100 | 100 | 100 | 100 | 100 | 95 | 100 | 100 | 95 | 100 | 90 |
| Green Foxtail | 0 | 0 | 0 | 90 | 40 | 0 | 90 | 100 | 95 | 100 | 50 | 95 | 100 | 95 | 90 | 95 | 90 | 40 | 90 | — | 85 | 10 | 40 | 100 | 20 |
| Johnsongrass | — | — | — | — | — | — | 0 | 20 | 30 | — | 0 | — | 100 | — | 0 | — | 60 | 0 | 50 | 0 | 0 | 0 | 0 | 0 | — |
| Yellow Nutsedge | | | | | | | | | | | | | | | | | | | | | | | | | |
| Compound No. | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 |
| Rate (kg/ha) | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 0.25 | 0.25 | 4.0 | 0.25 | 0.25 | 4.0 | 0.25 | 0.25 | 0.25 |
| Species | %K | %K | %K | %K | %K | %K | %K | %K | %K | %K | %K | %K | %K | %K | %K | %K | %K | %K | %K | %K | %K | %K | %K | %K | %K |
| Cotton | 0 | 0 | 0 | 0 | 50 | 0 | 0 | 0 | 0 | 30 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 20 | 0 | 0 | 0 | 30 | 20 | 0 | 0 | — | 0 | 0 | 0 | 30 | 30 | 0 | 50 | 30 | 30 | 0 | 0 |
| Field Corn | — | — | — | — | — | 0 | 60 | — | 40 | 0 | — | 0 | — | 20 | 0 | 60 | 0 | 30 | 30 | — | 40 | 100 | 90 | 100 | 0 |
| Rice | 20 | 40 | 0 | 0 | 0 | 10 | 90 | 20 | 0 | 100 | 40 | 0 | 0 | 0 | 70 | 90 | 0 | 30 | 100 | 0 | 0 | 100 | 80 | 100 | 0 |
| Wheat | 70 | 20 | 0 | 0 | 0 | 100 | 0 | 0 | 50 | 95 | 0 | 0 | 100 | 0 | 20 | 100 | 0 | 30 | 30 | 0 | 40 | 0 | 0 | 0 | 0 |
| Field Bindweed | — | 0 | 0 | 0 | — | 0 | 0 | 100 | 0 | 20 | 0 | 0 | 50 | 0 | 90 | 0 | 0 | 100 | 100 | 100 | 100 | 100 | 100 | 100 | 95 |
| Morningglory | 100 | 100 | 80 | 80 | 70 | 100 | 80 | 100 | 100 | 100 | 100 | 100 | 50 | 100 | 90 | 100 | 100 | 80 | 100 | 100 | 100 | 100 | 100 | 100 | 90 |
| Velvetleaf | 90 | 100 | 0 | 100 | 90 | 100 | 90 | 60 | 80 | 20 | 80 | 40 | 100 | 40 | 90 | 100 | 0 | 95 | 100 | 20 | 50 | 100 | 100 | 60 | 100 |
| Barnyardgrass | 100 | 100 | 100 | 100 | 100 | 100 | 100 | 100 | 100 | 95 | 95 | 100 | 100 | 100 | 100 | 100 | 100 | 90 | 100 | 95 | 100 | 100 | 100 | 100 | 100 |
| Green Foxtail | 70 | 100 | 0 | 95 | 50 | 0 | 90 | — | 95 | 30 | 100 | 20 | 100 | 95 | 60 | 100 | 90 | 30 | 95 | 50 | 20 | 10 | 0 | 30 | 10 |
| Johnsongrass | — | 0 | — | — | — | 0 | 30 | 20 | 30 | 100 | 30 | — | 100 | — | 0 | 75 | 0 | 0 | 10 | — | 20 | 90 | 0 | — | — |
| Compound No. | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 |
| Rate (kg/ha) | 0.25 | 4.0 | 4.0 | 2.0 | 4.0 | 0.25 | 4.0 | 4.0 | 4.0 | 4.0 | 4.0 | 4.0 | 4.0 | 4.0 | 4.0 | 4.0 | 4.0 | 0.25 | 0.25 | 4.0 | 4.0 | 4.0 | 4.0 | 4.0 | 4.0 |
| Species | %K | %K | %K | %K | %K | %K | %K | %K | %K | %K | %K | %K | %K | %K | %K | %K | %K | %K | %K | %K | %K | %K | %K | %K | %K |
| Cotton | 0 | 0 | 0 | 0 | 0 | 0 | 0 | 0 | 20 | 0 | 0 | 0 | 0 | 0 | 0 | 0 | 0 | 0 | 0 | 0 | 0 | 0 | 0 | 0 | 0 |
| Soybean | 0 | 20 | 0 | 0 | 70 | 0 | 0 | 0 | 30 | 20 | 0 | 0 | 0 | 80 | 70 | 75 | 60 | 0 | 30 | 90 | 0 | 0 | 0 | 0 | — |
| Field Corn | 0 | 30 | 60 | 100 | 30 | 0 | 0 | 0 | 30 | 0 | 90 | 0 | — | 100 | 20 | 90 | — | 0 | 30 | — | 50 | 30 | 30 | — | 0 |
| Rice | 0 | 0 | 10 | 50 | 10 | 10 | 0 | 30 | 90 | 100 | 90 | 0 | 0 | 20 | 90 | 100 | 100 | 0 | 60 | 90 | 40 | 100 | 90 | 80 | — |
| Wheat | 0 | 100 | 0 | 90 | 0 | 100 | 0 | 0 | 80 | 95 | 20 | 0 | 0 | 60 | 100 | 100 | 20 | 0 | 80 | 100 | 40 | 100 | 80 | 100 | 0 |
| Field Bindweed | 0 | 70 | 0 | 85 | 60 | 0 | 0 | 20 | 100 | 20 | 0 | 0 | 0 | 0 | 0 | 0 | 0 | 0 | 0 | 0 | 0 | 0 | 0 | 0 | 100 |
| Morningglory | 0 | 20 | 20 | 10 | 50 | 100 | 100 | 100 | 100 | 100 | 50 | 0 | 30 | 20 | 20 | 0 | 100 | 0 | 0 | 100 | 20 | 80 | 100 | 30 | 80 |
| Velvetleaf | 100 | 100 | 100 | 100 | 100 | 100 | 100 | 60 | 100 | 50 | 100 | 100 | 20 | 60 | 90 | 100 | 95 | 90 | 100 | 100 | 95 | 100 | 40 | 100 | 0 |
| Barnyardgrass | 90 | 100 | 80 | 100 | 95 | 100 | 100 | 100 | 100 | 95 | 100 | 10 | 30 | 100 | 90 | 100 | 100 | 90 | 100 | 100 | 100 | 95 | 100 | 100 | 40 |
| Green Foxtail | 50 | 100 | 100 | 100 | 100 | 100 | 70 | 100 | 100 | 95 | 100 | 95 | 50 | 100 | 100 | 100 | 80 | 90 | 90 | 100 | 90 | 100 | 100 | 10 | 90 |
| Johnsongrass | 100 | 30 | 100 | 10 | 0 | 0 | 20 | — | 40 | 80 | 30 | 80 | — | 95 | 60 | 75 | 40 | 30 | 0 | 0 | 0 | 0 | 0 | — | — |
| Yellow Nutsedge | | | | | | | | | | | | | | | | | | | | | | | | | |
| Compound No. | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 |
| Rate (kg/ha) | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 2.0 | 2.0 | 4.0 |
| Species | %K | %K | %K | %K | %K | %K | %K | %K | %K | %K | %K | %K | %K | %K | %K | %K | %K | %K | %K | %K | %K | %K | %K | %K | %K |

TABLE 3-continued

Preemergence Herbicidal Activity

| Compound No. | 101 | 102 | 103 | 104 | 105 | 106 | 107 | 108 | 109 | 110 | 111 | 112 | 113 | 114 | 115 | 116 | 117 | 118 | 119 | 120 | 121 | 122 | 123 | 124 | 125 |
|---|---|---|---|---|---|---|---|---|---|---|---|---|---|---|---|---|---|---|---|---|---|---|---|---|---|
| Rate (kg/ha) | 8.0 | 4.0 | 4.0 | 4.0 | 4.0 | 4.0 | 2.0 | 4.0 | 8.0 | 8.0 | 8.0 | 8.0 | 8.0 | 8.0 | 4.0 | 2.0 | 4.0 | 8.0 | 8.0 | 8.0 | 2.0 | 8.0 | 8.0 | 4.0 | 1.0 |
| Species | %K | %K | %K | %K | %K | %K | %K | %K | %K | %K | %K | %K | %K | %K | %K | %K | %K | %K | %K | %K | %C | %C | %C | %C | %C |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 60 | 20 | 20 | 0 |
| Field Corn | 0 | — | — | 0 | 0 | — | 0 | 50 | — | — | — | — | — | — | — | — | — | — | — | 20 | 0 | 0 | 0 | 35 | 0 |
| Rice | 0 | 0 | 95 | 0 | 75 | 0 | 0 | 20 | 0 | 25 | 0 | 0 | 0 | 0 | 0 | 0 | 0 | 0 | 80 | 0 | 0 | 50 | 10 | 75 | 0 |
| Wheat | 0 | 30 | 100 | 0 | 0 | 0 | 0 | 0 | 0 | 10 | 0 | 30 | 0 | 0 | 0 | 0 | 20 | 20 | 40 | 0 | 0 | 30 | 10 | 10 | 0 |
| Field Bindweed | 0 | — | — | 0 | 0 | — | 0 | 80 | — | — | — | — | — | — | — | — | — | — | — | 0 | 0 | 60 | 10 | 90 | 0 |
| Morningglory | 0 | 20 | — | 0 | 0 | 0 | 0 | 60 | 20 | 100 | 70 | 70 | 40 | 0 | 0 | 0 | 0 | 0 | 0 | 0 | 100 | 100 | 10 | 0 | 60 |
| Velvetleaf | 0 | 100 | 100 | 0 | 100 | 100 | 40 | 100 | 0 | 100 | 100 | 100 | 100 | 100 | 100 | 30 | 100 | 100 | 100 | 100 | 0 | 100 | 95 | 80 | 0 |
| Barnyardgrass | 0 | 0 | 95 | 90 | 25 | 0 | 0 | 0 | 100 | 65 | 100 | 100 | 100 | 90 | 100 | 90 | 100 | 50 | 50 | 50 | 100 | 100 | 100 | 70 | 50 |
| Green Foxtail | 0 | 95 | 100 | 0 | 100 | 80 | 0 | 70 | 100 | 95 | 100 | 100 | 100 | 0 | 100 | 100 | 100 | 30 | 100 | 100 | 0 | 100 | 100 | 100 | 60 |
| Johnsongrass | 0 | 0 | 50 | 0 | 100 | 0 | 0 | 0 | 95 | 100 | 100 | 100 | 95 | 0 | 100 | 80 | 100 | 0 | 60 | 90 | 0 | 100 | 60 | 50 | — |
| Yellow Nutsedge | 0 | — | — | 0 | — | — | 0 | 0 | — | — | — | — | — | — | — | — | — | — | — | — | — | — | — | 0 | — |

| Compound No. | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 | 149 | 150 |
|---|---|---|---|---|---|---|---|---|---|---|---|---|---|---|---|---|---|---|---|---|---|---|---|---|---|
| Rate (kg/ha) | 4.0 | 2.0 | 2.0 | 2.0 | 4.0 | 8.0 | 2.0 | 2.0 | 2.0 | 2.0 | 2.0 | 2.0 | 8.0 | 2.0 | 2.0 | 0.125 | 2.0 | 8.0 | 4.0 | 8.0 | 8.0 | 8.0 | 8.0 | 8.0 | 8.0 |
| Species | %C | %C | %C | %C | %C | %C | %C | %C | %C | %C | %C | %C | %C | %C | %C | %C | %C | %C | %C | %C | %C | %C | %C | %C | %C |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Field Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 30 | 0 | — | 0 | 0 | — | 0 | 0 | — | — |
| Wheat | 0 | 0 | 0 | 0 | 0 | 0 | 0 | 0 | 0 | 0 | 0 | 0 | 0 | 0 | 0 | 30 | 0 | 0 | 0 | 0 | 0 | 0 | 0 | 0 | 0 |
| Field Bindweed | 0 | 0 | 0 | 0 | 0 | 0 | 0 | 0 | 0 | 0 | 0 | 0 | 0 | 0 | 0 | 80 | 0 | — | — | — | — | — | — | — | — |
| Morningglory | 0 | 0 | 30 | 0 | 0 | 0 | 0 | 0 | 0 | 100 | 100 | 50 | 100 | 90 | 100 | 100 | 100 | 100 | 100 | 100 | 100 | 100 | 100 | 100 | 100 |
| Velvetleaf | 50 | 0 | 0 | 90 | 95 | 0 | 30 | 0 | 100 | 100 | 20 | 80 | 40 | 0 | 100 | 40 | 100 | 100 | 100 | 100 | — | 100 | 100 | 100 | 100 |
| Barnyardgrass | 0 | 75 | 0 | 0 | 0 | 100 | 0 | 0 | 100 | 100 | 100 | 100 | 10 | 0 | 100 | 50 | 100 | 100 | 100 | 100 | 100 | 100 | 100 | 100 | 100 |
| Green Foxtail | 0 | 0 | 0 | 0 | 0 | 0 | 0 | 100 | 100 | 20 | 100 | 100 | 0 | 0 | 100 | 100 | 100 | 100 | 80 | 100 | 100 | 40 | 100 | 100 | 100 |
| Johnsongrass | 0 | 0 | 0 | 0 | 0 | 80 | 0 | 0 | 30 | 40 | 95 | 90 | 10 | 0 | 100 | 60 | 100 | 100 | 30 | 100 | 100 | 30 | 100 | 70 | 100 |
| Yellow Nutsedge | 0 | 0 | 0 | 0 | 0 | — | 0 | 0 | 50 | — | — | 0 | — | — | 100 | 50 | 20 | 100 | 30 | — | 100 | 30 | — | 20 | 80 |

| Compound No. | 151 | 152 | 153 | 154 | 157 | 158 | 159 | 160 | 161 | 162 | 163 | 164 | 165 | 166 | 167 | 168 | 169 | 170 | 171 | 172 | 173 | 174 | 175 | 176 |
|---|---|---|---|---|---|---|---|---|---|---|---|---|---|---|---|---|---|---|---|---|---|---|---|---|
| Rate (kg/ha) | 8.0 | 1.0 | 1.0 | 2.0 | 8.0 | 8.0 | 8.0 | 1.0 | 8.0 | 8.0 | 0.5 | 0.5 | 1.0 | 8.0 | 8.0 | 1.0 | 0.125 | 1.0 | 1.0 | 0.5 | 0.125 | 0.5 | 1.0 | 8.0 |
| Species | %C | %C | %C | %C | %C | %C | %C | %C | %C | %C | %C | %C | %C | %C | %C | %C | %C | %C | %C | %C | %C | %C | %C | %C |
| Cotton | 0 | 0 | 20 | 100 | 20 | 100 | 90 | 90 | 100 | 20 | 30 | 80 | 80 | 100 | 100 | 20 | 40 | 10 | 100 | 20 | 10 | 20 | 40 | 20 |
| Soybean | 0 | 10 | 10 | 20 | 0 | 80 | 100 | 70 | 100 | 10 | 50 | 10 | 10 | 90 | 50 | 50 | 40 | 60 | 60 | 20 | 40 | 90 | 10 | 50 |
| Field Corn | 0 | 10 | 0 | 30 | — | 90 | 80 | 90 | 100 | 80 | 90 | 0 | 80 | 70 | 80 | 80 | 90 | 70 | 10 | 40 | 70 | 60 | 0 | 0 |
| Rice | — | 90 | — | 90 | — | — | — | 90 | — | — | — | 100 | 80 | — | 70 | 70 | 80 | 30 | 100 | 60 | 80 | 70 | 70 | — |

TABLE 3-continued

Preemergence Herbicidal Activity

| | | | | | | | | | | | | | | | | | | | | | | | | |
|---|---|---|---|---|---|---|---|---|---|---|---|---|---|---|---|---|---|---|---|---|---|---|---|---|
| Wheat | 0 | 70 | 0 | 90 | 0 | 90 | 100 | 90 | 100 | 80 | 100 | 40 | 100 | 0 | 100 | 20 | 40 | 40 | 90 | | | | | |
| Field Bindweed | 0 | 100 | 90 | 100 | 10 | 100 | 100 | 100 | 100 | 100 | 100 | 10 | 100 | 0 | 100 | 30 | 30 | 100 | 100 | | | | | |
| Morningglory | 0 | 90 | 20 | 100 | 60 | 100 | 100 | 100 | 100 | 80 | 100 | 30 | 100 | 10 | 90 | 10 | 0 | 100 | 60 | | | | | |
| Velvetleaf | 0 | 100 | 90 | 100 | 60 | 100 | 100 | 100 | 100 | 60 | 100 | 100 | 100 | 90 | 100 | 100 | 100 | 100 | 100 | | | | | |
| Barnyardgrass | 0 | 100 | 90 | 100 | 50 | 100 | 100 | 100 | 100 | 60 | 100 | 70 | 100 | 90 | 100 | 90 | 100 | 100 | 80 | | | | | |
| Green Foxtail | 0 | 100 | 100 | 100 | 80 | 100 | 100 | 100 | 100 | 60 | 100 | 100 | 100 | 100 | 100 | 100 | 100 | 100 | 100 | | | | | |
| Johnsongrass | 0 | 90 | 20 | 100 | 50 | 100 | 100 | 100 | 100 | 60 | 100 | 70 | 100 | 90 | 90 | 80 | 90 | 90 | 100 | | | | | |
| Yellow Nutsedge | — | 90 | 0 | 90 | 20 | — | 100 | — | — | 80 | — | 40 | — | 10 | 90 | 40 | 30 | 30 | 70 | | | | | |
| Compound No. | 177 | 178 | 179 | 180 | 181 | 182 | 183 | 184 | 185 | 186 | 187 | 188 | 189 | 190 | 191 | 192 | 193 | 194 | 195 | 196 | 197 | 198 | 199 | 200 |
| Rate (kg/ha) | 8.0 | 8.0 | 4.0 | 8.0 | 8.0 | 2.0 | 1.0 | 1.0 | 1.0 | 8.0 | 0.5 | 1.0 | 1.0 | 0.25 | 1.0 | 1.0 | 1.0 | 1.0 | 1.0 | 8.0 | 8.0 | 8.0 | 0.5 | 2.0 |
| Species | %C | %C | %C | %C | %C | %C | %C | %C | %C | %C | %C | %C | %C | %C | %C | %C | %C | %C | %C | %C | %C | %C | %C | %C |
| Cotton | 70 | 20 | 60 | 0 | 20 | 100 | 100 | 100 | 20 | 0 | 0 | 100 | 10 | 80 | 40 | 10 | 90 | 0 | 100 | 50 | 10 | 10 | 0 | 30 |
| Soybean | 90 | 50 | 20 | 0 | 40 | 20 | 20 | 20 | 20 | 0 | 30 | 0 | 0 | 70 | 30 | 0 | 100 | 60 | 50 | 40 | 0 | 0 | 10 | 50 |
| Field Corn | 90 | 90 | 10 | 0 | 60 | 70 | 20 | 40 | 80 | — | 90 | 10 | 0 | 100 | 100 | 10 | 100 | 10 | 100 | 40 | 70 | 50 | 60 | 70 |
| Rice | — | — | 80 | — | 0 | 100 | 80 | 100 | 80 | — | 70 | 90 | 10 | — | 60 | 0 | 100 | 0 | — | — | — | — | — | 20 |
| Wheat | 70 | 70 | 50 | 0 | 30 | 90 | 80 | 90 | 70 | 0 | 70 | 70 | 0 | 100 | 90 | 10 | 100 | 10 | 90 | 80 | 70 | 70 | 40 | 20 |
| Field Bindweed | 40 | 20 | 100 | 0 | 40 | 100 | 100 | 100 | 30 | 0 | 70 | 70 | 10 | 50 | 50 | 10 | 90 | 60 | 100 | 60 | 90 | 60 | 50 | 20 |
| Morningglory | 70 | 80 | 90 | 20 | 10 | 90 | 90 | 100 | 60 | 0 | 30 | 100 | 10 | 100 | 90 | 0 | 90 | 80 | 100 | 40 | 60 | 80 | 10 | 20 |
| Velvetleaf | 100 | 100 | 100 | 10 | 30 | 100 | 100 | 100 | 100 | 0 | 50 | 100 | 70 | 100 | 100 | 80 | 100 | 60 | 100 | 100 | 100 | 100 | 90 | 10 |
| Barnyardgrass | 90 | 90 | 100 | 80 | 80 | 100 | 100 | 100 | 100 | 0 | 100 | 100 | 40 | 100 | 60 | 0 | 100 | 70 | 100 | 100 | 100 | 100 | 30 | 10 |
| Green Foxtail | 90 | 100 | 100 | 90 | 90 | 100 | 100 | 100 | 100 | 0 | 90 | 90 | 30 | 100 | 90 | 50 | 100 | 0 | 80 | 70 | 90 | 100 | 70 | 50 |
| Johnsongrass | 70 | 50 | 90 | 80 | 40 | 100 | 90 | 90 | 90 | 0 | 90 | 90 | 10 | 100 | 60 | 0 | 90 | 0 | 90 | 70 | 90 | 90 | 60 | 10 |
| Yellow Nutsedge | — | — | 60 | — | — | 100 | 90 | 70 | 20 | — | 40 | — | — | 90 | — | — | — | — | — | — | — | — | 20 | — |
| Compound No. | 201 | 202 | 203 | 204 | 205 | 206 | 207 | 208 | 209 | 210 | 211 | 212 | 213 | 214 | 215 | 216 | 217 | 218 | 219 | 220 | 221 | 222 | 223 | 224 | 225 |
| Rate (kg/ha) | 2.0 | 2.0 | 0.5 | 0.5 | 0.5 | 0.25 | 4.0 | 0.5 | 1.0 | 8.0 | 4.0 | 8.0 | 8.0 | 8.0 | 8.0 | 2.0 | 8.0 | 0.5 | 0.5 | 2.0 | 1.0 | 1.0 | 1.0 | 0.5 | 0.5 |
| Species | %C | %C | %C | %C | %C | %C | %C | %C | %C | %C | %C | %C | %C | %C | %C | %C | %C | %C | %C | %C | %C | %C | %C | %C | %C |
| Cotton | 90 | 20 | 80 | 40 | 60 | 90 | 50 | 50 | 50 | 0 | 0 | 0 | 0 | 0 | 100 | 100 | 30 | 90 | 80 | 70 | 90 | 60 | 10 | 80 | 90 |
| Soybean | 90 | 60 | 70 | 70 | 40 | 90 | 90 | 40 | 20 | 0 | 0 | 0 | 0 | 0 | 100 | 90 | 20 | 80 | 60 | 40 | 80 | 80 | 0 | 70 | 100 |
| Field Corn | 100 | 0 | 90 | 80 | 90 | 90 | 20 | 50 | 40 | 100 | 0 | 0 | 0 | 0 | 80 | 100 | 40 | 100 | 100 | 80 | 100 | 100 | 20 | 100 | 100 |
| Rice | 90 | 20 | 90 | 90 | 90 | 70 | 20 | 40 | 90 | 0 | 0 | 0 | — | — | 100 | 100 | — | 100 | 80 | 50 | 95 | 50 | 10 | 95 | 90 |
| Wheat | 100 | 10 | 90 | 70 | 90 | 60 | 30 | 40 | 50 | 0 | 0 | 0 | 0 | 0 | 100 | 100 | 40 | 100 | 90 | 70 | 95 | 80 | 0 | 100 | 95 |
| Field Bindweed | 60 | 10 | 100 | 100 | 100 | 100 | 30 | 100 | 100 | 0 | 0 | 100 | 100 | 0 | 100 | 100 | 0 | 100 | 100 | 20 | 100 | 100 | 20 | 100 | 100 |
| Morningglory | 20 | 10 | 100 | 90 | 100 | 100 | 30 | 50 | 100 | 0 | 0 | 100 | 100 | 0 | 100 | 100 | 0 | 100 | 100 | 50 | 95 | 80 | 0 | 100 | 100 |
| Velvetleaf | 100 | 90 | 100 | 100 | 100 | 100 | 100 | 100 | 100 | 0 | 0 | 100 | 100 | 40 | 100 | 100 | 90 | 100 | 100 | 100 | 100 | 100 | 40 | 100 | 100 |
| Barnyardgrass | 100 | 0 | 100 | 100 | 100 | 100 | 40 | 100 | 100 | 0 | 0 | 100 | 100 | 0 | 100 | 100 | 40 | 100 | 100 | 90 | 100 | 95 | 10 | 100 | 100 |
| Green Foxtail | 100 | 0 | 100 | 100 | 100 | 100 | 10 | 90 | 90 | 0 | 0 | 90 | 90 | 60 | 100 | 90 | 0 | 100 | 100 | 90 | 95 | 95 | 0 | 100 | 95 |
| Johnsongrass | 70 | 0 | 90 | 90 | 100 | 100 | 40 | 90 | 80 | 0 | 0 | 0 | 0 | — | 100 | 90 | 70 | 90 | 90 | 90 | 70 | 70 | 0 | 100 | 95 |
| Yellow Nutsedge | 50 | 0 | 70 | 40 | 60 | 60 | 20 | 40 | 70 | — | 0 | 0 | — | — | 100 | — | — | 90 | 90 | 40 | 70 | 40 | 0 | 95 | 70 |

TABLE 5

Postemergence Herbicidal Activity

| Compound No. | 4 | 5 | 8 | 9 | 11 | 12 | 14 | 15 | 18 | 19 | 20 | 21 | 24 | 27 | 28 | 31 | 32 | 34 |
|---|---|---|---|---|---|---|---|---|---|---|---|---|---|---|---|---|---|---|
| Rate (kg/ha) | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 |
| Species | % K | % K | % K | % K | % K | % K | % K | % K | % K | % K | % K | % K | % K | % K | % K | % K | % K | % K |
| Cotton | 90 | 30 | 50 | 50 | 100 | 30 | 60 | 20 | 60 | 100 | 0 | 80 | 100 | 0 | 50 | 90 | 70 | 60 |
| Soybean | 0 | 0 | 0 | 0 | 100 | 0 | 0 | 0 | 0 | 0 | 0 | 0 | 0 | 0 | 0 | 10 | 0 | 0 |
| Field Corn | 0 | 0 | 0 | 0 | 100 | 0 | 0 | 0 | 0 | 0 | 0 | 0 | 0 | 0 | 0 | 0 | 0 | 0 |
| Rice | 0 | 0 | 0 | 0 | 100 | 0 | 0 | 0 | 0 | 20 | 0 | 0 | 0 | 0 | 0 | 30 | 0 | 0 |
| Wheat | 0 | 0 | 0 | 0 | 100 | 0 | 0 | 0 | 0 | 0 | 0 | 0 | 0 | 0 | 0 | 0 | 0 | 0 |
| Field Bindweed | 0 | 0 | 0 | 80 | 100 | 0 | 0 | 0 | 20 | 70 | 40 | 0 | 0 | 0 | 0 | 20 | 0 | 95 |
| Morningglory | 0 | 0 | 0 | 0 | 100 | 0 | 0 | 0 | 0 | 30 | 0 | 0 | 0 | 0 | 0 | 80 | 0 | 20 |
| Velvetleaf | 100 | 100 | 100 | 100 | 100 | 100 | 100 | 100 | 100 | 100 | 100 | 100 | 100 | 90 | 95 | 0 | 100 | 100 | 100 |
| Barnyardgrass | 0 | 0 | 0 | 0 | 100 | 0 | 0 | 0 | 0 | 10 | 0 | 0 | 0 | 0 | 0 | 90 | 0 | 0 |
| Green Foxtail | 20 | 80 | 0 | 40 | 100 | 80 | 0 | 0 | 0 | 100 | 80 | 60 | 0 | 0 | 0 | 95 | 95 | 95 |
| Johnsongrass | 0 | 0 | 0 | 0 | 100 | 0 | 0 | 0 | 70 | 90 | 0 | 0 | 0 | 0 | 0 | 100 | 50 | 50 |
| Yellow Nutsedge | 0 | 0 | 0 | 0 | 60 | 0 | 0 | 0 | 0 | 0 | 0 | 0 | 0 | 0 | 0 | 0 | 0 | 0 |

| Compound No. | 35 | 36 | 37 | 38 | 40 | 41 | 42 | 43 | 44 | 45 | 47 | 48 | 49 | 51 | 52 | 53 | 54 | 55 |
|---|---|---|---|---|---|---|---|---|---|---|---|---|---|---|---|---|---|---|
| Rate (kg/ha) | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 |
| Species | % K | % K | % K | % K | % K | % K | % K | % K | % K | % K | % K | % K | % K | % K | % K | % K | % K | % K |
| Cotton | 100 | 100 | 20 | 100 | 70 | 0 | 65 | 100 | 100 | 80 | 100 | 100 | 100 | 100 | 100 | 100 | 50 | 40 |
| Soybean | 0 | 0 | 0 | 0 | 0 | 0 | 0 | 30 | 10 | 0 | 10 | 100 | 0 | 50 | 0 | 10 | 0 | 0 |
| Field Corn | 0 | 0 | 0 | 0 | 0 | 0 | 0 | 40 | 0 | 0 | 0 | 100 | 0 | 30 | 0 | 0 | 0 | 0 |
| Rice | 30 | 0 | 0 | 0 | 0 | 0 | 40 | 95 | 0 | 50 | 30 | 100 | 0 | 30 | 0 | 0 | 0 | 0 |
| Wheat | 0 | 0 | 0 | 0 | 0 | 0 | 0 | — | 0 | 40 | — | 100 | 0 | — | 80 | 0 | 0 | 0 |
| Field Bindweed | 95 | 50 | 0 | 50 | 90 | 0 | 65 | 100 | 80 | 90 | 0 | 100 | 0 | 100 | 60 | 90 | 85 | 100 |
| Morningglory | 50 | 0 | 0 | 20 | 30 | 0 | 90 | 100 | 90 | 80 | 100 | 100 | 60 | 90 | 20 | 100 | 30 | 80 |
| Velvetleaf | 100 | 100 | 100 | 100 | 100 | 60 | 100 | 100 | 100 | 100 | 100 | 100 | 100 | 100 | 100 | 100 | 100 | 100 |
| Barnyardgrass | 40 | 85 | 20 | 0 | 0 | 0 | 100 | 100 | 100 | 70 | 80 | 100 | 20 | 95 | 0 | 70 | 10 | 50 |
| Green Foxtail | 90 | 40 | 70 | 90 | 100 | 0 | 90 | 90 | 100 | 100 | 100 | 100 | 0 | 100 | 90 | 100 | 70 | 90 |
| Johnsongrass | 60 | 65 | 0 | 0 | 10 | 0 | 100 | 100 | 80 | 100 | 100 | 100 | 80 | 100 | 10 | 100 | 100 | 95 |
| Yellow Nutsedge | 40 | 0 | 0 | 0 | 0 | 0 | 0 | — | 0 | 0 | 0 | 90 | 0 | 0 | 0 | 0 | 0 | 0 |

| Compound No. | 56 | 57 | 58 | 59 | 60 | 61 | 65 | 66 | 68 | 69 | 70 | 71 | 72 | 73 | 74 | 76 | 78 | 79 |
|---|---|---|---|---|---|---|---|---|---|---|---|---|---|---|---|---|---|---|
| Rate (kg/ha) | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 | 4.0 |
| Species | % K | % K | % K | % K | % K | % K | % K | % K | % K | % K | % K | % K | % K | % K | % K | % K | % K | % K |
| Cotton | 100 | 100 | 90 | 100 | 100 | 100 | 100 | 10 | 100 | 100 | 90 | 60 | 10 | 0 | 10 | 50 | 60 | 90 |
| Soybean | 80 | 0 | 0 | 0 | 0 | 0 | 0 | 0 | 0 | 100 | 0 | 10 | 0 | 0 | 0 | 0 | 0 | 0 |
| Field Corn | 100 | 0 | 0 | 0 | 0 | 0 | 0 | 0 | 0 | 100 | 0 | 0 | 0 | 0 | 0 | 0 | 0 | 0 |
| Rice | 40 | 0 | 0 | 0 | 0 | 0 | 0 | 10 | 0 | 100 | 0 | 0 | 0 | 0 | 0 | 0 | 0 | 0 |
| Wheat | 100 | 0 | 0 | 0 | 0 | 0 | 0 | 0 | 0 | 100 | 0 | 0 | 0 | 0 | 0 | 0 | 0 | 0 |
| Field Bindweed | 100 | 100 | 0 | 0 | 0 | 100 | 20 | 30 | 50 | 100 | 30 | 30 | 100 | 0 | 0 | 40 | 0 | 50 |
| Morningglory | 100 | 100 | 0 | 0 | 10 | 0 | 50 | 50 | 40 | 100 | 30 | 80 | 10 | 0 | 10 | 50 | 0 | 0 |
| Velvetleaf | 100 | 100 | 100 | 100 | 90 | 100 | 100 | 100 | 100 | 100 | 100 | 100 | 60 | 0 | 100 | 100 | 0 | 100 |
| Barnyardgrass | 100 | 0 | 0 | 0 | 0 | 100 | 80 | 70 | 0 | 100 | 90 | 30 | 0 | 0 | 0 | 0 | 0 | 0 |
| Green Foxtail | 100 | 30 | 90 | 95 | 0 | 100 | 20 | 65 | 100 | 100 | 20 | 30 | 0 | 0 | 0 | 0 | 0 | 0 |
| Johnsongrass | 100 | 0 | 0 | 50 | 70 | 100 | 80 | 10 | 0 | 100 | 30 | 0 | 0 | 0 | 0 | 0 | 0 | 0 |
| Yellow Nutsedge | 40 | 0 | 0 | 0 | 0 | 50 | 0 | 0 | 0 | 100 | 0 | 0 | 0 | 0 | 0 | 0 | 0 | 0 |

| Compound No. | 80 | 84 | 87 | 88 | 94 | 95 | 96 | 97 | 115 | 116 | 117 | 118 | 119 | 120 | 121 | 122 | 123 | 124 |
|---|---|---|---|---|---|---|---|---|---|---|---|---|---|---|---|---|---|---|
| Rate (kg/ha) | 4.0 | 4.0 | 4.0 | 4.0 | 4.0 | 4.0 | 4.0 | 4.0 | 4.0 | 2.0 | 4.0 | 8.0 | 8.0 | 8.0 | 2.0 | 8.0 | 8.0 | 4.0 |
| Species | % K | % K | % K | % K | % K | % K | % K | % K | % K | % K | % K | % K | % K | % K | % C | % C | % C | % C |
| Cotton | 95 | 60 | 30 | 60 | 0 | 85 | 85 | 10 | 100 | 100 | 80 | 100 | 0 | 100 | 100 | 30 | 20 | 100 |
| Soybean | 0 | 0 | 0 | 0 | 0 | 0 | 0 | 0 | 40 | 100 | 40 | 100 | 0 | 10 | 100 | 10 | 20 | 30 |
| Field Corn | 0 | 0 | 0 | 0 | 0 | 0 | 0 | 0 | 100 | 100 | 100 | 100 | 0 | 30 | 100 | 0 | 30 | 40 |
| Rice | 0 | 0 | 0 | 0 | 0 | 0 | 10 | 0 | 0 | 100 | 100 | 30 | — | — | — | 100 | 0 | — | 90 |
| Wheat | 0 | 0 | 0 | 0 | 0 | 0 | 0 | 0 | 100 | 100 | 60 | 100 | 0 | 10 | 100 | 0 | 10 | 20 |
| Field Bindweed | 10 | 70 | 0 | 30 | 90 | 35 | 50 | 0 | 100 | 100 | 60 | 100 | 0 | 90 | 100 | 70 | 10 | 100 |
| Morningglory | 10 | 0 | 20 | 0 | 0 | 20 | 0 | 0 | 100 | 100 | 70 | 100 | 0 | 90 | 100 | 0 | 20 | 100 |
| Velvetleaf | 100 | 20 | 100 | 100 | 90 | 100 | 100 | 100 | 100 | 100 | 100 | 100 | 0 | 100 | — | 50 | 20 | 100 |
| Barnyardgrass | 20 | 0 | 25 | 50 | 0 | 0 | 0 | 90 | 100 | 100 | 90 | 100 | 0 | 100 | 100 | 30 | 20 | 100 |
| Green Foxtail | 20 | 0 | 10 | 65 | 0 | 10 | 0 | 60 | 100 | 100 | — | 100 | 0 | 100 | — | 0 | 70 | 100 |
| Johnsongrass | 20 | 0 | 0 | 40 | 40 | 0 | 0 | 90 | 100 | 100 | 100 | 100 | 0 | 100 | 100 | 0 | 20 | 30 |
| Yellow Nutsedge | 0 | 0 | 0 | 0 | 0 | 0 | 0 | 0 | 100 | 100 | 0 | — | — | — | 100 | 10 | — | 0 |

| Compound No. | 125 | 126 | 127 | 128 | 129 | 130 | 131 | 132 | 133 | 134 | 135 | 136 | 137 | 138 | 139 | 140 | 141 | 142 |
|---|---|---|---|---|---|---|---|---|---|---|---|---|---|---|---|---|---|---|
| Rate (kg/ha) | 1.0 | 4.0 | 2.0 | 2.0 | 2.0 | 4.0 | 8.0 | 2.0 | 2.0 | 2.0 | 2.0 | 2.0 | 2.0 | 2.0 | 2.0 | 2.0 | 0.125 | 2.0 |
| Species | % C | % C | % C | % C | % C | % C | % C | % C | % C | % C | % C | % C | % C | % C | % C | % C | % C | % C |
| Cotton | 100 | 100 | 100 | 100 | 100 | 100 | 0 | 100 | 100 | 100 | 100 | 70 | 100 | 100 | 100 | 100 | 100 | 100 |
| Soybean | 100 | 40 | 0 | 60 | 30 | 50 | 20 | 60 | 100 | 40 | 40 | 50 | 20 | 50 | 100 | 20 | 50 | 50 |
| Field Corn | 100 | 30 | 0 | 100 | 30 | 20 | 0 | 10 | 40 | 0 | 90 | 60 | 40 | 100 | 50 | 30 | 90 |
| Rice | 100 | 100 | 0 | 100 | 60 | 20 | — | 60 | 100 | 10 | 20 | 30 | 100 | 100 | 100 | 90 | 40 | 100 |
| Wheat | 90 | 70 | 0 | 100 | 10 | 30 | 0 | 20 | 100 | 30 | 40 | 90 | 90 | 100 | 100 | 100 | 10 | 100 |
| Field Bindweed | 100 | 100 | 10 | 100 | 100 | 100 | 0 | 100 | 100 | 100 | 100 | 100 | 100 | 100 | 100 | 100 | 80 | 100 |
| Morningglory | 100 | 100 | 10 | 100 | 100 | 100 | 0 | 80 | 100 | 80 | 90 | 80 | 100 | 90 | 100 | 100 | 80 | 100 |
| Velvetleaf | 100 | 100 | 100 | 100 | 100 | 100 | 0 | 100 | 100 | 100 | 100 | 100 | 100 | 100 | 100 | 100 | 100 | 100 |
| Barnyardgrass | 100 | 90 | 10 | 100 | 20 | 90 | 0 | 80 | 100 | 90 | 90 | 80 | 100 | 100 | 100 | 100 | 70 | 100 |
| Green Foxtail | 100 | 100 | 90 | 100 | 100 | 100 | 0 | 100 | 100 | 100 | 100 | 100 | 100 | 100 | 100 | 100 | 90 | 100 |
| Johnsongrass | 100 | 80 | 0 | 100 | 40 | 80 | 0 | 10 | 100 | 50 | 90 | 80 | 100 | 100 | 100 | 100 | 10 | 90 |
| Yellow Nutsedge | 70 | 30 | 0 | 80 | 0 | 30 | — | 10 | 100 | 0 | 10 | 50 | 80 | 70 | 100 | 60 | 20 | 80 |

| Compound No. | 143 | 144 | 145 | 146 | 147 | 148 | 149 | 150 | 151 | 152 | 153 | 154 | 155 | 156 | 157 | 158 | 159 | 160 |
|---|---|---|---|---|---|---|---|---|---|---|---|---|---|---|---|---|---|---|

TABLE 5-continued

Postemergence Herbicidal Activity

| Rate (kg/ha) | 8.0 | 4.0 | 8.0 | 8.0 | 8.0 | 8.0 | 8.0 | 8.0 | 8.0 | 1.0 | 1.0 | 2.0 | 8.0 | 8.0 | 8.0 | 8.0 | 8.0 | 1.0 |
|---|---|---|---|---|---|---|---|---|---|---|---|---|---|---|---|---|---|---|
| Species | %C | %C | %C | %C | %C | %C | %C | %C | %C | %C | %C | %C | %C | %C | %C | %C | %C | %C |
| Cotton | 30 | 100 | 90 | 90 | 20 | 10 | 80 | 40 | 20 | 100 | 100 | 100 | 100 | 80 | 40 | 100 | 100 | 100 |
| Soybean | 10 | 40 | 30 | 70 | 20 | 30 | 40 | 20 | 30 | 30 | 30 | 50 | 70 | 60 | 30 | 100 | 100 | 70 |
| Field Corn | 20 | 60 | 60 | 90 | 20 | 20 | 40 | 20 | 20 | 30 | 20 | 50 | 70 | 30 | 20 | 100 | 100 | 30 |
| Rice | — | 70 | — | — | — | — | — | — | 100' | 20 | 100 | — | — | — | — | — | — | 90 |
| Wheat | 20 | 80 | 20 | 80 | 10 | 10 | 30 | 10 | 10 | 100 | 20 | 100 | 20 | 10 | 0 | 100 | 100 | 40 |
| Field Bindweed | 10 | 90 | 20 | 30 | 0 | 0 | 80 | 0 | 10 | 100 | 90 | 100 | 100 | 20 | 0 | 100 | 100 | 100 |
| Morningglory | 20 | 90 | 50 | 100 | 20 | 20 | 60 | 50 | 20 | 100 | 90 | 100 | 100 | 80 | 20 | 100 | 100 | 90 |
| Velvetleaf | 20 | 100 | 100 | 100 | 30 | 20 | 100 | 50 | 20 | 100 | 100 | 100 | 100 | 90 | 90 | 100 | 100 | 100 |
| Barnyardgrass | 0 | 100 | 20 | 90 | 0 | 10 | 20 | 0 | 10 | 100 | 70 | 100 | 100 | — | 0 | 100 | 100 | 100 |
| Green Foxtail | 50 | 90 | 70 | 70 | 0 | 0 | 100 | 10 | 10 | 100 | 100 | 100 | 100 | 40 | 20 | 100 | 100 | 100 |
| Johnsongrass | 0 | 70 | 20 | 80 | 0 | 0 | 80 | 0 | 10 | 40 | 40 | 100 | 90 | 40 | 20 | 100 | 100 | 100 |
| Yellow Nutsedge | — | 10 | — | — | — | — | — | — | — | 30 | 20 | 90 | — | — | — | — | — | 40 |

| Compound No. | 161 | 162 | 163 | 164 | 165 | 166 | 167 | 168 | 169 | 170 | 171 | 172 | 173 | 174 | 175 | 176 | 177 | 178 |
|---|---|---|---|---|---|---|---|---|---|---|---|---|---|---|---|---|---|---|
| Rate (kg/ha) | 8.0 | 8.0 | 8.0 | 0.5 | 1.0 | 8.0 | 8.0 | 1.0 | 0.125 | 1.0 | 1.0 | 0.5 | 0.125 | 0.5 | 1.0 | 8.0 | 8.0 | 8.0 |
| Species | %C | %C | %C | %C | %C | %C | %C | %C | %C | %C | %C | %C | %C | %C | %C | %C | %C | %C |
| Cotton | 100 | 60 | 80 | 100 | 100 | 100 | 100 | 80 | 100 | 100 | 100 | 100 | 90 | 100 | 100 | 30 | 80 | 70 |
| Soybean | 100 | 30 | 40 | 50 | 40 | 80 | 70 | 20 | 80 | 50 | 50 | 60 | 40 | 90 | 80 | 20 | 50 | 40 |
| Field Corn | 100 | 0 | 30 | 60 | 40 | 90 | 100 | 30 | 30 | 50 | 10 | 90 | 60 | 100 | 60 | 10 | 60 | 20 |
| Rice | — | — | — | 80 | 60 | — | — | 80 | 50 | 40 | 100 | 40 | 60 | 50 | 90 | — | — | — |
| Wheat | 100 | 20 | 40 | 80 | 70 | 100 | 100 | 30 | 70 | 30 | 90 | 60 | 70 | 80 | 100 | 0 | 40 | 20 |
| Field Bindweed | 100 | 20 | 90 | 90 | 100 | 100 | 100 | 20 | 90 | 100 | 100 | 90 | 70 | 100 | 100 | 40 | 70 | 40 |
| Morningglory | 100 | 20 | 50 | 90 | 100 | 100 | 100 | 100 | 90 | 90 | 90 | 50 | 90 | 100 | 90 | 0 | 80 | 50 |
| Velvetleaf | 100 | 90 | 100 | 100 | 100 | 100 | 100 | 100 | 100 | 100 | 100 | 100 | 100 | 100 | 100 | 20 | 100 | 90 |
| Barnyardgrass | 100 | 0 | 60 | 60 | 100 | — | — | 80 | 50 | 40 | 100 | 90 | 60 | 100 | 100 | 30 | 70 | 40 |
| Green Foxtail | 100 | — | — | 100 | 100 | 100 | 100 | 40 | 100 | 100 | 100 | 90 | 50 | 100 | 100 | 20 | 70 | 40 |
| Johnsongrass | 100 | 20 | 40 | 30 | 40 | 100 | 100 | 30 | 50 | 40 | 50 | 80 | 60 | 90 | 100 | 20 | 80 | 50 |
| Yellow Nutsedge | — | — | — | 50 | 10 | — | — | 10 | 30 | 20 | 60 | 30 | 20 | 40 | 70 | — | 100 | — |

| Compound No. | 179 | 180 | 181 | 182 | 183 | 184 | 185 | 186 | 187 | 188 | 189 | 190 | 191 | 192 | 193 | 194 | 195 | 196 |
|---|---|---|---|---|---|---|---|---|---|---|---|---|---|---|---|---|---|---|
| Rate (kg/ha) | 4.0 | 8.0 | 8.0 | 2.0 | 1.0 | 1.0 | 1.0 | 8.0 | 0.5 | 1.0 | 1.0 | 0.125 | 1.0 | 1.0 | 1.0 | 1.0 | 1.0 | 8.0 |
| Species | %C | %C | %C | %C | %C | %C | %C | %C | %C | %C | %C | %C | %C | %C | %C | %C | %C | %C |
| Cotton | 100 | 40 | 30 | 80 | 90 | 100 | 50 | 0 | 90 | 100 | 10 | 100 | 80 | 40 | 90 | 60 | 100 | 60 |
| Soybean | 40 | 30 | 30 | 30 | 30 | 50 | 30 | 10 | 20 | 70 | 10 | 60 | 70 | 30 | 90 | 80 | 60 | 40 |
| Field Corn | 30 | 20 | 20 | 20 | 20 | 30 | 20 | 10 | 0 | 10 | 0 | 70 | 70 | 10 | 100 | 20 | 50 | 10 |
| Rice | 40 | — | — | 60 | 90 | 80 | 40 | — | 0 | 90 | 0 | 100 | 70 | 0 | 100 | 0 | 60 | — |
| Wheat | 20 | 0 | 10 | 50 | 50 | 50 | 20 | 10 | 0 | 100 | 0 | 80 | 80 | 0 | 30 | 10 | 10 | 30 |
| Field Bindweed | 100 | 50 | 0 | 90 | 100 | 100 | 70 | 0 | 50 | 100 | 0 | 100 | 90 | 80 | 100 | 100 | 100 | 100 |
| Morningglory | 100 | 40 | 30 | 80 | 90 | 100 | 60 | 0 | 20 | 90 | 0 | 30 | 90 | 10 | 100 | 30 | 100 | 30 |
| Velvetleaf | 100 | 50 | 60 | 100 | 100 | 100 | 100 | 0 | 100 | 100 | 0 | 100 | 100 | 90 | 100 | 100 | 100 | 100 |
| Barnyardgrass | 100 | 30 | 90 | 100 | 80 | 90 | 50 | 0 | 0 | 100 | 10 | 90 | 90 | 20 | 100 | 60 | 100 | 30 |
| Green Foxtail | 100 | 30 | 30 | 90 | 90 | 90 | 60 | 0 | 10 | 100 | 0 | 100 | 100 | 100 | 100 | 80 | 100 | 30 |
| Johnsongrass | 50 | 30 | 0 | 50 | 50 | 40 | 60 | 0 | 60 | 80 | 0 | 70 | 90 | 70 | 100 | 20 | 70 | 20 |
| Yellow Nutsedge | 20 | — | — | 60 | 30 | 50 | 20 | — | 0 | 90 | 0 | 40 | 10 | 0 | 70 | 0 | 20 | — |

| Compound No. | 197 | 198 | 199 | 200 | 201 | 202 | 203 | 204 | 205 | 206 | 207 | 208 | 209 | 210 | 212 | 213 | 214 | 215. |
|---|---|---|---|---|---|---|---|---|---|---|---|---|---|---|---|---|---|---|
| Rate (kg/ha) | 8.0 | 8.0 | 0.5 | 2.0 | 2.0 | 2.0 | 0.5 | 0.5 | 0.5 | 0.25 | 4.0 | 0.5 | 1.0 | 8.0 | 8.0 | 8.0 | 8.0 | 8.0 |
| Species | %C | %C | %C | %C | %C | %C | %C | %C | %C | %C | %C | %C | %C | %C | %C | %C | %C | %C |
| Cotton | 80 | 90 | 90 | 60 | 90 | 90 | 90 | 90 | 100 | 100 | 90 | 100 | 100 | 0 | 0 | 10 | 0 | 100 |
| Soybean | 30 | 20 | 40 | 60 | 90 | 40 | 80 | 80 | 50 | 70 | 90 | 60 | 40 | 0 | 0 | 10 | 0 | 100 |
| Field Corn | 30 | 10 | 20 | 40 | 20 | 30 | 70 | 80 | 40 | 40 | 30 | 30 | 20 | 0 | 0 | 10 | 0 | 100 |
| Rice | — | — | 10 | 10 | 20 | 10 | 30 | 40 | 40 | 70 | 20 | 50 | 100 | — | — | — | — | 100 |
| Wheat | 50 | 40 | 50 | 0 | 40 | 10 | 50 | 100 | 90 | 60 | 30 | 70 | 90 | 0 | 0 | 0 | 0 | 100 |
| Field Bindweed | 100 | 100 | 90 | 20 | 60 | 10 | 100 | 90 | 90 | 100 | 40 | 90 | 100 | 0 | 0 | 0 | 0 | 100 |
| Morningglory | 80 | 60 | 90 | 20 | 10 | 60 | 90 | 100 | 90 | 100 | 30 | 100 | 100 | 0 | 0 | 80 | 0 | 100 |
| Velvetleaf | 100 | 100 | 100 | 10 | 100 | 100 | 100 | 100 | 100 | 100 | 100 | 100 | 100 | 0 | 0 | 0 | 0 | 100 |
| Barnyardgrass | 80 | 40 | 0 | 10 | 10 | 0 | — | — | — | — | 60 | 100 | 100 | 0 | 0 | 0 | 0 | 100 |
| Green Foxtail | 100 | 50 | 100 | 70 | 90 | 50 | 80 | 100 | 100 | 100 | 40 | 90 | 100 | 0 | 0 | 0 | 0 | 100 |
| Johnsongrass | 60 | 30 | 10 | 0 | 30 | 0 | 40 | 70 | 50 | 90 | 20 | 70 | 70 | 0 | 0 | 0 | 0 | 100 |
| Yellow Nutsedge | — | — | 0 | 0 | 10 | 0 | 40 | 50 | 60 | 40 | 30 | 30 | 70 | — | — | — | — | 80 |

| Compound No. | 216 | 217 | 218 | 219 | 220 | 221 | 222 | 223 | 224 | 225 |
|---|---|---|---|---|---|---|---|---|---|---|
| Rate (kg/ha) | 2.0 | 8.0 | 0.5 | 0.5 | 2.0 | 1.0 | 1.0 | 1.0 | 0.5 | 0.5 |
| Species | %C | %C | %C | %C | %C | %C | %C | %C | %C | %C |
| Cotton | 100 | 80 | 100 | 90 | 100 | 100 | 100 | 95 | 100 | 100 |
| Soybean | 90 | 40 | 60 | 60 | 90 | 90 | 90 | 50 | 95 | 100 |
| Field Corn | 90 | 10 | 70 | 60 | 50 | 90 | 80 | 50 | 100 | 100 |
| Rice | 90 | — | 90 | 50 | 100 | 95 | 60 | 40 | 95 | 90 |
| Wheat | 100 | 20 | 60 | 70 | 60 | 90 | 70 | 30 | 100 | 95 |
| Field Bindweed | 100 | 80 | 100 | 100 | 100 | 100 | 90 | 70 | 100 | 100 |
| Morningglory | 100 | 70 | 100 | 100 | 100 | 100 | 90 | 95 | 100 | 100 |
| Velvetleaf | 100 | 100 | 100 | 100 | 100 | 100 | 100 | 80 | 100 | 100 |
| Barnyardgrass | 100 | 40 | 90 | 100 | 60 | 100 | 100 | 30 | 100 | 100 |
| Green Foxtail | 100 | 20 | 100 | 60 | 50 | 95 | 100 | 10 | 100 | 100 |
| Johnsongrass | 100 | 10 | 90 | 90 | 60 | 90 | 70 | 20 | 100 | 100 |
| Yellow Nutsedge | 80 | — | 90 | 40 | 40 | 40 | 30 | 10 | 95 | 40 |

TABLE 1'

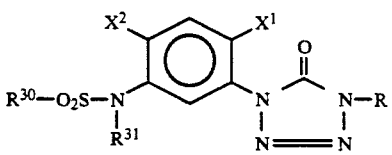

| Cmpd No. | $R^{30}$ | $R^{31}$ | $X^1$ | $X^2$ | R |
|---|---|---|---|---|---|
| 1' | $CH_3$ | H | Cl | Cl | $(CH_2)_2CH_2F$ |
| 2' | $CH_3$ | H | F | Cl | $(CH_2)_2CH_2F$ |
| 3' | $C_2H_5$ | H | Cl | Cl | $(CH_2)_2CH_2F$ |
| 4' | $C_2H_5$ | H | F | Cl | $(CH_2)_2CH_2F$ |
| 5' | $C_3H_7$ | H | Cl | Cl | $(CH_2)_2CH_2F$ |
| 6' | $CH_3$ | $SO_2CH_3$ | H | Cl | $(CH_2)_2CH_2F$ |
| 7' | $CH_3$ | $SO_2CH_3$ | Cl | Cl | $(CH_2)_2CH_2F$ |
| 8' | $CH_3$ | $SO_2CH_3$ | F | F | $(CH_2)_2CH_2F$ |
| 9' | $CH_3$ | $SO_2CH_3$ | F | Cl | $(CH_2)_2CH_2F$ |
| 10' | $CH_3$ | $SO_2CH_3$ | F | Br | $(CH_2)_2CH_2F$ |
| 11' | $CH_3$ | $SO_2C_2H_5$ | F | Cl | $(CH_2)_2CH_2F$ |
| 12' | $C_2H_5$ | $CH_3$ | F | Cl | $(CH_2)_2CH_2F$ |
| 13' | $C_2H_5$ | $C_2H_5$ | F | Cl | $(CH_2)_2CH_2F$ |
| 14' | $C_2H_5$ | $C_3H_7$ | F | Cl | $(CH_2)_2CH_2F$ |
| 15' | $C_2H_5$ | $CH_2OCH_3$ | F | Cl | $(CH_2)_2CH_2F$ |
| 16' | $C_2H_5$ | $CH_2C\equiv N$ | F | Cl | $(CH_2)_2CH_2F$ |
| 17' | $C_2H_5$ | $CH_2CO_2C_2H_5$ | F | Cl | $(CH_2)_2CH_2F$ |
| 18' | $C_2H_5$ | $SO_2C_2H_5$ | H | Cl | $(CH_2)_2CH_2F$ |
| 19' | $C_2H_5$ | $SO_2C_2H_5$ | Cl | Cl | $(CH_2)_2CH_2F$ |
| 20' | $C_2H_5$ | $SO_2C_2H_5$ | F | F | $(CH_2)_2CH_2F$ |
| 21' | $C_2H_5$ | $SO_2C_2H_5$ | F | Cl | $(CH_2)_2CH_2F$ |
| 22' | $C_2H_5$ | $SO_2C_2H_5$ | F | Br | $(CH_2)_2CH_2F$ |
| 23' | $C_3H_7$ | $SO_2C_3H_7$ | H | Cl | $(CH_2)_2CH_2F$ |
| 24' | $C_3H_7$ | $SO_2C_3H_7$ | Cl | Cl | $(CH_2)_2CH_2F$ |
| 25' | $C_3H_7$ | $SO_2C_3H_7$ | F | F | $(CH_2)_2CH_2F$ |
| 26' | $C_3H_7$ | $SO_2C_3H_7$ | F | Cl | $(CH_2)_2CH_2F$ |
| 27' | $C_3H_7$ | $SO_2C_3H_7$ | F | Br | $(CH_2)_2CH_2F$ |
| 28' | $C_3H_7$ | H | F | Cl | $(CH_2)_2CH_2F$ |
| 29' | $C_3H_7$ | $CH_3$ | F | Cl | $(CH_2)_2CH_2F$ |
| 30' | $CF_3$ | H | F | Cl | $(CH_2)_2CH_2F$ |
| 31' | $C_2H_5$ | K | F | Cl | $(CH_2)_2CH_2F$ |
| 32' | $CF_3$ | K | F | Cl | $(CH_2)_2CH_2F$ |
| 33' | $CH_3$ | H | F | Br | $(CH_2)_2CH_2F$ |
| 34' | $C_2H_5$ | H | F | Br | $(CH_2)_2CH_2F$ |
| 35' | $CF_3$ | H | Cl | Cl | $(CH_2)_2CH_2F$ |
| 36' | $CH_3$ | $SO_2CH_3$ | Cl | F | $(CH_2)_2CH_2F$ |
| 37' | $C_2H_5$ | $SO_2C_2H_5$ | Cl | F | $(CH_2)_2CH_2F$ |
| 38' | $CH_3$ | H | Cl | F | $(CH_2)_2CH_2F$ |

TABLE 1'-continued

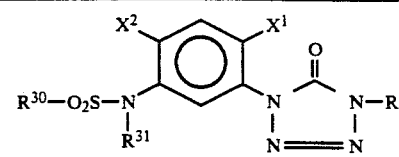

| Cmpd No. | $R^{30}$ | $R^{31}$ | $X^1$ | $X^2$ | R |
|---|---|---|---|---|---|
| 39' | $C_2H_5$ | H | Cl | F | $(CH_2)_2CH_2F$ |
| 40' | $CH_3$ | $SO_2CH_3$ | F | Cl | $CH_3$ |
| 41' | $C_2H_5$ | $SO_2C_2H_5$ | F | Cl | $CH_3$ |
| 42' | $CH_3$ | H | F | Cl | $CH_3$ |
| 43' | $C_2H_5$ | H | F | Cl | $CH_3$ |
| 44' | $CH_3$ | $SO_2CH_3$ | F | Cl | $C_2H_5$ |
| 45' | $C_2H_5$ | $SO_2C_2H_5$ | F | Cl | $C_2H_5$ |
| 46' | $CH_3$ | H | F | Cl | $C_2H_5$ |
| 47' | $C_2H_5$ | H | F | Cl | $C_2H_5$ |
| 48' | $CH_3$ | $SO_2CH_3$ | F | Cl | $C_3H_7$ |
| 49' | $C_2H_5$ | $SO_2C_2H_5$ | F | Cl | $C_3H_7$ |
| 50' | $CH_3$ | H | F | Cl | $C_3H_7$ |
| 51' | $C_2H_5$ | H | F | Cl | $C_3H_7$ |
| 52' | $C_2H_5$ | $SO_2C_2H_5$ | $CH_3$ | $CH_3$ | $(CH_2)_2CH_2F$ |
| 53' | $C_2H_5$ | H | $CH_3$ | $CH_3$ | $(CH_2)_2CH_2F$ |
| 54' | $C_2H_5$ | $CHF_2$ | F | Cl | $(CH_2)_2CH_2F$ |
| 55' | $C_2H_5$ | $CH_2CH_2CH_2F$ | F | Cl | $(CH_2)_2CH_2F$ |

The compounds in which Z is ethylsulfonylamino, such as compounds 4', 31' and 34', have been found to be particularly useful when used pre-emergently against broad leaf weeds with crops such as corn, rice wheat and soybeans. Compounds in which Z is bis(N-ethylsulfonyl)amino, such as compound 21', have been found to be particularly suitable when used post-emergently against broad leaf weeds in soybean fields.

Other representative compounds are those which are identical with compounds 5',11'–17',28'–32',35',40'–51', 54' and 55' respectively except that $X^1$ is F and $X^2$ is Br. Other representative compounds are those which are identical with compounds 1'–55' respectively except that $X^1$ is F and $X^2$ is $CF_3$. Still other representative compounds are those which are identical with compounds 1'–55' respectively except that $X^1$ is Br.

TABLE 2'

| Compound Number | Name | Empirical Formula/ m.p. (°C.) | Elemental Analysis C | H | N |
|---|---|---|---|---|---|
| 1' | 1-[2,4-dichloro-5-(N-methylsulfonyl)amino]-phenyl]-1,4-dihydro-4-(3-fluoropropyl)-5H-tetrazol-5-one | $C_{11}H_{12}Cl_2FN_5O_3S$ Liquid | | | |
| 2' | 1-[4-chloro-2-fluoro-5-(N-methylsulfonyl-amino)phenyl]-1,4-dihydro-4-(3-fluoro-propyl)-5H-tetrazol-5-one | $C_{11}H_{12}ClF_2N_5O_3S$ 106–109 | Calcd 35.92 Found 35.69 | 3.29 3.30 | 19.04 18.89 |
| 3' | 1-[2,4-dichloro-5-(N-ethylsulfonylamino)-phenyl]-1,4-dihydro-4-(3-fluoropropyl)-5H-tetrazol-5-one | $C_{12}H_{14}Cl_2FN_5O_3S$ 71–73 | Calcd 36.20 Found 36.40 | 3.55 3.50 | 17.63 17.50 |
| 4' | 1-[4-chloro-2-fluoro-5-(N-ethylsulfonyl-amino)phenyl]-1,4-dihydro-4-(3-fluoropropyl)-5H-tetrazol-5-one | $C_{12}H_{14}ClF_2N_5O_3S$ 84–85 | Calcd 37.39 Found 37.80 | 3.94 3.58 | 18.29 18.21 |
| 5' | 1-[2,4-dichloro-5-(N-propylsulfonylamino)-phenyl]-1,4-dihydro-4-(3-fluoropropyl)-5H-tetrazol-5-one | $C_{13}H_{16}Cl_2FN_5O_3S$ Liquid | | | |
| 6' | 1-[4-chloro-3-[bis(methylsulfonyl)amino]-phenyl]-1,4-dihydro-4-(3-fluoropropyl)-5H-tetrazol-5-one | $C_{12}H_{15}ClFN_5O_5S_2$ 171–172 | Calcd 33.68 Found 33.57 | 3.53 3.61 | 16.37 16.16 |
| 7' | 1-[2,4-dichloro-5-[bis(N-methylsulfonyl)-amino]phenyl]-1,4-dihydro-4-(3-fluoropropyl)-5H-tetrazol-5-one | $C_{12}H_{14}Cl_2FN_5O_5S_2$ 176–177 | Calcd 31.18 Found 31.40 | 3.05 2.54 | 15.15 15.13 |
| 8' | 1-[2,4-difluoro-5-[bis(N-methylsulfonyl)-amino]phenyl]-1,4-dihydro-4-(3-fluoropropyl)-5H-tetrazol-5-one | $C_{12}H_{14}F_3N_5O_5S_2$ 138–140 | Calcd 33.57 Found 33.88 | 3.28 3.21 | 16.31 16.23 |
| 9' | 1-[4-chloro-2-fluoro-5-[bis(N-methylsulfonyl)-amino]phenyl]-1,4-dihydro-4-(3-fluoropropyl)-5H-tetrazol-5-one | $C_{12}H_{14}ClF_2N_5O_5S_2$ 92–94 | | | |
| 10' | 1-(4-bromo-2-fluoro-5-[bis(N-methylsulfonyl)-amino]phenyl]-1,4-dihydro-4-(3-fluoropropyl)- | $C_{12}H_{14}BrF_2N_5O_5S_2$ 143–144 | Calcd 29.39 Found 29.54 | 2.88 2.81 | 14.28 14.20 |

TABLE 2'-continued

| Compound Number | Name | Empirical Formula/ m.p. (°C.) | Elemental Analysis | | | |
|---|---|---|---|---|---|---|
| | | | | C | H | N |
| 11' | 5H-tetrazol-5-one<br>1-[4-chloro-2-fluoro-5-[(N-ethylsulfonyl-N-methylsulfonyl)amino]phenyl]-1,4-dihydro-4-(3-fluoropropyl)-5H-tetrazol-5-one | $C_{13}H_{16}ClF_2N_5O_5S_2$<br>124.5–126 | Calcd<br>Found | 33.95<br>33.86 | 3.51<br>3.47 | 15.23<br>15.50 |
| 12' | 1-[4-chloro-2-fluoro-5-[(N-ethylsulfonyl-N-methyl)amino]phenyl]-1,4-dihydro-4-(3-fluoropropyl)-5H-tetrazol-5-one | $C_{13}H_{16}ClF_2N_5O_5S$<br>75–77 | Calcd<br>Found | 39.44<br>39.47 | 4.07<br>3.75 | 17.69<br>17.42 |
| 13' | 1-[4-chloro-2-fluoro-5-[(N-ethyl-N-ethylsulfonyl)amino]phenyl]-1,4-dihydro-4-(3-fluoropropyl)-5H-tetrazol-5-one | $C_{14}H_{18}ClF_2N_5O_3S$<br>Liquid | Calcd<br>Found | 41.02<br>41.72 | 4.42<br>4.54 | 17.09<br>16.21 |
| 14' | 1-[4-chloro-2-fluoro-5-[(N-ethylsulfonyl-N-propyl)amino]phenyl]-1,4-dihydro-4-(3-fluoropropyl)-5H-tetrazol-5-one | $C_{15}H_{20}ClF_2N_5O_3S$<br>Liquid | Calcd<br>Found | 42.51<br>41.84 | 4.76<br>4.50 | 16.52<br>16.07 |
| 15' | 1-[4-chloro-2-fluoro-5-[(N-ethylsulfonyl-N-methoxymethyl)amino]phenyl]-1,4-dihydro-4-(3-fluoropropyl)-5H-tetrazol-5-one | $C_{14}H_{18}ClF_2N_5O_4S$<br>Liquid | Calcd<br>Found | 39.49<br>38.71 | 4.26<br>3.97 | 16.44<br>15.48 |
| 16' | 1-[4-chloro-2-fluoro-5-[(N-cyanomethyl-N-ethylsulfonyl)amino]phenyl]-1,4-dihydro-4-(3-fluoropropyl)-5H-tetrazol-5-one | $C_{14}H_{15}ClF_2N_6O_3S$<br>Liquid | Calcd<br>Found | 39.95<br>40.16 | 3.59<br>3.54 | 19.97<br>18.03 |
| 17' | ethyl [2-chloro-4-fluoro-5-[1,4-dihydro-5-oxo-4-(3-fluoropropyl)tetrazol-1-yl]-phenyl(N-ethylsulfonyl)amino]acetate | $C_{16}H_{20}ClF_2N_5O_5S$<br>Liquid | Calcd<br>Found | 41.07<br>39.41 | 4.30<br>4.45 | 14.96<br>13.54 |
| 18' | 1-[4-chloro-3-[bis(N-ethylsulfonyl)amino]-phenyl]-1,4-dihydro-4-(3-fluoropropyl)-5H-tetrazol-5-one | $C_{14}H_{19}ClFN_5O_5S_2$<br>141–143 | Calcd<br>Found | 36.88<br>36.68 | 4.20<br>4.24 | 15.36<br>15.16 |
| 19' | 1-[2,4-dichloro-5-[bis(N-ethylsulfonyl)-amino]phenyl]-1,4-dihydro-4-(3-fluoropropyl)-5H-tetrazol-5-one | $C_{14}H_{18}ClFN_5O_5S_2$<br>165–166 | Calcd<br>Found | 34.30<br>34.41 | 3.70<br>3.57 | 14.28<br>14.27 |
| 20' | 1-(2,4-difluoro-5-[bis(N-ethylsulfonyl)-amino]phenyl]-1,4-dihydro-4-(3-fluoropropyl)-5H-tetrazol-5-one | $C_{14}H_{18}F_3N_5O_5S_2$<br>Liquid | Calcd<br>Found | 36.76<br>37.02 | 3.96<br>3.85 | 15.31<br>14.79 |
| 21' | 1-[4-chloro-2-fluoro-5-[bis(N-ethylsulfonyl)-amino]phenyl]-1,4-dihydro-4-(3-fluoropropyl)-5H-tetrazol-5-one | $C_{14}H_{18}ClF_2N_5O_5S_2$<br>127–129 | Calcd<br>Found | 35.48<br>35.75 | 3.83<br>3.73 | 14.78<br>14.83 |
| 22' | 1-[4-bromo-2-fluoro-5-[bis(N-ethylsulfonyl)-amino]phenyl]-1,4-dihydro-4-(3-fluoropropyl)-5H-tetrazol-5-one | $C_{14}H_{18}BrF_2N_5O_5S_2$<br>163–164 | Calcd<br>Found | 32.44<br>32.63 | 3.50<br>3.53 | 13.51<br>13.51 |
| 23' | 1-[4-chloro-3-[bis(N-propylsulfonyl)amino]-phenyl]-1,4-dihydro-4-(3-fluoropropyl)-5H-tetrazol-5-one | $C_{16}H_{23}ClFN_5O_5S_2$<br>Liquid | Calcd<br>Found | 39.70<br>38.60 | 4.79<br>4.92 | 14.47<br>13.96 |
| 24' | 1-[2,4-dichloro-5-[bis(N-propylsulfonyl)-amino]phenyl]-1,4-dihydro-4-(3-fluoropropyl)-5H-tetrazol-5-one | $C_{16}H_{22}Cl_2FN_5O_5S_2$<br>128–129 | Calcd<br>Found | 37.08<br>37.09 | 4.27<br>3.90 | 13.51<br>13.43 |
| 25' | 1-[2,4-difluoro-5-[bis(N-propylsulfonyl)-amino]phenyl]-1,4-dihydro-4-(3-fluoropropyl)-5H-tetrazol-5-one | $C_{16}H_{22}F_3N_5O_5S_2$<br>Liquid | Calcd<br>Found | 39.59<br>40.19 | 4.56<br>4.62 | 14.42<br>14.15 |
| 26' | 1-[4-chloro-2-fluoro-5-[bis(N-propylsulfonyl)-amino]phenyl]-1,4-dihydro-4-(3-fluoropropyl)-5H-tetrazol-5-one | $C_{16}H_{22}ClF_2N_5O_5S_2$<br>Liquid | Calcd<br>Found | 38.29<br>39.41 | 4.42<br>4.54 | 13.95<br>13.83 |
| 27' | 1-[4-bromo-2-fluoro-5-[bis(N-propylsulfonyl)-amino]phenyl]-1,4-dihydro-4-(3-fluoropropyl)-5H-tetrazol-5-one | $C_{16}H_{22}BrF_2N_5O_5S_2$<br>106–107 | Calcd<br>Found | 35.17<br>35.83 | 4.06<br>3.90 | 12.81<br>12.62 |

TABLE 3'

Preemergence Herbicidal Activity

| | Compound No. | | | | | | | | | | | | | | | | | |
|---|---|---|---|---|---|---|---|---|---|---|---|---|---|---|---|---|---|---|
| | 2' | 4' | 6' | 8' | 9' | 10' | 11' | 12' | 13' | 14' | 15' | 16' | 17' | 18' | 20' | 21' | 22' | 23' |
| | Rate (kg/ha) | | | | | | | | | | | | | | | | | |
| | 0.25<br>C | 0.25<br>C | 8.0<br>C | 0.5<br>C | 1.0<br>C | 1.0<br>C | 0.5<br>C | 0.5<br>C | 1.0<br>C | 1.0<br>C | 0.5<br>C | 0.5<br>C | 1.0<br>C | 8.0<br>C | 0.5<br>C | 0.5<br>C | 1.0<br>C | 8.0<br>C |
| Cotton | 95 | 95 | 70 | 95 | 100 | 100 | 100 | 100 | 95 | 100 | 100 | 100 | 10 | 100 | 80 | 95 | 100 | 30 |
| Soybean | 20 | 0 | 30 | 30 | 50 | 80 | 30 | 80 | 95 | 95 | 95 | 80 | 10 | 10 | 20 | 20 | 60 | 10 |
| Field Corn | 40 | 30 | 20 | 40 | 100 | 95 | 95 | 100 | 100 | 100 | 100 | 95 | 10 | 0 | 90 | 90 | 95 | 90 |
| Rice | 70 | 40 | | 70 | | 95 | 80 | 90 | 100 | 100 | 100 | 70 | 10 | | 70 | 80 | 80 | 20 |
| Wheat | 10 | 10 | 0 | 10 | 90 | 90 | 80 | 100 | 100 | 100 | 100 | 60 | 20 | 0 | 30 | 95 | 90 | 40 |
| Field Bindweed | 100 | 100 | 20 | 40 | | 100 | 100 | 100 | 100 | 100 | 100 | 100 | 10 | 30 | 20 | | 100 | 70 |
| Morningglory | 100 | 100 | 60 | 60 | 100 | 100 | 100 | 100 | 95 | 100 | 100 | 100 | 30 | 40 | 70 | 95 | 100 | 70 |
| Velvetleaf | 100 | 100 | 95 | 100 | 100 | 100 | 100 | 100 | 100 | 100 | 100 | 100 | 90 | 95 | 100 | 100 | 100 | 100 |
| Barnyardgrass | 60 | 80 | 30 | 40 | 100 | 100 | 100 | 100 | 100 | 100 | 100 | 90 | 20 | 20 | 90 | 100 | 100 | 80 |
| Green Foxtail | 40 | 20 | 30 | 50 | 100 | 100 | 100 | 100 | 100 | 100 | 100 | 80 | 30 | 10 | 95 | 100 | 100 | 95 |
| Johnsongrass | 40 | 30 | 20 | 50 | 80 | 95 | 90 | 100 | 100 | 100 | 100 | 90 | 60 | 40 | 90 | 100 | 100 | 50 |

| | Compound No. | | | | | | | | |
|---|---|---|---|---|---|---|---|---|---|
| | 25' | 26' | 27' | 28' | 29' | 30' | 31' | 32' | 33' |
| | Rate (kg/ha) | | | | | | | | |
| | 0.5 | 0.500 | 1.0 | 0.5 | 0.25 | 0.25 | 0.25 | 2.0 | 0.25 |

TABLE 3'-continued

| Preemergence Herbicidal Activity | | | | | | | | | |
|---|---|---|---|---|---|---|---|---|---|
| | C | C | C | C | C | C | C | C | C |
| Cotton | 10 | 50 | 95 | 100 | 60 | 50 | 100 | 100 | 100 |
| Soybean | 20 | 0 | 30 | 0 | 30 | 10 | 10 | 40 | 10 |
| Field Corn | 80 | 90 | 95 | 30 | 95 | 10 | 30 | 50 | 40 |
| Rice | 20 | 20 | 60 | 70 | 60 | 20 | 40 | 95 | 80 |
| Wheat | 20 | 60 | 60 | 30 | 80 | 0 | 20 | 10 | 20 |
| Field Bindweed | 0 | | 100 | 100 | 70 | 95 | 100 | 100 | 100 |
| Morningglory | 10 | 60 | 100 | 100 | 70 | 60 | 100 | 100 | 100 |
| Velvetleaf | 20 | 100 | 100 | 100 | 100 | 100 | 100 | 100 | 100 |
| Barnyardgrass | 50 | 100 | 100 | 95 | 100 | 0 | 95 | 95 | 95 |
| Green Foxtail | 10 | 60 | 100 | 90 | 100 | 10 | 50 | 60 | 70 |
| Johnsongrass | 60 | 95 | 95 | 70 | 100 | 60 | 70 | 80 | 70 |

Numbers below the letter "C" are for percent control of the particular species of plant.

TABLE 4'

POSTEMERGENCE EVALUATIONS

| Compound No. | | | | | | | | | | | | |
|---|---|---|---|---|---|---|---|---|---|---|---|---|
| 2' | 4' | 6' | 8' | 9' | 10' | 11' | 12' | 13' | 14' | 15' | 16' | 17' |
| Rate (kg/ha) | | | | | | | | | | | | |
| 0.25 | 0.25 | 8.0 | 0.5 | 1.0 | 1.0 | 0.5 | 0.5 | 1.0 | 1.0 | 0.5 | 0.5 | 1.0 |
| C | C | C | C | C | C | C | C | C | C | C | C | C |

| | 2' | 4' | 6' | 8' | 9' | 10' | 11' | 12' | 13' | 14' | 15' | 16' | 17' |
|---|---|---|---|---|---|---|---|---|---|---|---|---|---|
| Cotton | 100 | 100 | 90 | 95 | 100 | 100 | 100 | 100 | 100 | 100 | 100 | 100 | 90 |
| Soybean | 50 | 60 | 50 | 40 | 30 | 95 | 60 | 70 | 95 | 100 | 95 | 70 | 50 |
| Field Corn | 80 | 50 | 40 | 50 | 30 | 90 | 80 | 70 | 100 | 100 | 95 | 50 | 60 |
| Rice | 50 | 20 | 30 | 20 | | 30 | 40 | 30 | 100 | 100 | 60 | 50 | 20 |
| Wheat | 20 | 20 | 20 | 30 | 80 | 60 | 70 | 80 | 100 | 100 | 100 | 60 | 40 |
| Field Bindweed | 100 | 100 | 70 | 30 | | 100 | 100 | 100 | 100 | 100 | 80 | 100 | 80 |
| Morningglory | 100 | 95 | 100 | 40 | 100 | 100 | 80 | 100 | 100 | 100 | 100 | 100 | 60 |
| Velvetleaf | 100 | 100 | 100 | 95 | 100 | 100 | 100 | 100 | 100 | 100 | 100 | 100 | 95 |
| Barnyardgrass | 40 | 50 | 50 | 40 | 100 | 100 | 80 | 70 | 100 | 100 | 80 | 50 | 40 |
| Green Foxtail | 50 | 80 | 50 | 50 | 60 | 100 | 80 | 70 | 100 | 100 | 90 | 70 | 40 |
| Johnsongrass | 50 | 20 | 20 | 30 | 70 | 100 | 50 | 70 | 100 | 100 | 80 | 60 | 40 |

| Compound No. | | | | | | | | | | | | |
|---|---|---|---|---|---|---|---|---|---|---|---|---|
| 18' | 20' | 22' | 23' | 25' | 26' | 27' | 28' | 29' | 30' | 31' | 32' | 33' |
| Rate (kg/ha) | | | | | | | | | | | | |
| 8.0 | 0.5 | 1.0 | 8.0 | 0.5 | 0.50 | 1.0 | 0.5 | 0.25 | 0.25 | 0.25 | 2.0 | 0.25 |
| C | C | C | C | C | C | C | C | C | C | C | C | C |

| | 18' | 20' | 22' | 23' | 25' | 26' | 27' | 28' | 29' | 30' | 31' | 32' | 33' |
|---|---|---|---|---|---|---|---|---|---|---|---|---|---|
| Cotton | 60 | 90 | 100 | 60 | 40 | 100 | 100 | 100 | 70 | 90 | 100 | 100 | 100 |
| Soybean | 60 | 30 | 95 | 40 | 20 | 50 | 90 | 30 | 70 | 40 | 80 | 100 | 70 |
| Field Corn | 30 | 20 | 100 | 30 | 60 | 100 | 95 | 40 | 40 | 30 | 30 | 70 | 30 |
| Rice | | 20 | 80 | | 20 | 40 | 30 | 70 | 60 | 10 | 40 | 40 | 80 |
| Wheat | 10 | 50 | 90 | 20 | 20 | 90 | 80 | 60 | 80 | 10 | 40 | 40 | 40 |
| Field Bindweed | 50 | 30 | 95 | 50 | 40 | | 95 | 100 | 80 | 70 | 100 | 100 | 100 |
| Morningglory | 70 | 90 | 95 | 60 | 30 | 100 | 100 | 100 | 70 | 80 | 100 | 100 | 100 |
| Velvetleaf | 95 | 100 | 100 | 100 | 80 | 100 | 100 | 100 | 100 | 100 | 100 | 100 | 100 |
| Barnyardgrass | 30 | 30 | 100 | 40 | 20 | 80 | 100 | 100 | 50 | 10 | 80 | 70 | 80 |
| Green Foxtail | 30 | 40 | 100 | 40 | 30 | 80 | 100 | 100 | 60 | 0 | 60 | 40 | 100 |
| Johnsongrass | 30 | 30 | 100 | 40 | 20 | 70 | 100 | 95 | 70 | 0 | 60 | 70 | 70 |

Numbers below the letter "C" are for percent control of the particular species of plant.

I claim:

1. A compound of the formula

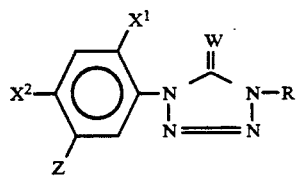

in which W is oxygen or sulfur;

R is alkyl of 1 to 6 carbon atoms, fluoroalkyl of 1 to 5 carbon atoms and one or more fluorine atoms, alkoxyalkyl of 2 to 6 carbon atoms, alkylthioalkyl of 2 to 6 carbon atoms, cyanoalkyl of 1 to 5 alkyl carbon atoms, haloalkoxyalkyl of 2 to 6 carbon atoms, trifluoromethylthio, alkenyl of 2 to 5 carbon atoms, or haloalkenyl of 2 to 5 carbon atoms;

one of $X^1$ and $X^2$ is fluorine, chlorine, or bromine and the other is fluorine, chlorine, bromine, alkyl of 1 to 6 carbon atoms, or haloalkyl of 1 to 5 carbon atoms; or $X^1$ is fluorine, chlorine, or bromine and $X^2$ is selected from the substituents above and nitro; and Z is selected from fluorine, chlorine, bromine, cyano, nitro, amino, alkyl of 1 to 6 carbon atoms, alkyl of 1 to 5 carbon atoms (substituted with fluorine, chlorine, bromine, or alkoxy of 1 to 4 carbons), alkynyl of 3 to 5 carbon atoms, $-QR^1$, $OSO_2R^2$, $-QR^7CO-Q^1R^8$, $-QR^7CO_2N=C(R^9)(R^{10})$, $-QR^7C(CH_3)=R^{11}$, $-QR^7CON(R^{12})(R^{13})$, $-N(R^{14})(R^{15})$, $-SO_2R^{16}$, and $-CO-R^{17}$;

Q and Q1 are independently oxygen or sulfur;

$R^1$ is alkyl of 1 to 6 carbon atoms, haloalkyl of 1 to 5 carbon atoms, hydroxyalkyl of 2 to 5 carbon atoms, cyanoalkyl of 1 to 5 alkyl carbon atoms, alkoxyalkyl of 2 to 6 carbon atoms, alkylthioalkyl, alkylsulfinylalkyl, or alkylsulfonylalkyl (each of 2 to 6 carbon atoms), alkanoyl of 2 to 5 carbon atoms, alkenyl of 2 to 5 carbon atoms, haloalkenyl of 2 to 5 carbon atoms, alkenyloxyalkyl of 3 to 6 carbon atoms, alkynyl of 2 to 5 carbon atoms, haloalkynyl of 2 to 5 carbon atoms, alkoxycarbonyl of 1 to 4 alkyl carbon atoms, or a three- to eight-membered saturated ring heterocyclic group selected from tetrahydrofurans, thiotetrahydrofurans, epoxides, thioepoxides, thioacetals, and benzodioxanes, or an alkyl radical of 1 to 4 carbon atoms substituted with said heterocyclic group;

$R^2$ is alkyl of 1 to 8 carbon atoms, haloalkyl, cyanoalkyl, or arylalkyl wherein each alkyl is of 1 to 5 carbon atoms, cyclic alkyl of 3 to 8 carbon atoms, alkenyl, haloalkenyl, or arylalkenyl wherein each alkenyl is of 2 to 5 carbon atoms, alkynyl, haloalkynyl, or arylalkynyl wherein each alkynyl is of 2 to 5 carbon atoms, phenyl, or a group of the formula —$(CH_2)_m NR^3 R^4$ or $(CH_2)_n$—Y—$R^5$ wherein m is 0 to 5 and n is 1 to 5;

$R^3$ is hydrogen or alkyl of 1 to 5 carbon atoms;

$R^4$ is alkyl of 1 to 5 carbon atoms or a group —$CH_2$—Y—$R^5$;

$R^5$ is alkyl of 1 to 5 carbon atoms, alkenyl or alkynyl of 2 to 5 carbon atoms, or a radical —$CH(R^{18})CO_2 R^{19}$;

$R^{18}$ and $R^{19}$ are independently hydrogen or alkyl of 1 to 4 carbon atoms; and Y is oxygen or $S(O)_r$ in which r is 0 to 2;

$R^7$ is alkylene or fluoroalkylene radical of 1 to 3 carbon atoms;

$R^8$ is hydrogen, alkyl or substituted alkyl of 1 to 8 carbon atoms, alkenyl or alkynyl of 2 to 5 carbon atoms, aromatic, or a monovalent cyclic group of 3 to 7 ring atoms which is heterocyclic, or alicyclic, the valence being on a carbon atom of said cyclic group, or an alkyl radical of 1 to 3 carbon atoms substituted with said cyclic group, wherein said heterocyclic group is 3-tetrahydrofuranyl, 2-oxo-3-tetrahydrofuranyl, 3-tetrahydrothienyl or the oxide or dioxide thereof, or 3-pyridyl;

one of $R^9$ and $R^{10}$ is alkyl and the other is alkyl or alkylthio, each alkyl (independently) being of 1 to 4 carbon atoms;

$R^{11}$ is oxygen or N-$OR^{20}$ in which $R^{20}$ is hydrogen or alkyl of 1 to 4 carbon atoms;

one of $R^{12}$ and $R^{13}$ is hydrogen, alkyl of 1 to 4 carbon atoms, or alkenyl of 3 to 5 carbon atoms and the other is hydrogen, alkyl of 1 to 4 carbon atoms, cyanoalkyl of 1 to 4 alkyl carbon atoms, alkoxyalkyl of 2 to 4 carbon atoms, alkenyl of 3 to 5 carbon atoms, alkynyl of 3 to 5 carbon atoms, alkylsulfonyl of 1 to 4 carbon atoms, arylsulfonyl in which aryl is unsubstituted phenyl or phenyl substituted with halogen or alkyl of 1 to 4 carbon atoms, haloalkylsulfonyl of 1 to 4 carbon atoms, alkylaminosulfonyl or dialkylaminosulfonyl in which each alkyl independently is of 1 to 4 carbon atoms, or CH(H or $CH_3)CO_2$alkyl in which alkyl is of 1 to 4 carbon atoms, or N($R^{12}$)($R^{13}$) is a pyrrolidino, piperidino, or morpholino ring;

$R^{14}$ and $R^{15}$ are independently selected from hydrogen, alkyl of 1 to 4 carbon atoms, alkenyl or alkynyl of 3 to 5 carbon atoms, cyanoalkyl of 1 to 4 alkyl carbon atoms, acetyl, alkoxycarbonyl of 1 to 4 alkyl carbon atoms, alkoxyalkyl of 2 to 4 carbon atoms, aminocarbonyl, alkylaminocarbonyl or dialkylaminocarbonyl in which each alkyl is of 1 to 4 carbon atoms, alkylsulfonyl of 1 to 4 carbon atoms, haloalkylsulfonyl of 1 to 4 carbon atoms, arylsulfonyl in which aryl is unsubstituted phenyl or phenyl substituted with halogen or alkyl or 1 to 4 carbon atoms, or CH(H or $CH_3)CO_2$alkyl in which alkyl is of 1 to 4 carbon atoms, or N($R^{14}$)($R^{15}$) is a group N=C($R^9$)($R^{10}$) in which one of $R^9$ and $R^{10}$ is alkyl and the other is hydrogen, alkyl, or alkylthio, each alkyl (independently) being of 1 to 4 carbon atoms, or N($R^{14}$)($R^{15}$) is a tetrahydrophthalimido or 2-oxopyrrolidino group;

$R^{16}$ is hydroxy, amino, alkylamino or dialkylamino in which each alkyl is of 1 to 4 carbon atoms, or arylamino in which aryl is unsubstituted phenyl or phenyl substituted with halogen or alkyl of 1 to 4 carbon atoms; and $R^{17}$ is hydroxy, alkoxy or alkylthio of 1 to 4 carbon atoms, amino, alkylamino or dialkylamino in which each alkyl is of 1 to 4 carbon atoms, or arylamino in which aryl is substituted phenyl or phenyl substituted with halogen or alkyl of 1 to 4 carbon atoms.

2. The compound of claim 1 in which R is alkyl of 1 to 4 carbon atoms, fluoroalkyl of 1 to 4 carbon atoms and 1 to 3 fluorine atoms, alkoxyalkyl or alkylthioalkyl of 2 to 4 carbon atoms, cyanoalkyl of 1 to 3 alkyl carbon atoms, fluoroalkoxyalkyl of 2 to 4 carbon atoms and 1 to 3 fluorine atoms, trifluoromethylthio, alkenyl of 3 to 5 carbon atoms, or fluoroalkenyl of 3 to 5 carbon atoms and 1 or 2 fluorine atoms; $X^1$ is fluorine, chlorine, bromine, methyl, or trifluoromethyl; and $X^2$ is fluorine, chlorine, bromine, methyl, ethyl, bromomethyl, fluoromethyl, trifluoromethyl, or nitro; with the proviso that one of $X^1$ and $X^2$ is fluorine, chlorine, or bromine.

3. The compound of claim 2 in which W is oxygen, R is alkyl of 1 to 4 carbon atoms, fluoroalkyl of 1 to 4 carbon atoms and 1 to 3 fluorine atoms, alkoxyalkyl or alkylthioalkyl of 2 to 4 carbon atoms, cyanoalkyl of 1 to 3 alkyl carbon atoms, 2-(difluoromethoxy)ethyl, trifluoromethylthio, 2-propenyl, or 3-fluoro-2-propenyl, and $X^1$ and $X^2$ are independently selected from fluorine, chlorine, and bromine.

4. The compound of claim 3 in which R is alkyl of 1 to 4 carbon atoms, fluoroalkyl of 1 to 4 carbon atoms and 1 to 3 fluorine atoms, methoxymethyl, methylthiomethyl, or cyanomethyl, $X^1$ is fluorine or chlorine, and $X^2$ is chlorine or bromine.

5. The compound of claim 4 in which R is n-propyl or 3-fluoropropyl and $X^1$ is fluorine.

6. The compound of claim 5 in which R is 3-fluoropropyl and $X^2$ is chlorine.

7. The compound of claim 6 in which Z is N($R^{14}$)($R^{15}$).

8. The compound of claim 7 in which one of $R^{14}$ and $R^{15}$ is hydrogen or alkyl and the other is hydrogen, alkyl, alkenyl, alkynyl, cyanoalkyl, acetyl, alkoxycarbonyl, alkoxyalkyl, aminocarbonyl, alkylaminocarbonyl, dialkylaminocarbonyl, alkylsulfonyl, fluoroalkylsulfonyl, arylsulfonyl (in which aryl is unsubstituted phenyl or phenyl substituted with fluorine, chlorine, or methyl) or CH(H or $CH_3)CO_2$ alkyl; or both of $R^{14}$ and $R^{15}$ are alkylsulfonyl or fluoroalkylsulfonyl; or N($R^{14}$)($R^{15}$) is a group N=C($R^9$ ($R^{10}$) in which one of $R^9$ and $R^{10}$ is alkyl and the other is hydrogen or alkyl; or N($R^{14}$)($R^{15}$) is a tetrahydrophthalimido group or a 2-oxopyrrolidino group.

9. The compound of claim 8 in which at least one of $R^4$ and $R^{15}$ is alkylsulfonyl or fluoroalkylsulfonyl.

10. The compound of claim 7 in which Z is selected from NHCON(CH$_3$)$_2$, NHCONH$_2$, NHCONHCH$_2$CH(CH$_3$)$_2$, NHCONHCH$_3$, NH$_2$, N(CH$_3$)$_2$, NHCH$_3$, N(C$_2$H$_5$)$_2$, NHCH$_2$CH=CH$_2$, NHCH$_2$C≡CH, N(CH$_2$CN)COCH$_3$, N(C$_2$H$_5$)COCH$_3$, NHCOCH$_3$, NHCH$_2$CO$_2$C$_2$H$_5$, NHCO$_2$CH$_3$, NHCH(CH$_3$)CO$_2$C$_2$H$_5$, NHCH$_2$CH$_2$OCH$_3$, NHSO$_2$CH$_3$, N(CH$_3$)SO$_2$CH$_3$, N(C$_2$H$_5$SO$_2$CH$_3$, N(SO$_2$CH$_3$)$_2$, NHSO$_2$CF$_3$, N(SO$_2$CF$_3$)$_2$, NHSO$_2$C$_6$H$_5$, NHSO$_2$—C$_6$H$_4$(4—Cl), NHSO$_2$—C$_6$H$_4$(4—CH$_3$), N=C(CH$_3$)$_2$, N=CHCH$_3$, N=C(CH$_3$)(C$_2$H$_5$), N=C(SCH$_3$)(CH$_3$),

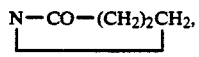

and tetrahydrophthalimido.

11. The compound of claim 8 in which Z is C$_2$H$_5$SO$_2$NH—.

12. The compound of claim 8 in which Z is (C$_2$H$_5$SO$_2$)$_2$N—.

13. An herbicidal composition containing an herbicidally effective amount of a compound of claim 11 in admixture with a suitable carrier.

14. An herbicidal composition containing an herbicidally effective amount of a compound of claim 12 in admixture with a suitable carrier.

15. A method for controlling broad leaf weeds in a locus which is planted or to be planted with corn, rice, wheat or soybeans which comprises applying pre-emergently to said locus an herbicidally effective amount of the composition of claim 13.

16. A method for controlling broad leaf weeds in a locus which is planted or to be planted with soybeans with comprises applying post-emergently to said locus an herbicidally effective amount of the composition of claim 14.

17. Compound of claim 5 in which Z is N(R$^{14}$)(R$^{15}$) and one of R$^{14}$ and R$^{15}$ is alkylsulfonyl or haloalkylsulfonyl.

18. Compound of claim 17 in which one of R$^{15}$ and R$^{14}$ is alkylsulfonyl and the other is hydrogen alkyl or alkylsulfonyl.

19. Compound of claim 17 in which one of R$^{14}$ and R$^{15}$ is alkylsulfonyl and the other is hydrogen.

20. Compound of claim 19 in which W is oxygen, or R is n-propyl or fluoropropyl, and X$^1$ is chlorine or fluorine.

21. Compound of claim 20 in which R is 3-fluoropropyl, X$^1$ is fluorine and X$^2$ is chlorine.

22. Compound of claim 17 in which one of R$^{14}$ and R$^{15}$ is alkyl and the other is alkylsulfonyl.

23. Compound of claim 22 in which W is oxygen, R is n-propyl or fluoropropyl and X$^1$ is chlorine or fluorine.

24. Compound of claim 23 in which R is 3-fluoropropyl, X$^1$ is fluorine and X$^2$ is chlorine.

25. Compound of claim 1 in which Z is nitro.

26. Compound of claim 25 in which W is oxygen, R is n-propyl or fluoropropyl and X$^1$ is chlorine or fluorine.

27. Compound of claim 26 in which R is 3-fluoropropyl; X$^1$ is fluorine and X$^2$ is chlorine.

28. Compound of claim 1 in which Z is amino.

29. Compound of claim 28 in which W is oxygen, R is n-propyl or fluoropropyl and X$^1$ is chlorine or fluorine.

30. Compound of claim 29 in which R is 3-fluoropropyl, X$^1$ is fluorine and X$^2$ is chlorine.

31. An herbicidal composition containing an herbicidally effective amount of a compound of claim 19 in admixture with a suitable carrier.

32. An herbicidal composition containing an herbicidally effective amount of a compound of claim 22 in admixture with a suitable carrier.

33. A method for controlling undesired plant growth which comprises applying to the locus where control is desired an herbicidally effective amount of the composition of claim 31.

34. A method for controlling undesired plant growth which comprises applying to the locus where control is desired an herbicidally effective amount of the composition of claim 31.

35. Compound as in claim 8 in which Z is —N(C$_3$H$_7$)SO$_2$C$_2$H$_5$.

36. An herbicidal composition containing an herbicidally effective amount of a compound of claim 35 in admixture with a suitable carrier.

37. A method for controlling undesired plant growth which comprises applying to the locus where control is desired an herbicidally effective amount of the composition of claim 36.

38. A compound of the formula

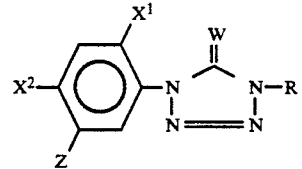

(FORMULA I')

in which W is oxygen or sulfur;

R is alkyl of 1 to 6 carbon atoms, fluoroalkyl of 1 to 5 carbon atoms and one or more fluorine atoms, alkoxyalkyl of 2 to 6 carbon atoms, alkylthioalkyl of 2 to 6 carbon atoms, cyanoalkyl of 1 to 5 alkyl carbon atoms, haloalkoxyalkyl of 2 to 6 carbon atoms, trifluoromethylthio, alkenyl of 2 to 5 carbon atoms, or haloalkenyl of 2 to 5 carbon atoms;

One of X$^1$ and X$^2$ is fluorine, chlorine or bromine and the other is fluorine, chlorine, bromine, alkyl of 1 to 6 carbon atoms, or haloalkyl of 1 to 5 carbon atoms; or X$^1$ is fluorine, chlorine, bromine and X$^2$ is selected from the substituents above and nitro;

Z is —N(R$^{31}$)SO$_2$R$^{30}$

R$^{30}$ is alkyl, haloalkyl or aryl;

R$^{31}$ is hydrogen, alkyl, benzyl, haloalkyl, alkoxy, SO$_2$R, alkynyl, alkenyl, a group of the formula—alkylene—SO$_2$R, alkoxymethyl, cyanomethyl or ethoxycarbonylmethyl; or R$^{30}$ and R$^{31}$ together are alkylene;

Or a salt of an acidic compound of said Formula I'.

39. An herbicidal composition characterized in that it contains an herbicidally effective amount of a compound of claim 1 in admixture with a suitable carrier.

40. A method for controlling undesired plant growth characterized in applying to the locus where control is desired an herbicidally effective amount of the composition of claim 39.

41. The method of claim 40 characterized in that the locus where control is desired is planted or to be planted with soybeans, corn, or cotton.

* * * * *